US007128893B2

(12) United States Patent
Leamon et al.

(10) Patent No.: US 7,128,893 B2
(45) Date of Patent: Oct. 31, 2006

(54) VITAMIN-TARGETED IMAGING AGENTS

(75) Inventors: Christopher P. Leamon, West Lafayette, IN (US); Matthew A. Parker, San Diego, CA (US)

(73) Assignee: Endocyte, Inc., West Lafayette, IN (US)

( * ) Notice: Subject to any disclaimer, the term of this patent is extended or adjusted under 35 U.S.C. 154(b) by 274 days.

(21) Appl. No.: 10/430,519

(22) Filed: May 6, 2003

(65) Prior Publication Data

US 2004/0033195 A1 Feb. 19, 2004

Related U.S. Application Data

(60) Provisional application No. 60/378,571, filed on May 6, 2002.

(51) Int. Cl.
A61K 49/00 (2006.01)
(52) U.S. Cl. .................... 424/9.1; 424/1.11; 424/1.65; 424/1.73
(58) Field of Classification Search ............... 424/1.11, 424/1.37, 1.65, 1.73, 9.1, 9.3, 9.4, 9.5, 9.6, 424/9.7, 9.8; 534/7, 10–16; 568/824; 544/251, 544/327; 546/301; 549/315, 408; 552/653, 552/299
See application file for complete search history.

(56) References Cited

U.S. PATENT DOCUMENTS

| | | | |
|---|---|---|---|
| 2,816,110 A | 12/1957 | Sletzinger et al. | |
| 5,140,104 A | 8/1992 | Coughlin et al. | |
| 5,552,545 A | 9/1996 | Pearce et al. | |
| 5,688,488 A | 11/1997 | Low et al. | |
| 6,335,434 B1 | 1/2002 | Guzaev et al. | |

OTHER PUBLICATIONS

Akihiro Hosomi, Makoto Arita, Yuji Sato, Chikako Kiyose, Tadahiko Ueda, Osamu Igarashi, Hiroyuki Arai, Keizo Inoue; "Affinity for a-tocopherol transfer protein as a determinant of the biological activities of vitamen E analogs," journal article, Federation of European Biochemical Societies, 1997, vol. 409, pp. 105-108.

Kazui Shimizu, Akira Kawase, Tsuyoshi Haneishi, Yasuharu Kato, Takamitsu Kobayashi, Nobuo Sekiguchi, Tessai Yamamoto, Masaki Ishigai, Kazuo Tokuda, Tomochika Matsushita, Shin Shimaoka, and Kazumi Morikawa; "Novel vitamin D3 antipsoriatic antedrugs: 16-En-22-oxa-1a,25-(OH)2D3 analogs," Bioorganic & Medicinal Chemistry 14, 2006, pp. 1838-1850.

Hisashi Takasu, Atsuko Sugita, Yasushi Uchiyama, Nobuyoshi Katagiri, Makoto Okazaki, Etsuro Ogata, Kyoji Ikeda; "c-Fos protein as a target of anti-osteoclastogenic action of vitamin D, and synthesis of new analogs," journal article, The Journal of Clinical Investigation, vol. 116, No. 2, Feb. 2006, pp. 528-535.

Masato Shimizu, Yukiko Miyamoto, EMI Kobayashi, Mika Shimazaki, Keiko Yamamoto, Wolfgang Reischl, Sachiko Yamada; "Synthesis and biological activities of new 1a,25-dihydroxy-19-norvitamin D3 analogs with modifications in both the A-ring and the side chain," journal article, Biorganic & Medicinal Chemistry, 2006, eighteen pages.

E. S. Agoston, M. A. Hatcher, T. W. Kensler, G. H. Posner; Vitamin D Analogs as Anti-Carcinogenic Agents, journal article, Anti-Cancer Agents in Medicinal Chemistry, 2006, pp. 53-71.

G. Robbin Westerhof, Jan C. Schornagel, Ietje Kathmann, Ann L. Jackman, Andre Rosowsky, Ronald A. Forsch, John B. Hynes, F. Thomas Boyle, Godefridus J. Peters, Herbert M. Pinedo, and Gerrit Jansen; "Carrier-and Receptor-Mediated Transport of Folate Antagonists Targeting Folate-Dependent Enzymes: Correlates of Molecular-Structure and Biological Activity," journal article, Molecular Pharmacology, 1995, vol. No. 48, pp. 459-471.

Eugene C. Roberts and Y. Fulmer Shealy, "Folic Acid Analogs. Modifications in the Benzene-Ring Region. 3. Neohomofolic and Neobishomofolic Acids. An Improved Synthesis of Folic Acid and Its Analogs.", journal article, Journal of Medicinal Chemistry, 1973, vol. 16, No. 6, pp. 697-699.

Eugene C. Roberts and Y. Fulmer Shealy, "Folic Acid Analogs. Modifications in the Benzene-Ring Region. 2. Thiazole Analogs," journal article, Journal of Medicinal Chemistry, 1972, vol. 15, No. 12, pp. 1310-1312.

(Continued)

Primary Examiner—Dameron L. Jones
(74) Attorney, Agent, or Firm—Barnes & Thornburg LLP

(57) ABSTRACT

The invention relates to compounds and methods for targeting radionuclide-based imaging agents to cells having receptors for a vitamin, or vitamin receptor binding derivative or analog thereof, by using such a vitamin as the targeting ligand for the imaging agent. The invention provides a compound of the formula $$V-(L)_n-NHCH_2CH-CO-NH-CH(R)CO-NH-CH(COOH)CH_2-SH \text{ or}$$

$$V-(L)_n-NHCH-CO-NH-CH(R)CO-NH-CH(COOH)CH_2-SH$$

for use in such methods. In the compound, V is a vitamin that is a substrate for receptor-mediated transmembrane transport in vivo, or a vitamin receptor binding derivative or analog thereof, L is a divalent linker, R is a side chain of an amino acid, M is a cation of a radionuclide, n is 1 or 0, K is 1 or 0, and the compound can be in a pharmaceutically acceptable carrier therefor. The vitamin-based compounds can be used to target radionuclides to cells, such as a variety of tumor cell types, for use in diagnostic imaging of the targeted cells.

34 Claims, 23 Drawing Sheets

OTHER PUBLICATIONS

Eugene C. Roberts and Y. Fulmer Shealy, "Folic Acid Analogs. Modifications in the Benzene-Ring Region. 1.2'-and 3'-Azafolic Acids," journal article, Journal of Medicinal Chemistry, 1971, vol. 14, No. 2, pp. 125-130.

Louis T. Weinstock, Bernard F. Grabowski, and C. C. Cheng, "Folic Acid Analogs. II. p-{[2,6-Diamino-8-purinyl)methyl]amino}—benzoyl-L-glutamic Acid and Related Compounds," journal article, Journal of Medicinal Chemistry, 1970, vol. 13, No. 5 pp. 995-997.

Lothar Bock, George H. Miller, Klaus-J. Schaper, and Joachim K. Seydel, "Sulfonamide Structure-Activity Relationships in a Cell-Free System. 2. Proof for the Formation of a Sulfonamide-Containing Folate Analog.," journal article, Journal of Medicinal Chemistry, 1974, vol. 17, No. 1, pp. 23-28.

Eugene C. Roberts and Y. Fulmer Shealy, "Folic Acid Analogs. Modifications in the Benzene-Ring Region. 4. 3'- Ethyl—and 3'-Isopropylfolic Acids," journal article, Journal of Medicinal Chemistry, 1974, vol. 17, No. 2, pp. 219-222.

William W. Lee, Abelardo P. Martinez, and Leon Goodman, "Folic Acid Antagonists. Methotrexate Analogs Containing Spurious Amino Acids. Dichlorohomofolic Acid.", journal article, Journal of Medicinal Chemistry, 1974, vol. 17, No. 3, pp. 326-330.

Y. H. Kim, Y. Gaumont, R. L. Kisliuk, and H. G. Mautner, "Synthesis and Biological Activity of 10-Thia-10-deaza Analogs of Folic Acid, Pteroic Acid, and Related Compounds," journal article, Journal of Medicinal Chemistry, 1975, vol. 18, No. 8, pp. 776-780.

M. G. Nair and Patricia T. Campbell, "Folate Analogues Altered in the C9-N10 Bridge Region. 10-Oxafolic Acid and 10-Oxaaminopterin," journal article, Journal of Medicinal Chemistry, 1976, vol. 19, No. 6, pp. 825-829.

Laurence T. Plante, Elizabeth J. Crawford, and Morris Friedkin; "Polyglutamyl and Polylysyl Derivatives of the Lysine Analogues of Folic Acid and Homofolic Acid," journal article, Journal of Medicinal Chemistry, 1976, vol. 19, No. 11, pp. 1295-1299.

John B. Hynes, Donald E. Eason, Claudia M. Garrett, and Perry L. Colvin, Jr., "Quinazolines as Inhibitors of Dihydrofolate Reductase. 4. Classical Analogues of Folic and Isofolic Acids," journal article, Journal of Medicinal Chemistry, 1977, vol. 20, No. 4, pp. 588-591.

John E. Oatis, Jr. and John B. Hynes, "Synthesis of Quinazoline Analogues of Folic Acid Modified at Position 10," journal article, Journal of Medicinal Chemistry, 1977, vol. 20, No. 11, pp. 1393-1396.

M. G. Nair, P. Colleen O'Neal, C. M. Baugh, Roy L. Kisliuk, Y. Gaumont, and Micheal Rodman; "Folate Analogues Altered in the C9-N10 Bridge Region: N10-Tosylisohomofolic Acid and N10-Tosylisohomoaminopterin," journal article, Journal of Medicinal Chemistry, 1978, vol. 21, No. 7, pp. 673-677.

M. G. Nair, Shiang-Yuan Chen, Roy L. Kisliuk, Y. Gaumont, and D. Strumpf; "Folate Analogues Altered in the C9-N10 Bridge Region: 11-Thiohomofolic Acid," journal article, Journal of Medicinal Chemistry, 1979, vol. 22, No. 7, pp. 850-855.

M. G. Nair, Colleen Saunders, Shiang-Yuan Chen, Roy L. Kisliuk, and Y. Gaumont; "Folate Analogues Altered in the C9-N10 Bridge Region. 14. 11-Oxahomofolic Acid, a Potential Antitumor Agent," journal article, J. Med. Chem., 1980, vol. 23, pp. 59-65.

M. G. Nair, Timothy W. Bridges, Timothy J. Henkel, Roy L. Kisliuk, Y. Gaumont, and F. M. Sirotnak; "Folate Analogues Altered in the C9-N10 Bridge Region. 18. Synthesis and Antitumor Evaluation of 11-Oxahomoaminopterin and Related Compounds," journal article, J. Med. Chem., 1981, vol. 24, pp. 1068-1073.

Carroll Temple, Jr., L. Lee Bennett, Jr., Jerry D. Rose, Robert D. Elliott, John A. Montgomery, and John H. Mangum; "Synthesis of Pseudo Cofactor Analogues as Potential Inhibitors of the Folate Enzymes," journal article, J. Med. Chem., 1982, vol. 25, pp. 161-166.

M. G. Nair, Eldridge B. Otis, Roy L. Kisliuk, and Y. Gaumont, "Folate Analogues. 20. Synthesis and Antifolate Activity of 1,2,3,4,5,6,—Hexahydrohomofolic Acid," journal article, J. Med. Chem., 1983, vol. 26, pp. 135-140.

M. G. Nair, David C. Salter, R. L. Kisliuk, Y. Gaumont, G. North, and F. M. Sirotnak; "Folate Analoguess. 21. Synthesis and Antifolate and Antitumor Activities of N10- (Cyanomethyl)-5,8-dideazafolic Acid," journal article, J. Med. Chem., 1983, vol. 26, pp. 605-607.

M. G. Nair, Otha C. Salter, Roy L. Kisliuk, Y. Gaumont, and G. North; "Folate Analogues. 22. Synthesis and Biological Evaluation of Two Analogues of Dihydrofolic Acid Processing a 7,8- Dihydro-8-oxapterin Ring System," journal article, J. Med. Chem., 1983, vol. 26, pp. 1164-1168.

Derrick Lonsdale, "A Review of the Biochemistry, Metabolism and Clinical Benefits of Thiamin(e) and Its Derivatives," publication, Advance Access Publication, vol. 3, Feb. 2006, pp. 49-59.

K. Nosaka, H. Nishimura, and A. Iwashima; "Separate Determination of Anticoccidial Thiamine Analogs by High-performance Liquid Chromatography," journal article, ActaA Vitaminol. Et Enzymol, 1984, vol. 6 (2), pp. 137-142.

Charles T. Kandiko, Daniel Smith, and Brian K. Yamamoto; "Inhibition of Rat Brain Pyruvate Dehydrogenase by Thiamine Analogs," journal article, Biochemical Pharmacology, vol. 37, No. 22, pp. 4375-4380, 1988.

Christina Spry, Christina L. L. Chai, Kiaran Kirk, and Kevin J. Saliba, "A Class of Pantothenic Acid Analogs Inhibits Plasmodium Falciparum Pantothenate Kinase and Represses the Proliferation of Malaria Parasites," journal article, Antimicrobial Agents and Chemotherapy, Nov. 2005, pp. 4649-4657.

Dale R. Sargent, G. Gil Clifton, Sarah R. Bryant, and Charles G. Skinner; "Antimetabolites of Pantothenic Acid, Ureido—and Carbamoyl-Derivatives," journal article, Texas Reports on Biology and Medicine, 1975, vol. 33, No. 3, pp. 433-443.

Abstract, Acta Vitaminol Enzymol, 1982, vol. 4 (1-2), pp. 87-97.

Hiroyuki Kagechika and Koichi Shudo, "Synthetic Retinoids: Recent Developments Concerning Structure and Clinical Utility," journal article, Journal of Medicinal Chemistry, Sep. 22, 2005, vol. 48, No. 19, pp. 5875-5883.

Y. Fulmer Shealy, "Synthesis and Evaluation of Some New Retinoids for Cancer Chemoprevention," Preventive Medicine, 1989, vol. 18, pp. 624-645.

Walter Landuer and Ellen M. Clark, "The Interaction in Teratogenic Activity of the Two Niacin Analogs 3-acetylpyridine and 6-aminonicotinamide," Storrs Agricultural Experiment Station, University of Connecticut, undated, pp. 253-258, year not available.

Paul Renz, Inka Pfitzner, Birgit Endres, and Oliver Hasselwander, "Synthesis of 4-Aza-5, 6-diethylbenzimidazole and Biosynthetic Preparation of 4- and 7-Aza-5, 6-dimethylbenzimidazolylcobamide," journal article, Z. Naturforsch, 1997, vol. 52c, pp. 287-291.V.

William A. Ayers, "Effect of Vitamin B12 and Analogs on the Respiration of a Marine Bacterium," journal article, Archives of Biochemistry and Biophysics, vol. 96, 1962, pp. 210-215.

Tetsuo Toraya and Saburo Fukui, "Immobilized Derivatives of Vitamin B12 Coenzyme and Its Analogs," journal article, Methods in Enzymology, vol. 67, pp. 57-66, year not available.

Masatoshi Ueda and Kazuhisa Taketa, "Effect of Vitamin B12 Derivatives on Urinary Excretion of Methylmalonic Acid in Liver Diseases," journal article, Acta Med. Okayama, vol. 24, 1970, pp. 365-372.

Tetsuo Toraya and Saburo Fukui, "The Synthesis of Several Immobilized Derivatives of Vitamin B12 Coenzyme and Their Use as Affinity Adsorbents for a Study of Interactions of Diol Dehydrase with the Coenzyme," The Journal of Biological Chemistry, vol. 255, No. 8., Issue of Apr. 25, 1980, pp. 3520-3525.

Yusuke Takahata, Ari Nishizawa, Ichiro Kojima, Mamoru Yamanishi, and Tetsuo Toraya, "Synthesis, Properties and Microbiological Activity of Hydrophobic Derivatives of Vitamin B12," journal article, J. Nutr. Sci. Vitaminol., vol. 41, 1995, pp. 515-526.

Maya Kamao, Yoshitomo Suhara, Naoko Tsugawa, Toshio Okano, "Determination of Plasma Vitamin K by High Performance Liquid Chromatography with Fluorescence Detection Using Vitamin K Analogs as Internal Standards," journal article, Journal of Chromatography B, vol. 816, 2005, pp. 41-48.

Yuji Nishikawa, Brian I. Carr, Meifang Wang, Siddhartha Kar, Frances Finn, Paul Dowd, Zhizhen N. Zheng, Jeffrey Kerns, and Sriram Naganathan, "Growth Inhibition of Hepatoma Cells Induced by Vitamin K and Its Analogs," journal article, The Journal of Biological Chemistry, vol. 270, No. 47, Issue of Nov. 24, 1995, pp. 28304-28310.

Donald O. Mack, Max Wolfensberger, Jean-Marie Girardot, Julie A Miller, and B. Connor Johnson, "The Carboxylation Activity of Vitamin K Analogs with Substitutions at Position 2, 3, or 5," The Journal of Biological Chemistry, vol. 254, Issue of Apr. 25, 1979, pp. 2656-2664.

Donald M. Mock and Greg M. Heird, "Urinary Biotin Analogs Increase in Humans During Chronic Supplementation: the Analogs are Biotin Metabolites," The American Physiological Society, 1997, pp. 83-85.

Timothy M. Shoup, Alan J. Fischman, Shreen Jaywook, John W. Babich, H. William Strauss, and David R. Elmaleh; "Synthesis of Fluorine-18-Labeled Biotin Derivatives: Biodistribution and Infection Localization," journal article, J. Nucl. Med. 1994, vol. 35, pp. 1685-1690.

David L. Vesely, Henry C. Wormser, and Hanley N. Abramson, "Biotin Analogs Activate Guanylate Cyclase," journal article, Molecular and Cellular Biochemistry, vol. 60, 1984, pp. 109-114.

J. P. Lambooy, "Riboflavin Analogs Utilized for Metabolism by a Lactobacillus Casei Mutant," Int. J. Biochem., vol. 16, No. 2, 1984, pp. 231-234.

Peter Nielsen, Peter Rauschenbach, and Adelbert Bacher, "Phosphates of Riboflavin and Riboflavin Analogs: A Reinvestigation by High-Performance Liquid Chromatography," journal article, Analytical Biochemistry, vol. 130, 1983, pp. 359-368.

Arya, et al., "Design and Synthesis of Analogs of Vitamin E: Antiproliferative Activity Against Human Breast Adenocarcinoma Cells," journal article, Bioorganic & Medicinal Chemistry Letters, vol. 8, 1998, pp. 2433-2438.

Daniel Trachewsky, "Antihypertensive Effect of Riboflavin Analogs in Rats with Mineralocorticoid-Induced Hypertension," journal article, Hypertension, vol. 3, No. 1, Jan.-Feb. 1981, pp. 75-80.

W.A. Skinner, R. M. Parkhurst, and J. Scholler, "Structure-Activity Relations in the Vitamin E Series. II. Derivatives of a-Tocopherol Substituted at the 5-Methyl Group," journal article, Skinner, Parkhurst, Scholler, and Schwarz, vol. 12, pp. 64-66, year not available.

J. Neuzil, K. Kagedal, L. Andrea, C. Weber, and U.T. Brunk, "Vitamin E Analogs: A New Class of Multiple Action Agents with Anti-Neoplastic and Anti-Atherogenic Activity," Apoptosis, vol. 7, 2002, pp. 179-187.

I. Politis, A Voudouri, I. Bizelis, and G. Zervas, "The Effect of Various Vitamin E Derivatives on the Urokinase-Plasminogen Activator System of Ovine Macrophages and Neutrophils," British Journal of Nutrition, vol. 89, 2003, pp. 259-265.

Xiu-Fang Wang, Paul K. Witting, Brian A. Salvatore, and Jiri Neuzil, "Vitamin E Analogs Trigger Apoptosis in HER2/erbB2-Overexpressing Breast Cancer Cells by Signaling Via the Mitochondrial Pathway," Biochemical and Biophysical Research Communication, vol. 326, 2005, pp. 282-289.

(●) FOLIC ACID
(■) EC20
(▲) EC20:RE ISOMER A
(▼) EC20:RE ISOMER B
(□) DTPA-FOLATE

FIG. 9

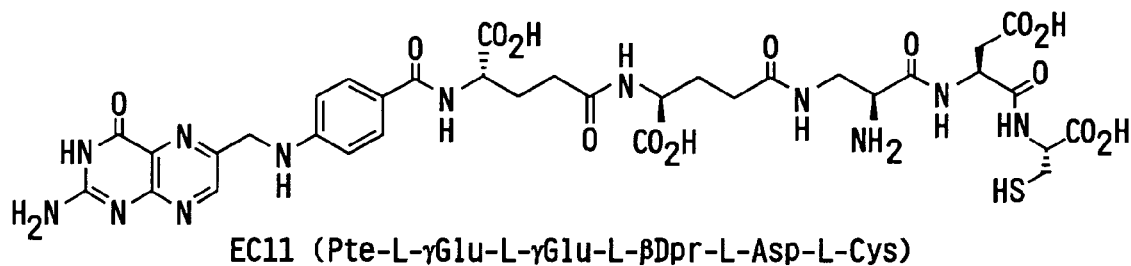
EC11 (Pte-L-γGlu-L-γGlu-L-βDpr-L-Asp-L-Cys)
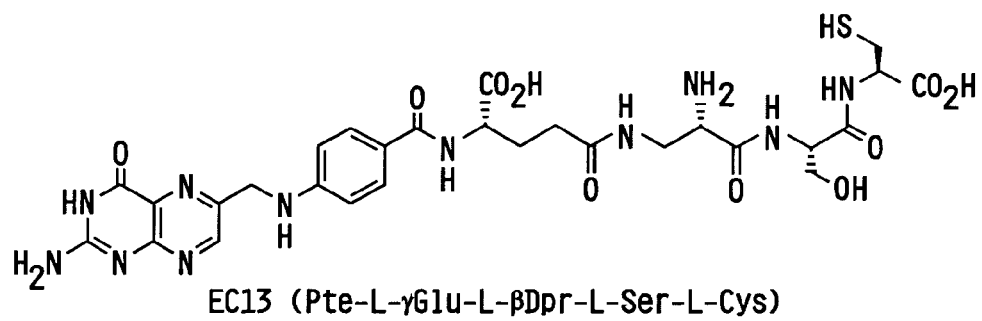
EC13 (Pte-L-γGlu-L-βDpr-L-Ser-L-Cys)
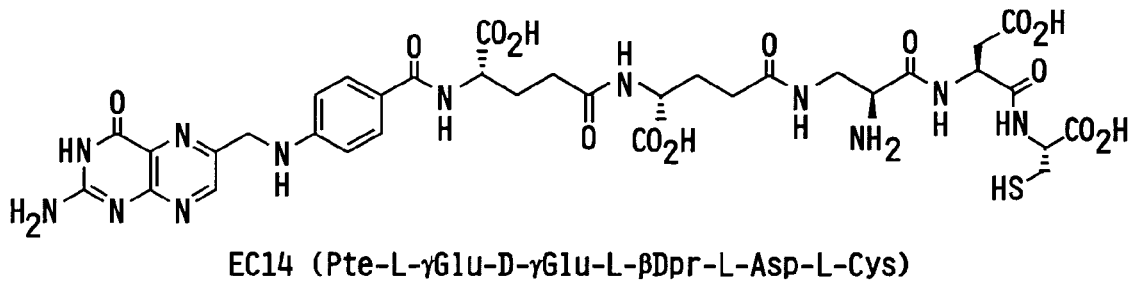
EC14 (Pte-L-γGlu-D-γGlu-L-βDpr-L-Asp-L-Cys)
FIG. 10A

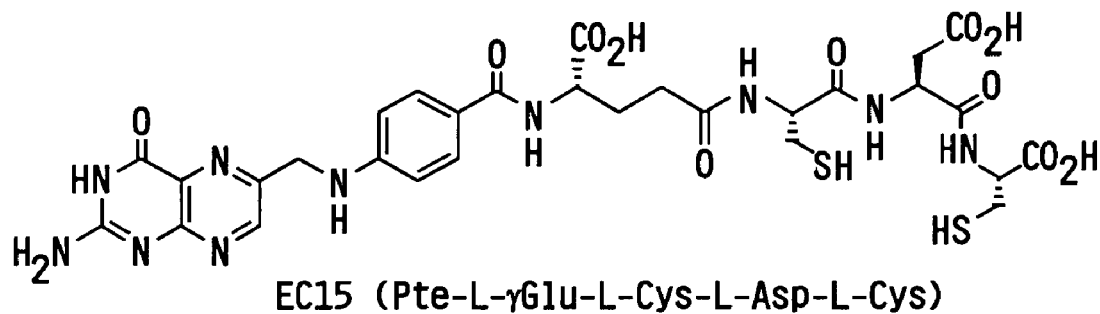
EC15 (Pte-L-γGlu-L-Cys-L-Asp-L-Cys)
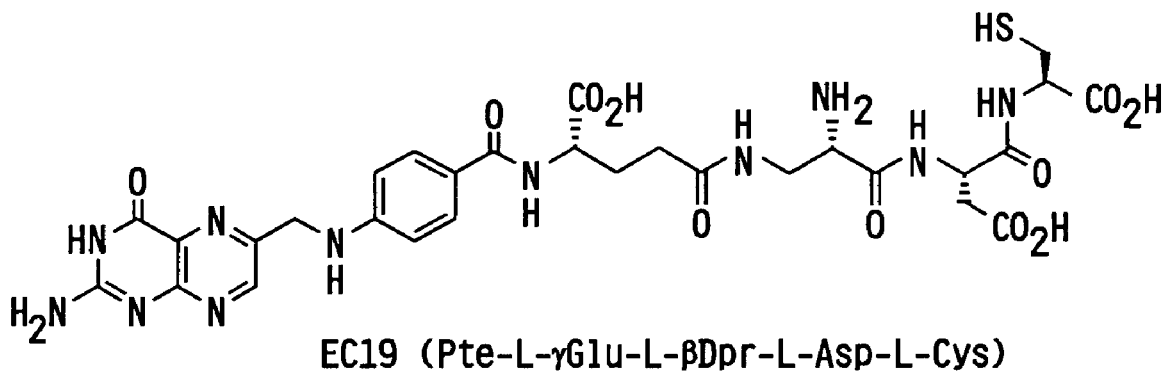
EC19 (Pte-L-γGlu-L-βDpr-L-Asp-L-Cys)
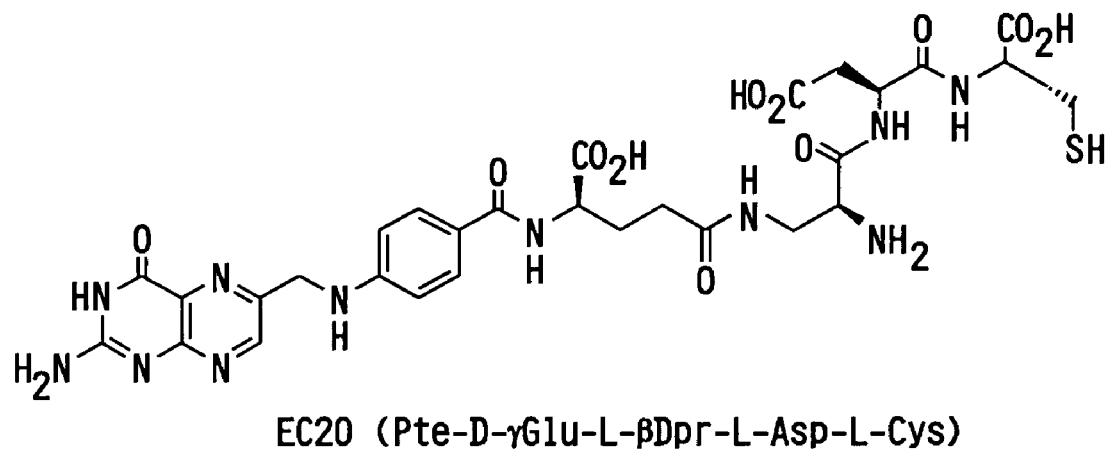
EC20 (Pte-D-γGlu-L-βDpr-L-Asp-L-Cys)
FIG. 10B

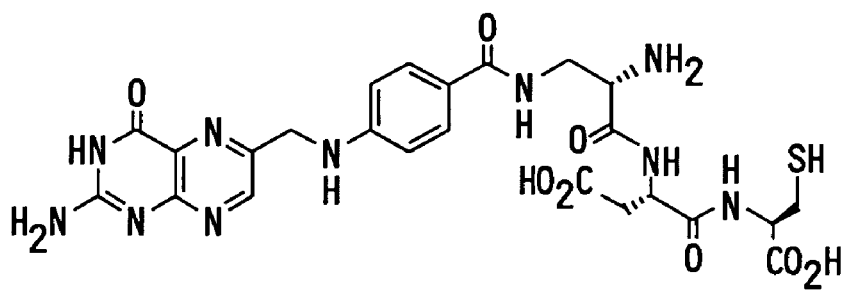
EC31 (Pte-L-βDpr-L-Asp-L-Cys)
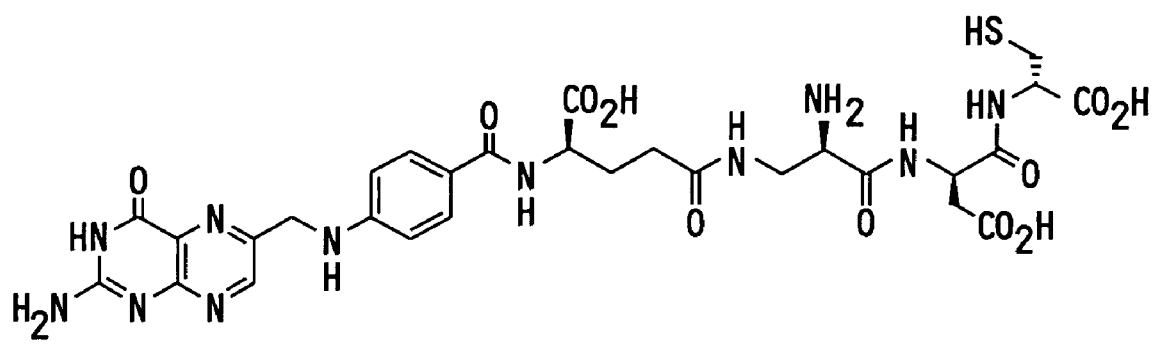
EC53 (Pte-D-γGlu-D-βDpr-D-Asp-D-Cys)
FIG. 10C MOBILE PHASE: A=0.1%TFA IN H2O
B=0.1%TFA IN CH3CN
COLUMN: SYMMETRY C18 (4.6X150 mm). INJECTION: 20ul.
GRADIENT 0%B - 100%B 30MIN. FLOW RATE: 1 ml/min.
CHROMATOGRAM AT 280 nm.
BY LE-CUN XU, Ph.D. ENDOCYTE, INC.

| | |  | |
|---|---|---|---|
| SAMPLE NAME | A5(OLD SAMPLE) | SAMPLE TYPE | UNKNOWN |
| VIAL | 1 | DATE ACQUIRED | |
| INJECTION | 1 | ACQ METHOD SET | G0%B_100%B30MIN1MLMIN |
| INJECTION VOLUME | 20.00μL | PROCESSING METHOD | LC DEFAULT PROCESSING |
| CHANNEL | 996 | DATE PROCESSED | |
| RUN TIME | 20.0 MINUTES | | |

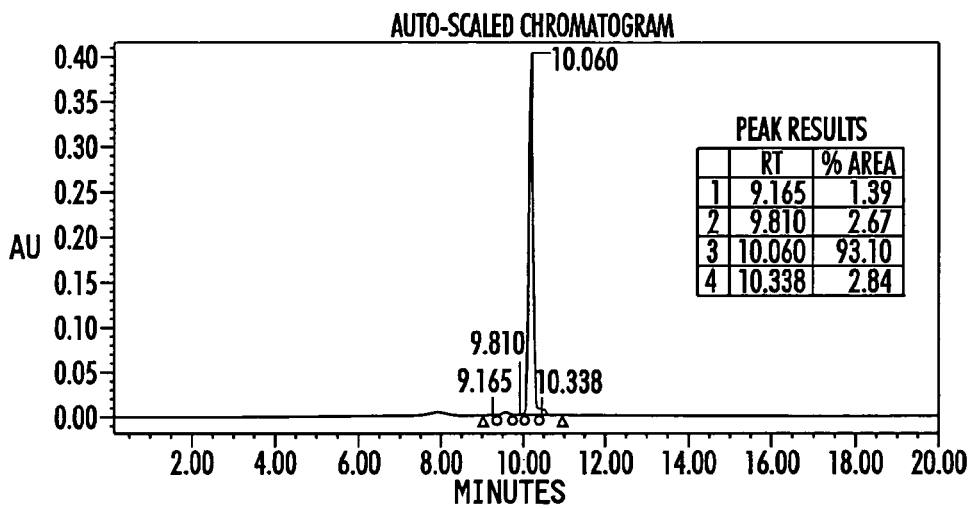

| | SAMPLE NAME | A5(RE-PURIFIED SAMPLE) | SAMPLE TYPE | UNKNOWN |
|---|---|---|---|---|
| | VIAL | 1 | DATE ACQUIRED | |
| | INJECTION | 1 | ACQ METHOD SET | G0%B_100%B30MIN1MLMIN |
| | INJECTION VOLUME | 20.00μL | PROCESSING METHOD | LC DEFAULT PROCESSING |
| | CHANNEL | 996 | DATE PROCESSED | |
| | RUN TIME | 30.0 MINUTES | | |

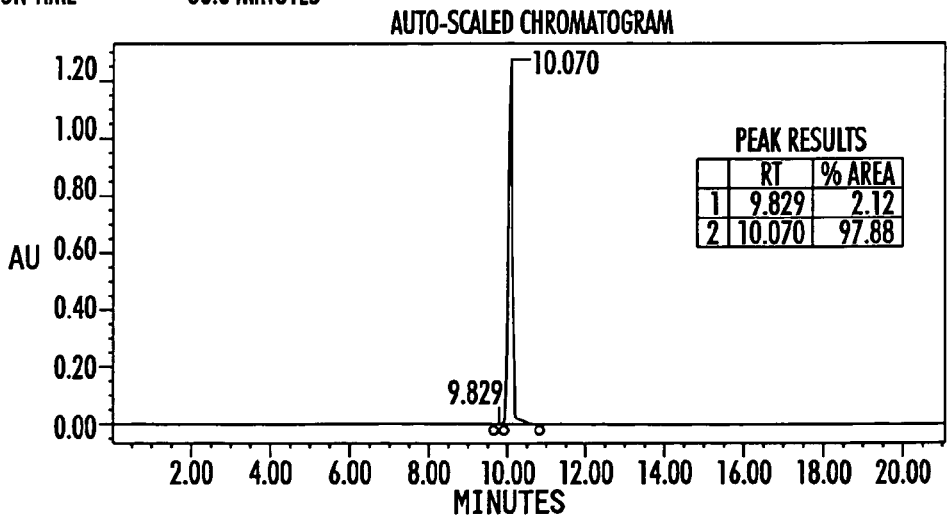

FIG. 18

```
#1 STATUS LOG TIME: 0.01                          VACUUM
API SOURCE                                        VACUUM OK                  :       YES
  SOURCE VOLTAGE (kV)       :      3.52             ION GAUGE PRESSURE OK    :       YES
  SOURCE CURRENT (uA)       :      0.24             ION GAUGE STATUS         :       ON
  VAPORIZER THERMOCOUPLE OK :      NO               ION GAUGE (x10e-5 TORR)  :       1.52
  VAPORIZER TEMP (C)        :     -0.00             CONVECTION PRESSURE OK   :       YES
  SHEATH GAS FLOW RATE ( )  :     58.98             CONVECTION GAUGE (TOR)   :       0.84
  AUX GAS FLOW RATE ( )     :      3.17
  CAPILLARY RTD OK          :      YES            TURBO PUMP
  CAPILLARY VOLTAGE (V)     :     20.64             STATUS                   :       RUNNING
  CAPILLARY TEMP (C)        :    224.60             LIFE (HOURS)             :       16359.00
  8 kV SUPPLY AT LIMIT      :      NO               SPEED (RPM)              :       60000.00
                                                    POWER (WATTS)            :       39.20
                                                    TEMPERATURE (C)          :       40.00
```

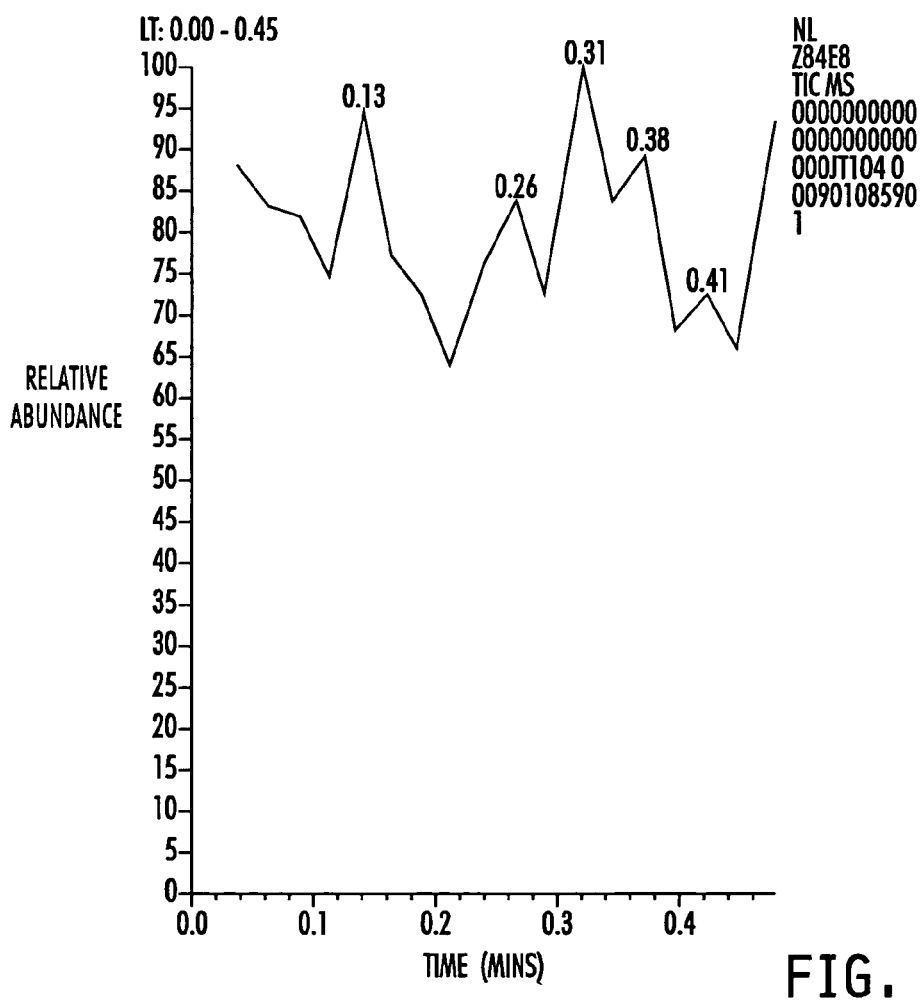

FIG. 22A

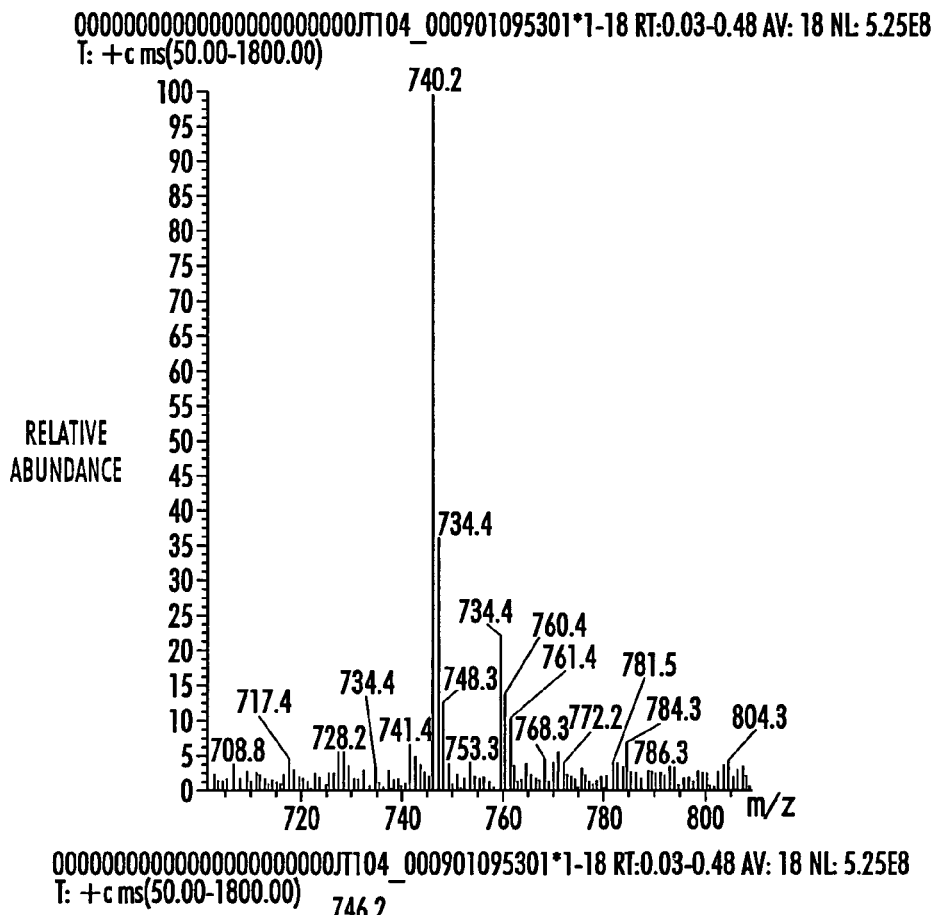
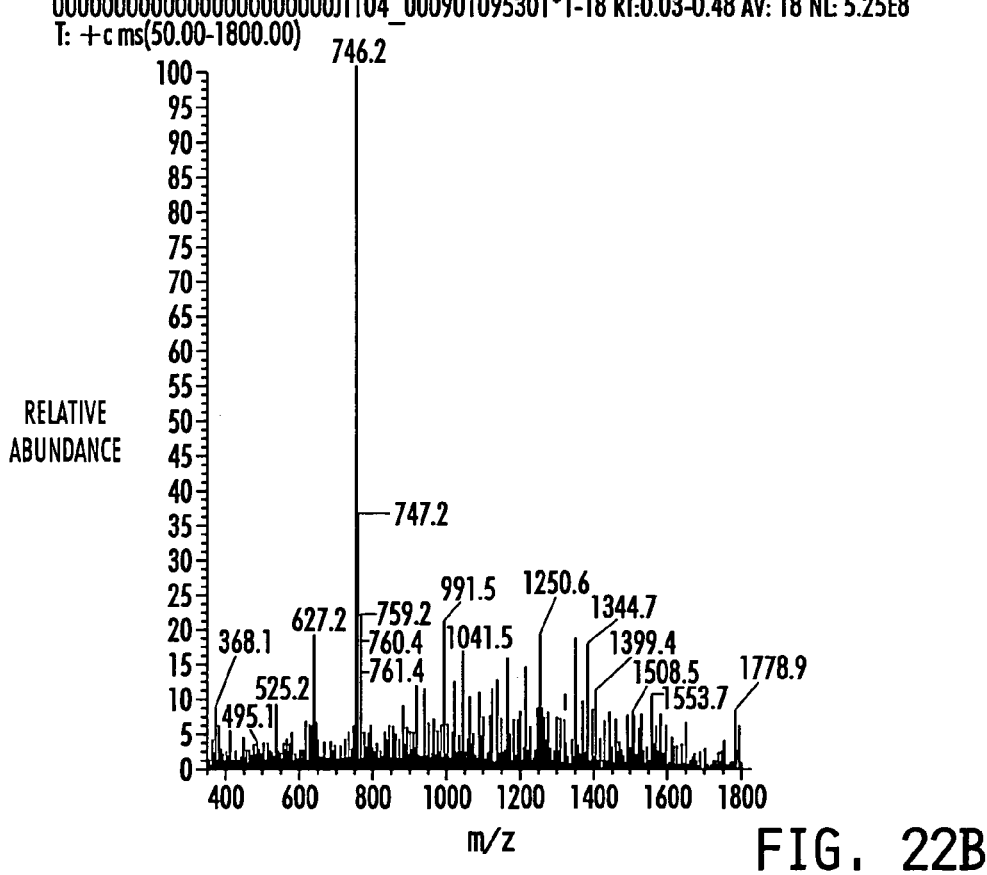
FIG. 22B

1 STATUS LOG TIME: 0.03
API SOURCE

| | | |
|---|---|---|
| SOURCE VOLTAGE (kV) | : | 4.52 |
| SOURCE CURRENT (uA) | : | 19.48 |
| VAPORIZER THERMOCOUPLE OK | : | NO |
| VAPORIZER TEMP (C) | : | -0.00 |
| SHEATH GAS FLOW RATE ( ) | : | 58.93 |
| AUX GAS FLOW RATE ( ) | : | 3.06 |
| CAPILLARY RTD OK | : | YES |
| CAPILLARY VOLTAGE (V) | : | -10.10 |
| CAPILLARY TEMP (C) | : | 225.60 |
| 8 kV SUPPLY AT LIMIT | : | NO |

VACUUM

| | | |
|---|---|---|
| VACUUM OK | : | YES |
| ION GAUGE PRESSURE OK | : | YES |
| ION GAUGE STATUS | : | ON |
| ION GAUGE (x10e-5 TORR) | : | 1.52 |
| CONVECTION PRESSURE OK | : | YES |
| CONVECTION GAUGE (TOR) | : | 0.84 |

TURBO PUMP

| | | |
|---|---|---|
| STATUS | : | RUNNING |
| LIFE (HOURS) | : | 16359.00 |
| SPEED (RPM) | : | 60000.00 |
| POWER (WATTS) | : | 39.20 |
| TEMPERATURE (C) | : | 40.00 |

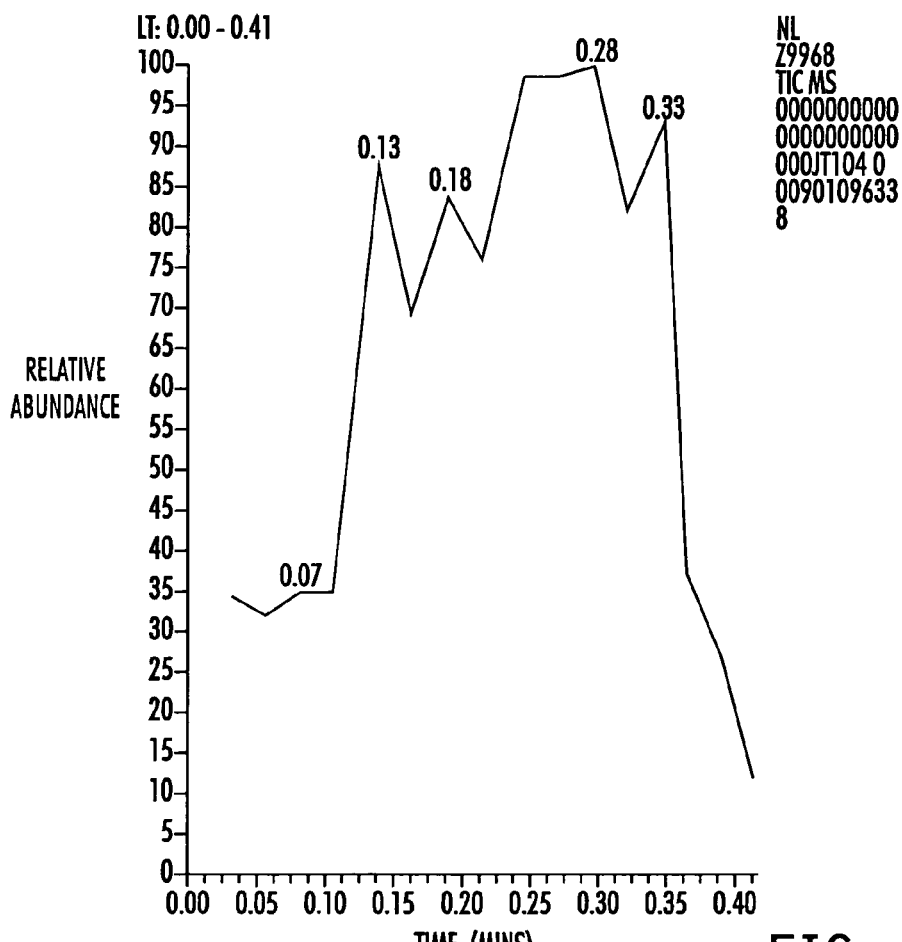

FIG. 23A

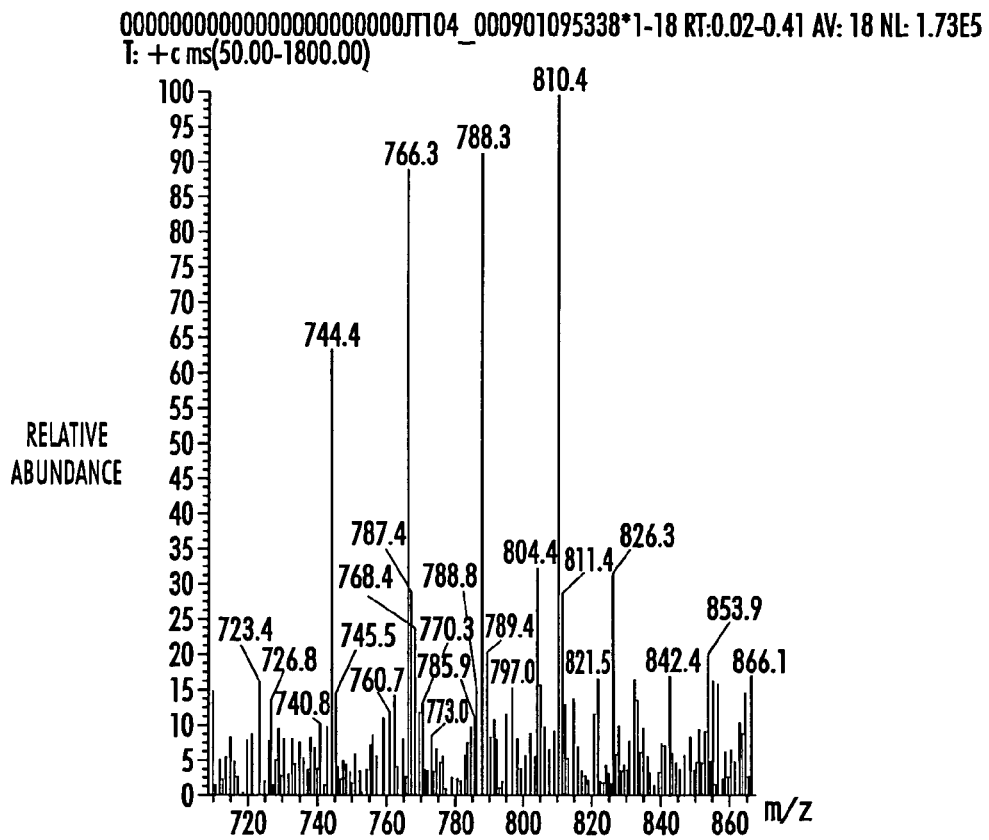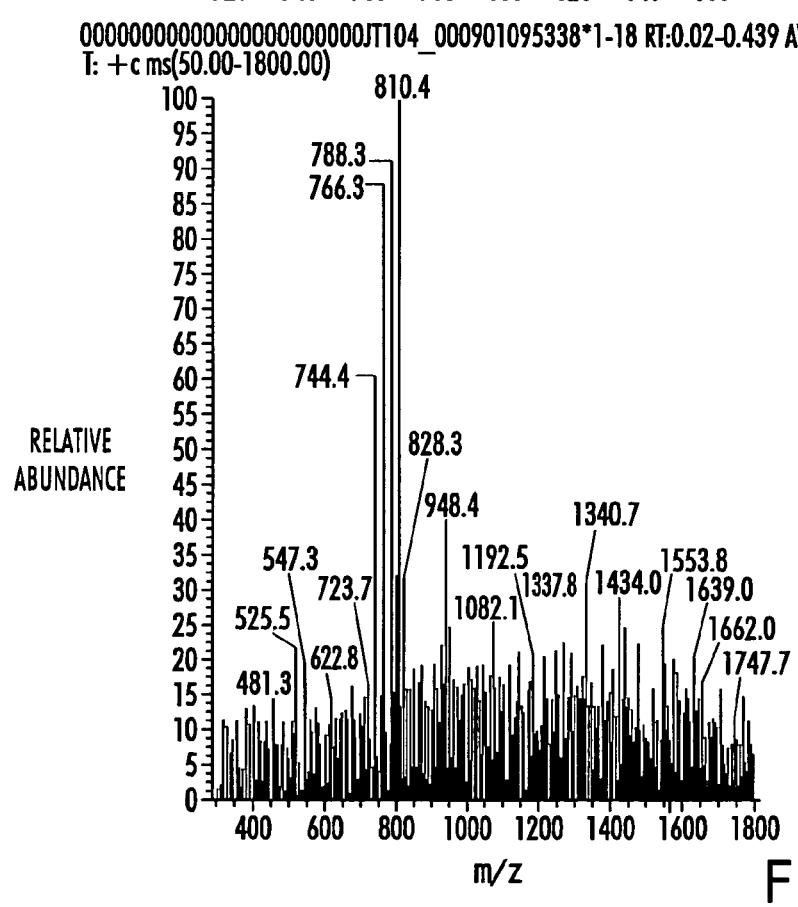
FIG. 23B

VITAMIN-TARGETED IMAGING AGENTS

CROSS REFERENCE TO RELATED APPLICATIONS

This application claims priority under 35 U.S.C. § 119(e) to U.S. Provisional Application Ser. No. 60/378,571, filed on May 6, 2002.

FIELD OF THE INVENTION

The invention relates to compounds and methods for targeting an imaging agent to cells of an animal. More particularly, radionuclide-based imaging agents are targeted to cells having receptors for a vitamin by using such a vitamin, or a vitamin receptor binding derivative or an analog thereof, as the targeting ligand for the imaging agent.

BACKGROUND AND SUMMARY OF THE INVENTION

Transmembrane transport is a critical cellular function. Because practitioners have recognized the importance of transmembrane transport to many areas of medical and biological science, including drug therapy and gene transfer, there have been significant research efforts directed to the understanding and application of such processes. Thus, for example, transmembrane delivery of nucleic acids has been attempted through the use of protein carriers, antibody carriers, liposomal delivery systems, electroporation, direct injection, cell fusion, viral carriers, osmotic shock, and calcium-phosphate mediated transformation. However, many of those techniques are limited both by the types of cells in which transmembrane transport occurs and by the conditions required for successful transmembrane transport of exogenous molecules. Furthermore, many of these techniques are limited by the type and size of the exogenous molecule that can be transported across the cell membrane without loss of bioactivity.

One mechanism for transmembrane transport of exogenous molecules having wide applicability is receptor-mediated endocytosis. Advantageously, receptor-mediated endocytosis occurs both in vivo and in vitro. Receptor-mediated endocytosis involves the movement of ligands bound to membrane receptors into the interior of an area bounded by the membrane through invagination of the membrane. The process is initiated or activated by the binding of a receptor-specific ligand to the receptor. Many receptor-mediated endocytotic systems have been characterized, including those resulting in internalization of galactose, mannose, mannose 6-phosphate, transferrin, asialoglycoprotein, folate, transcobalamin (vitamin $B_{12}$), α-2 macroglobulins, insulin, and other peptide growth factors such as epidermal growth factor (EGF).

Receptor mediated endocytosis has been utilized for delivering exogenous molecules such as proteins and nucleic acids to cells. Generally, a specific ligand is chemically conjugated by covalent, ionic, or hydrogen bonding to an exogenous molecule of interest, forming a conjugate molecule having a moiety (the ligand portion) that is still recognized in the conjugate by a target receptor. Using this technique the phototoxic protein psoralen has been conjugated to insulin and internalized by the insulin receptor endocytotic pathway (Gasparro, Biochem. Biophys. Res. Comm. 141(2), pp. 502–509, Dec. 15, 1986); the hepatocyte specific receptor for galactose terminal asialoglycoproteins has been utilized for the hepatocyte-specific transmembrane delivery of asialoorosomucoid-poly-L-lysine non-covalently complexed to a plasmid (Wu, G. Y., J. Biol. Chem., 262(10), pp. 4429–4432, 1987); the cell receptor for EGF has been utilized to deliver polynucleotides covalently linked to EGF to the cell interior (Myers, European Patent Application 86810614.7, published Jun. 6, 1988); the intestinally situated cellular receptor for the organometallic vitamin $B_{12}$-intrinsic factor complex has been used to mediate delivery of a drug, a hormone, a bioactive peptide and an immunogen complexed with vitamin $B_{12}$ to the circulatory system after oral administration (Russell-Jones et al., European patent Application 86307849.9, published Apr. 29, 1987); the mannose-6-phosphate receptor has been used to deliver low density lipoproteins to cells (Murray, G. J. and Neville, D. M., Jr., J.Biol.Chem, Vol. 255 (24), pp. 1194–11948, 1980); the cholera toxin binding subunit receptor has been used to deliver insulin to cells lacking insulin receptors (Roth and Maddox, J.Cell.Phys. Vol. 115, p. 151, 1983); and the human chorionic gonadotropin receptor has been employed to deliver a ricin a-chain coupled to HCG to cells with the appropriate HCG receptor (Oeltmann and Heath, J.Biol.Chem, vol. 254, p. 1028 (1979)).

In one embodiment the present invention involves the transmembrane transport of a radionuclide-based imaging agent across a membrane having receptors for a vitamin, or a vitamin receptor binding derivative or analog thereof. A cell membrane bearing vitamin receptors, or receptors for vitamin derivatives or analogs, is contacted with a vitamin-imaging agent conjugate for a time sufficient to initiate and permit transmembrane transport of the conjugate, and the biodistribution of the vitamin-imaging agent conjugate in the animal is monitored. In another embodiment, the vitamin/vitamin derivative or analog targeting moiety simply binds to a cell surface vitamin receptor to concentrate the chelated radionuclide on the cell surface.

The invention takes advantage of (1) the location of vitamin receptors and (2) the associated receptor-mediated endocytic processes. For example, the invention takes advantage of the unique expression, overexpression, or preferential expression of vitamin receptors, transporters, or other surface-presented proteins that specifically bind vitamins, or derivatives or analogs thereof, on tumor cells or other cell types which overexpress such receptors. Accordingly, the invention can be used to detect cells, such as tumor cells or other cell types, which overexpress vitamin receptors, or receptors for vitamin derivatives or analogs, by taking advantage of the receptor-mediated endocytic processes that occur when such cells are contacted with the vitamin-imaging agent conjugate.

Vitamin receptors, such as the high-affinity folate receptor (FR) is expressed at high levels, for example, on cancer cells. Epithelial cancers of the ovary, mammary gland, colon, lung, nose, throat, and brain have all been reported to express elevated levels of the FR. In fact, greater than 90% of all human ovarian tumors are known to express large amounts of this receptor. Thus, the present invention can be used for the diagnostic imaging of a variety of tumor types, and of other cell types involved in disease states.

Radionuclide chelators complexed to ligands have been used as non-invasive probes for diagnostic imaging purposes. For example, vasoactive intestinal peptide, somatostatin analogs, and monoclonal antibodies have been used as ligands to localize radionuclides to cells, such as tumor cells. Monoclonal antibodies, and various fragments thereof, initially received the most attention because it was believed that precise tumor-specific targeting might be achieved using monoclonal antibodies as targeting ligands. Unfortunately, this approach was problematic because i) antibodies have prolonged circulation times due to their large size which is unfavorable for imaging purposes, ii) antibodies are expensive to produce, iii) antibodies can be immunogenic, and, accordingly, must be humanized when multiple doses are used, and iv) tumor to non-target tissue ratios (T/NT) of antibody-linked radionuclides are sub-optimal. Thus, the focus has recently been directed to the use of smaller tumor-specific ligands that do not have such limitations.

Vitamins, such as folic acid, have been used for the targeting of imaging agents to tumor cells, and are advantageous because of their small size. The first folic acid-based targeting complex described for in vivo tumor imaging was a histamine derivative containing $^{125}$Iodine. This complex was not considered a relevant clinical candidate because of the long-lived $^{125}$I radionuclide component. Subsequently, a deferoxamine-folate conjugate for tumor imaging was developed (deferoxamine chelates $^{67}$Ga, a gamma-emitting radionuclide that has a 78 hour half-life). Hepatobiliary clearance was noted with this conjugate and, thus, preclinical development was stopped due to anticipated problems in accurately imaging regio-abdominal locations. This obstacle was overcome, however, by replacing the deferoxamine chelator with diethylenetriamine pentaacetic acid (DTPA), an efficient chelator of $^{111}$In (68 hour half life). The primary route of elimination of $^{111}$In-DTPA-folate was confirmed to be through the kidneys.

More recently, $^{99m}$Tc has been adopted as the preferred radionuclide for diagnostic imaging, because i) the radionuclide is easily obtained from commercially available $^{99}$Mo-$^{99m}$Tc generators, ii) the cost of producing large amounts of $^{99m}$Tc is insignificant compared to the cost of producing $^{111}$In, and iii) $^{99m}$Tc has a much shorter (6 hour) half life, which allows higher radionuclide doses to be administered, yielding higher resolution images without the risk of hazardous radiation exposure to vital organs.

Several folate-based $^{99m}$Tc conjugates have been developed. For example, folate conjugates of $^{99m}$Tc-6-hydrazinonicotinamido-hydrazido (HYNIC; Guo, et al., J. Nucl. Med., 40(9): 1563–1569 (1999)), $^{99m}$Tc~12-amino-3,3,9,9-tetramethyl-5-oxa-4,8 diaza-2,10-dodecanedinoe dioxime (OXA) (Linder, et al., Soc. Nucl. Med., Proc. 47$^{th}$ Annual Meeting, 2000, 41(5): 119P), $^{99m}$Tc-ethylenedicysteine (Ilgan, et al., Cancer Biother. & Radiopharm., 13(6): 427–435 (1998)), and $^{99m}$Tc-DTPA~folate (Mathias, et al., Bioconjug. Chem., 11(2): 253–257 (2000)) have shown promising in vivo tumor uptake qualities. However, there is a need for alternative vitamin-based $^{99m}$Tc conjugates, or vitamin-based conjugates employing other radionuclides, that exhibit optimal tumor to non-target tissue ratios (T/NT) and are eliminated through the kidneys. Such vitamin-based conjugates should be suitable for clinical development as tumor imaging agents, and for the diagnosis of other disease states.

In one embodiment is provided a compound of the formula

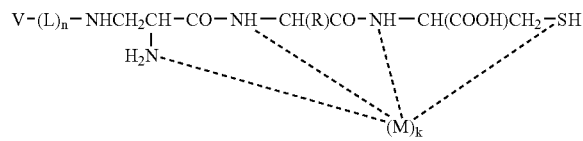

wherein V is a vitamin, or a vitamin receptor binding derivative or analog thereof, L is a divalent linker, R is a side chain of an amino acid of the formula H$_2$NCHRCOOH, M is a cation of a radionuclide, n is 1 or 0, and k is 1 or 0. The vitamin is a substrate for receptor-mediated transmembrane transport in vivo.

In another embodiment is provided a composition for diagnostic imaging comprising a compound of the formula

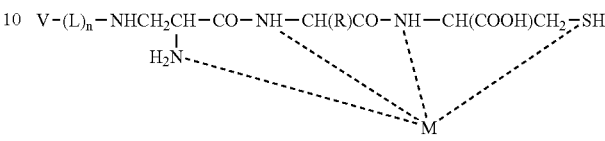

wherein V is a vitamin, or a vitamin receptor binding derivative or analog thereof, L is a divalent linker, R is a side chain of an amino acid of the formula H$_2$NCHRCOOH, M is a cation of a radionuclide, n is 1 or 0, and a pharmaceutically acceptable carrier therefor. The vitamin is a substrate for receptor-mediated transmembrane transport in vivo.

In yet another embodiment a method is provided of imaging a population of cells in an animal, wherein the cells are characterized by a vitamin receptor on the surface of the cells. The method comprises the steps of administering to the animal an effective amount of a composition comprising a compound of the formula

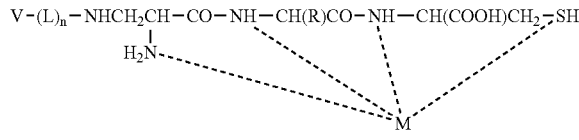

wherein V is a vitamin, or a receptor binding derivative or analog thereof, specific for the cell surface vitamin receptor, L is a divalent linker, R is a side chain of an amino acid of the formula H$_2$NCHRCOOH, M is a cation of a radionuclide, n is 1 or 0, and a pharmaceutically acceptable carrier therefor, and monitoring the biodistribution of the compound in the animal.

In another embodiment a compound is provided of the formula

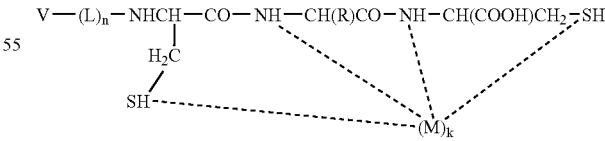

wherein V is a vitamin that is a substrate for receptor-mediated transmembrane transport in vivo, or a vitamin receptor binding derivative or analog thereof, L is a divalent linker, R is a side chain of an amino acid of the formula H2NCHRCOOH, M is a cation of a radionuclide, n is 1 or 0, and k is 1 or 0.

In still another embodiment, a composition for diagnostic imaging is provided comprising a compound of the formula

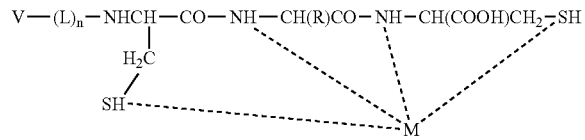

wherein V is a vitamin that is a substrate for receptor-mediated transmembrane transport in vivo, or a vitamin receptor binding derivative or analog thereof, L is a divalent linker, R is a side chain of an amino acid of the formula $H_2NCHRCOOH$, M is a cation of a radionuclide, n is 1 or 0, and a pharmaceutically acceptable carrier therefor.

In yet another embodiment, a method of imaging a population of cells in an animal is provided wherein the cells are characterized by a vitamin receptor on the surface of the cells. The method comprises the steps of administering to the animal an effective amount of a composition comprising a compound of the formula

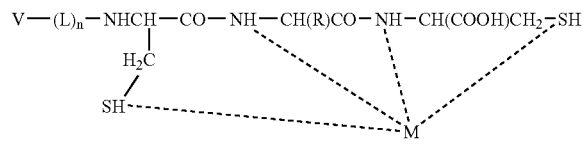

wherein V is the vitamin, or a receptor binding derivative or analog thereof, specific for the cell surface vitamin receptor, L is a divalent linker, R is a side chain of an amino acid of the formula $H_2NCHRCOOH$, M is a cation of a radionuclide, n is 1 or 0, and a pharmaceutically acceptable carrier therefor, and monitoring the biodistribution of the compound in the animal.

In any of these embodiments, V in the compound can be, for example, a vitamin selected from the group consisting of folate, riboflavin, thiamine, vitamin $B_{12}$, and biotin, or a derivative or analog thereof. In any of these embodiments, the radionuclide in the compound can be selected, for example, from the group consisting of radioisotopes of gallium, indium, copper, technetium, and rhenium.

BRIEF DESCRIPTION OF THE DRAWINGS

FIG. 9. Whole-body gamma images (ventral view). Images were obtained 4 hr following intravenous administration of $^{99m}$Tc-EC20 to a Balb/c mouse bearing a subcutaneous folate receptor-positive M109 tumor. Only the kidneys (K) and tumor (T) exhibit significant accumulation of this radiotracer.

FIG. 10. Structures of EC11, EC13, EC14, EC15, EC19, EC20, EC31, and EC53.

FIG. 18. HPLC analysis of EC19.
FIG. 22. Mass spectroscopy analysis of EC53.
FIG. 23. Mass spectroscopy analysis of EC53.

DETAILED DESCRIPTION OF THE INVENTION

In accordance with the invention, compounds and methods are provided for targeting radionuclide-based imaging agents to cell populations that uniquely express, overexpress, or preferentially express vitamin receptors. Accordingly, a vitamin, or a receptor binding derivative or analog thereof, is used as the targeting ligand for the imaging agent. The vitamin-imaging agent conjugate can be used to target radionuclides to cells and to concentrate the radionuclides in a cell population, such as a tumor cell population, for use in diagnostic imaging.

The invention provides a composition for diagnostic imaging comprising a compound of the formula

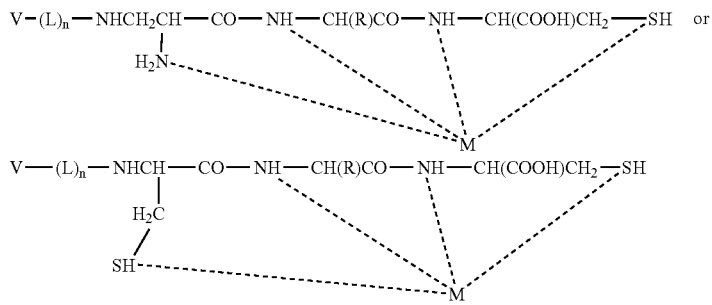

for use in such methods. In the compound, V is a vitamin, or a vitamin receptor binding derivative or analog thereof, L is a divalent linker, R is a side chain of an amino acid of the formula H$_2$NCHRCOOH, M is a cation of a radionuclide, and n is 1 or 0. The vitamin, or vitamin receptor binding derivative or analog thereof, is a substrate for receptor-mediated transmembrane transport in vivo.

The invention also provides compounds of the formulas

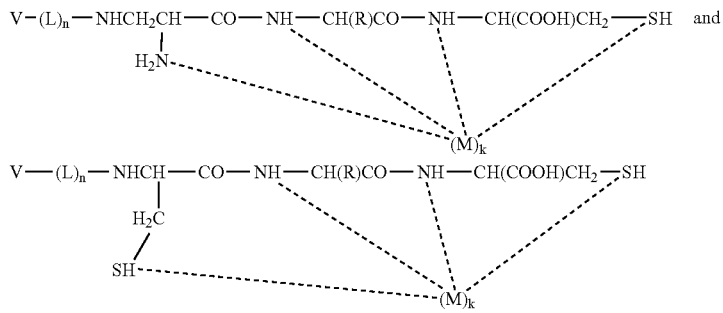

wherein V is a vitamin, or a vitamin receptor binding derivative or analog thereof, L is a divalent linker, R is a side chain of an amino acid of the formula H$_2$NCHRCOOH, M is a cation of a radionuclide, n is 1 or 0, and k is 1 or 0. The vitamin is a substrate for receptor-mediated transmembrane transport in vivo.

Figure 1:
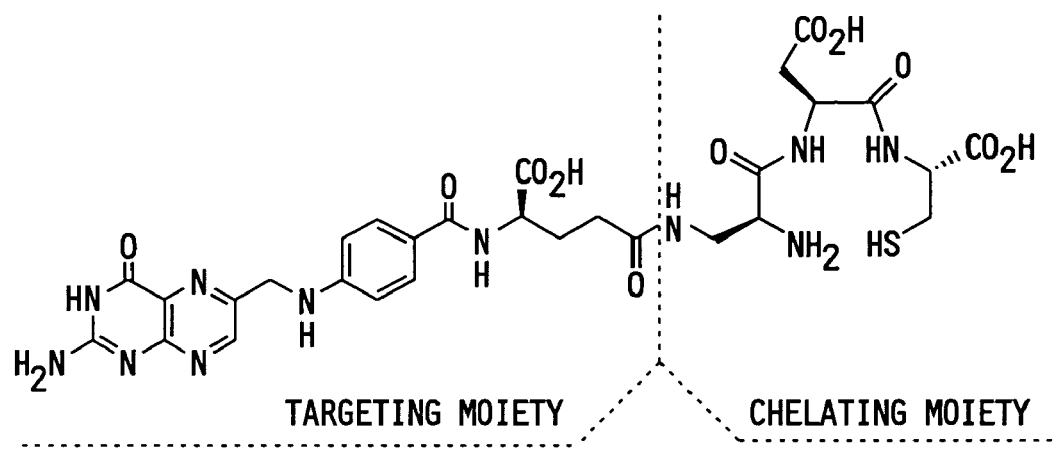
FIG. 1. Structure of EC20, an exemplary compound used as an imaging agent in accordance with the invention.

Exemplary of these compounds is a compound referred to as EC20 depicted in FIG. 1. Exemplary of other compounds for use in accordance with this invention are compounds denominated as EC11, EC13, EC14, EC15, EC19, EC31, and EC53 (see FIG. 10). The vitamin moiety (e.g., the folic acid moiety in EC20) provides high affinity binding to cellular FRs. The compounds also contain a bifunctional peptide-based chelator, which provides the site for chelation of the radionuclide, for example, $^{99m}$Tc (see FIG. 1), and the compounds can, optionally, contain a linker through which the vitamin moiety is covalently bonded to the chelating moiety.

In accordance with the invention, the vitamin moiety of the compounds is a vitamin that is a substrate for receptor-mediated transmembrane transport in vivo, or a vitamin receptor binding derivative or analog thereof. The vitamin is linked, optionally, through a linker (L) to the chelator portion of the compounds. The chelator portion comprises an α, β-diaminopropionic acid moiety linked to a cysteine group through a third amino acid residue. The chelator portion of the compound is adapted to bind a radionuclide cation (M) (where k=1).

In accordance with the invention, the compounds with bound radionuclide are referred to as "vitamin-imaging agent conjugates."

The structure of the linker, if present, is not critical to the invention. Thus, for example, it can be any biocompatible divalent linker. Typically, the linker comprises about 1 to about 30 carbon atoms, more typically about 2 to about 20 carbon atoms. Lower molecular weight linkers (i.e., those having an approximate molecular weight of about 30 to about 300) are typically employed. Furthermore, the vitamin moiety may be a vitamin, or a derivative or analog thereof. For example, folate contains one glutamic acid in the L configuration linked to pteroic acid. As shown in FIG. 1, EC20 comprises a folic acid analog linked to the chelator moiety because EC20 has the glutamic acid in the D configuration. EC11 and EC14 contain two glutamic acid residues and, thus, these compounds can also, for example, be considered derivatives of folic acid (FIG. 10).

Among vitamins believed to trigger receptor-mediated endocytosis and having application in accordance with the presently disclosed method are niacin, pantothenic acid, folic acid, riboflavin, thiamine, biotin, vitamin B$_{12}$, and the lipid soluble vitamins A, D, E and K. These vitamins, and their analogs and derivatives, constitute vitamins that can be coupled with imaging agents to form the vitamin-chelator conjugates for use in accordance with the invention. Preferred vitamin moieties include folic acid, biotin, riboflavin, thiamine, vitamin $B_{12}$, and analogs and derivatives of these vitamin molecules, and other related vitamin receptor-binding molecules.

Folic acid, folinic acid, pteroic acid, pteropolyglutamic acid, and folate receptor-binding pteridines such as tetrahydropterins, dihydrofolates, tetrahydrofolates, and their deaza and dideaza analogs can be used in accordance with the invention. The terms "deaza" and "dideaza" analogs refers to the art-recognized folate analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5dideaza, 5,10-dideaza, 8,10-dideaza, and 5,8-dideaza analogs. The foregoing are folate analogs or derivatives and can bind to folate receptors. Other folate analogs or derivatives useful in accordance with the invention are the folate receptor-binding analogs aminopterin, amethopterin (methotrexate), $N^{10}$-methylfolate, 2-deamino-hydroxyfolate, deaza analogs such as 1-deazamethopterin or 3-deazamethopterin, and 3'5'-dichloro-4-amino-4-deoxy-$N^{10}$-methylpteroylglutamic acid (dichloromethotrexate).

The vitamin, or derivative or analog thereof, can be capable of selectively binding to the population of cells to be visualized due to preferential expression on the targeted cells of a receptor for the vitamin, or derivative or analog, wherein the receptor is accessible for binding. The binding site for the vitamin can include receptors for any vitamin molecule capable of specifically binding to a receptor wherein the receptor or other protein is uniquely expressed, overexpressed, or preferentially expressed by the population of cells to be visualized. A surface-presented protein uniquely expressed, overexpressed, or preferentially expressed by the cells to be visualized is a receptor not present or present at lower amounts on other cells providing a means for selective, rapid, and sensitive visualization of the cells targeted for diagnostic imaging using the vitamin-imaging agent conjugates of the present invention.

In accordance with the invention the vitamin-imaging agent conjugates are capable of high affinity binding to receptors on cancer cells or other cells to be visualized. The high affinity binding can be inherent to the vitamin moiety or the binding affinity can be enhanced by the use of a chemically modified vitamin (i.e., an analog or a derivative) or by the particular chemical linkage between the vitamin and the chelator moiety that is present in the conjugate.

In accordance with the invention, the chelator can be conjugated with multiple, different vitamins, or vitamin receptor binding derivatives or analogs, to enhance the opportunity for binding to the respective cell membrane receptors. Alternatively, independent portions of the dose of a vitamin-imaging agent conjugate can constitute different vitamin-imaging agent conjugates to enhance the opportunity for binding to the respective cell membrane receptors.

Generally, any manner of forming a complex between the chelator and the vitamin, or vitamin receptor binding derivative or analog, can be utilized in accordance with the present invention. The chelator can form a complex with the vitamin, or vitamin receptor binding derivative or analog, by direct conjugation of the chelator and the vitamin by using a divalent linker. Alternatively, the vitamin and the chelator may be conjugated without employing a linker. If a linker is used, the linker can directly conjugate the vitamin, or vitamin receptor binding derivative or analog, and the chelator through a hydrogen, ionic, or covalent bond. Also, in accordance with this invention the divalent linker can comprise an indirect means for associating the chelator with the vitamin, or vitamin receptor binding derivative or analog, such as by connection through intermediary linkers, spacer arms, or bridging molecules. Both direct and indirect means for association must not prevent the binding of the vitamin, or vitamin receptor binding derivative or analog, to the vitamin receptor on the cell membrane for operation of the method of the present invention.

Covalent bonding of the vitamin, or vitamin receptor binding derivative or analog, and the chelator can occur, whether or not a linker is employed, through the formation of amide, ester or imino bonds between acid, aldehyde, hydroxy, amino, or hydrazo groups. For example, a carboxylic acid on the vitamin moiety or on the chelator can be activated using carbonyldiimidazole or standard carbodiimide coupling reagents such as 1-ethyl-3-(3-dimethylaminopropyl)-carbodiimide (EDC) and thereafter reacted with the other component of the conjugate, or with a linker, having at least one nucleophilic group, viz hydroxy, amino, hydrazo, or thiol, to form the vitamin-chelator conjugate coupled, with or without a linker, through ester, amide, or thioester bonds.

The radionuclides suitable for diagnostic imaging include radioisotopes of gallium, indium, copper, technetium and rhenium, including isotopes $^{111}$In, $^{99m}$Tc, $^{64}$Cu, $^{67}$Cu, $^{67}$Ga or $^{68}$Ga. These radionuclides are cationic and are complexed with the chelator through the chelating group of the conjugate to form the vitamin-imaging agent conjugate.

The vitamin-imaging agent conjugates in accordance with the invention are utilized to selectively visualize, using scintigraphic imaging techniques, a population of cells in an animal wherein the population of cells uniquely expresses, overexpresses, or preferentially expresses receptors for a vitamin, or a vitamin receptor binding derivative or analog thereof. The vitamin-imaging agent conjugates can be used to visualize populations of pathogenic cells, as long as the cells uniquely or preferentially express or overexpress vitamin receptors or receptors that bind vitamin derivatives or analogs.

The invention is applicable to populations of pathogenic cells that cause a variety of pathologies including cancer, and diseases mediated by any other type of pathogenic cells that overexpress vitamin receptors, or receptors capable of binding vitamin derivatives or analogs. Thus, the population of pathogenic cells can be tumorigenic, including benign tumors and malignant tumors, or it can be non-tumorigenic. If the cell population is a cancer cell population, the cancer cells can arise spontaneously or by such processes as mutations present in the germline of the host animal or somatic mutations, or the cancer can be chemically-, virally-, or radiation-induced. The invention can be utilized for diagnostic imaging of such cancers as carcinomas, sarcomas, lymphomas, Hodgekin's disease, melanomas, mesotheliomas, Burkitt's lymphoma, nasopharyngeal carcinomas, and myelomas. The cancer cell population can include, but is not limited to, oral, nasopharyngeal, thyroid, endocrine, skin, gastric, esophageal, laryngeal, throat, pancreatic, colon, bladder, bone, ovarian, cervical, uterine, breast, testicular, prostate, rectal, kidney, liver, lung, and brain cancers. In embodiments where the cell population is a cancer cell population, tumor cells, including cells of the primary tumor or cells that have metastasized or are in the process of dissociating from the primary tumor, can be visualized using the vitamin-imaging agent conjugate.

The vitamin-imaging agent conjugates of the present invention can be used to diagnose a disease state or to monitor the progression of disease. For example, the diagnostic imaging method in accordance with the invention can be used to monitor the progression of cancer in combination with prophylactic treatments to prevent return of a tumor after its removal by any therapeutic approach including surgical removal of the tumor, radiation therapy, chemotherapy, or biological therapy.

The compositions and methods of the present invention can be used for both human clinical medicine and veterinary applications. Thus, the animal harboring the population of cells that are visualized can be human or, in the case of veterinary applications, can be a laboratory, agricultural, domestic, or wild animal. The present invention can be applied to animals including, but not limited to, humans, laboratory animals such rodents (e.g., mice, rats, hamsters, etc.), rabbits, monkeys, chimpanzees, domestic animals such as dogs, cats, and rabbits, agricultural animals such as cows, horses, pigs, sheep, goats, and wild animals in captivity such as bears, pandas, lions, tigers, leopards, elephants, zebras, giraffes, gorillas, dolphins, and whales.

The compositions for diagnostic imaging comprise an amount of the vitamin-imaging agent conjugate effective to visualize the cells targeted for diagnostic imaging in an animal when administered in one or more doses. The diagnostic imaging composition containing the vitamin-imaging agent conjugate is preferably administered to the animal parenterally, e.g., intradermally, subcutaneously, intramuscularly, intraperitoneally, intravenously, or intrathecally. Alternatively, the composition containing the vitamin-imaging agent conjugate can be administered to the animal by other medically useful processes, and any effective dose and suitable dosage form can be used, including oral and inhalation dosage forms.

Examples of parenteral dosage forms include aqueous solutions of the vitamin-imaging agent conjugate, in isotonic saline, 5% glucose or other well-known pharmaceutically acceptable liquid carriers such as liquid alcohols, glycols, esters, and amides. The parenteral dosage form in accordance with this invention can be in the form of a reconstitutable lyophilizate comprising the dose of the vitamin-imaging agent conjugate.

The dosage of the vitamin-imaging agent conjugate in the diagnostic imaging composition can vary significantly depending on the size of the animal, the cell population targeted for diagnostic imaging, the specific vitamin-imaging agent conjugate being used, and the route of administration of the conjugate. The effective amount to be administered to the animal is based on body surface area, weight, and physician assessment of the condition of the animal. An effective dose can range from about 1 ng/kg to about 1 mg/kg, more preferably from about 100 ng/kg to about 500 µg/kg, and most preferably from about 100 ng/kg to about 25 µg/kg.

Any effective regimen for administering the diagnostic imaging composition containing the vitamin-imaging agent conjugate can be used. For example, the diagnostic imaging composition can be administered as a single dose, or it can be administered in multiple doses, if necessary, to achieve visualization of the targeted cell population. Additional injections of the diagnostic imaging composition containing the vitamin-imaging agent conjugate can be administered to the animal at an interval of days or months after the initial injections(s), and the additional injections can be useful for monitoring the progress of the disease state. The diagnostic imaging composition containing the vitamin-imaging agent conjugate can also be administered in combination with unlabeled vitamin. "In combination with" means that the unlabeled vitamin can be either coadministered with the imaging agent or the unlabeled vitamin can be preinjected before administration of the imaging agent to improve image quality. For example, the imaging agent can be administered in combination with about 0.5 ng/kg to about 100 mg/kg, or about 1 µg/kg to about 100 mg/kg, or about 100 µg/kg to about 100 mg/kg of the unlabeled vitamin.

The diagnostic imaging composition is typically formulated for parenteral administration and is administered to the animal in an amount effective to enable imaging of the targeted cell population. Typically, the diagnostic imaging composition containing the vitamin-targeted imaging agent is administered to the animal, and following a period of time to allow delivery and concentration of the vitamin-imaging agent conjugate in the targeted cell population, the animal is subjected to the imaging procedure and imaging is enabled by the vitamin-imaging agent conjugate. When used for monitoring the progression of disease or diagnosis, imaging procedures are typically carried out about 1 to about 6 hours post administration of the diagnostic imaging composition containing the vitamin-imaging agent conjugate.

The invention also provides a method of imaging a population of cells in an animal wherein the cells are characterized by a vitamin receptor on the surface of the cells. The method comprises the steps of administering to the animal an effective amount of a composition comprising a compound of the formula

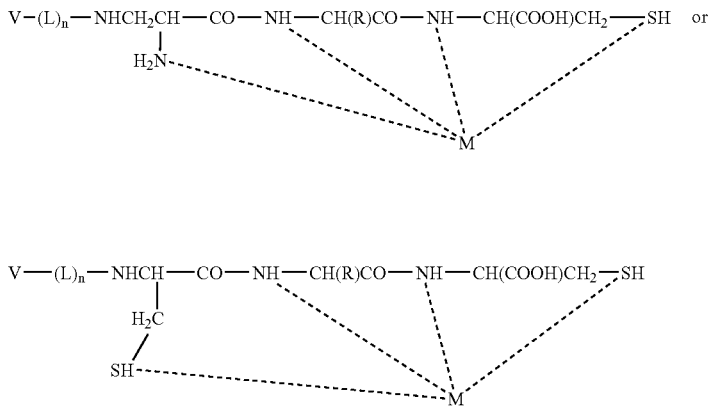

wherein V is the vitamin, or a receptor binding derivative or analog thereof, specific for the cell surface vitamin receptor, L is a divalent linker, R is a side chain of an amino acid of the formula $H_2NCHRCOOH$, M is a cation of a radionuclide, n is 1 or 0, and a pharmaceutically acceptable carrier therefor, and monitoring the biodistribution of the compound in the animal.

The method can be used to image a cell population in vitro, e.g., in cell culture, or in vivo, where the cells form part of or otherwise exist in animal tissue. Thus, the target cells can include, for example, the cells lining the alimentary canal, such as the oral and pharyngeal mucosa, the cells forming the villi of the small intestine, or the cells lining the large intestine. Such cells of the alimentary canal can be targeted in accordance with this invention by oral administration of a diagnostic imaging composition comprising the vitamin-imaging agent conjugate. Similarly, cells lining the respiratory system (nasal passages/lungs) of an animal can be targeted by inhalation of the present complexes, and cells of internal organs, including cells of the ovaries and the brain can be targeted, particularly, by parenteral administration of the diagnostic imaging composition.

EXAMPLE 1

Materials.

$N^{10}$-trifluoroacetylpteroic acid was purchased from Eprova AG, Schaffhausen, Switzerland. Peptide synthesis reagents were purchased from NovaBiochem and Bachem. $^{99m}$Tc Sodium Pertechnetate was supplied by Syncor. [ReO$_2$(en)$_2$]Cl was prepared according to Rouschias (Rouschias, G., Chem. Rev., 74: 531 (1974)). Cellulose plates and DEAE ion exchange plates were purchased from J.T. Baker.

EXAMPLE 2

Synthesis, Purification, and Analytical Characterization of EC20.

EC20 was prepared by a polymer-supported sequential approach using the Fmoc-strategy (see Scheme 1 below; Fmoc=9-fluorenylmethyloxycarbonyl; Boc=tert.butyloxycarbonyl; Dap=diaminopropionic acid; DMF=dimethylformamide; DIPEA=diisopropylethylamine). EC20 was synthesized on an acid-sensitive Wang resin loaded with Fmoc-$_L$-Cys(Trt)-OH. Benzotriazole-1-yl-oxy-tris-pyrrolidino-phosphonium-hexafluorophosphate (PyBOP) was applied as the activating reagent to ensure efficient coupling using low equivalents of amino acids. Fmoc protecting groups were removed after every coupling step under standard conditions (20% piperidine in DMF). After the last assembly step the peptide was cleaved from the polymeric support by treatment with 92.5% trifluoroacetic acid containing 2.5% ethanedithiol, 2.5% triisopropylsilane and 2.5% deionized water. This reaction also resulted in simultaneous removal of the t-Bu, Boc and trityl protecting groups. Finally, the trifluoroacetyl moiety was removed in aqueous ammonium hydroxide to give EC20.

The crude EC20 product was purified by HPLC using an Xterra RP18 30×300 mm, 7 μm column (Waters); mobile phase 32 mM HCl (A), MeOH (B); gradient conditions starting with 99% A and 1% B, and reaching 89% A and 11% B in 37 min by a flow rate of 20 mL/min. Under these conditions, EC20 monomer typically eluted at 14.38 min, whereas EC20 disulfide dimer (minor contaminant) eluted at 16.83 min. All other compounds shown in FIG. 10 can be prepared using a similar synthesis scheme except for EC15 which is synthesized as shown in Scheme 2 below.

Two milligrams of HPLC-purified EC20 were dissolved in 0.62 mL of D$_2$O, and a 500 MHz $^1$H-NMR spectrum was collected. Table 1 (see below) lists the chemical shifts, signal shapes, and J values for all non-exchangeable protons in EC20 molecule.

EC20 was also analyzed by electrospray-mass spectrometry. Major positive ion peaks (m/z, relative intensity): 746.1, 100; 747.1, 44; 556.8, 32; 570.8, 16.

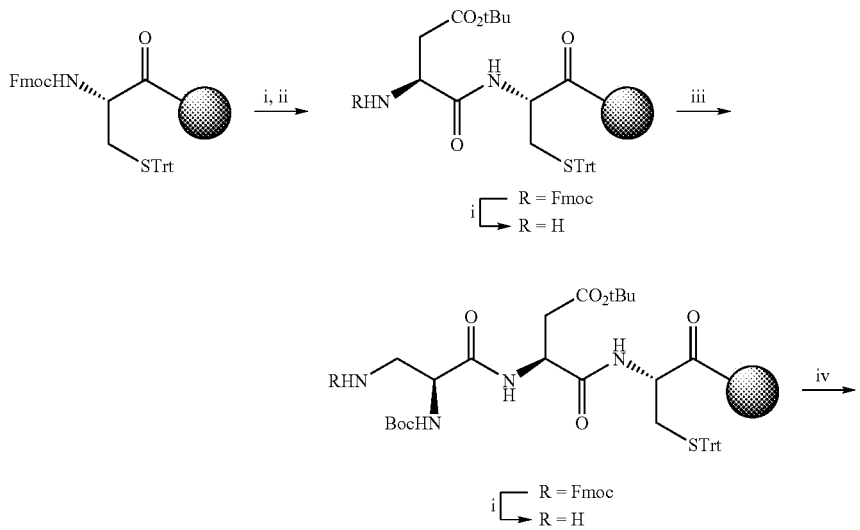

Scheme 1$^a$

-continued

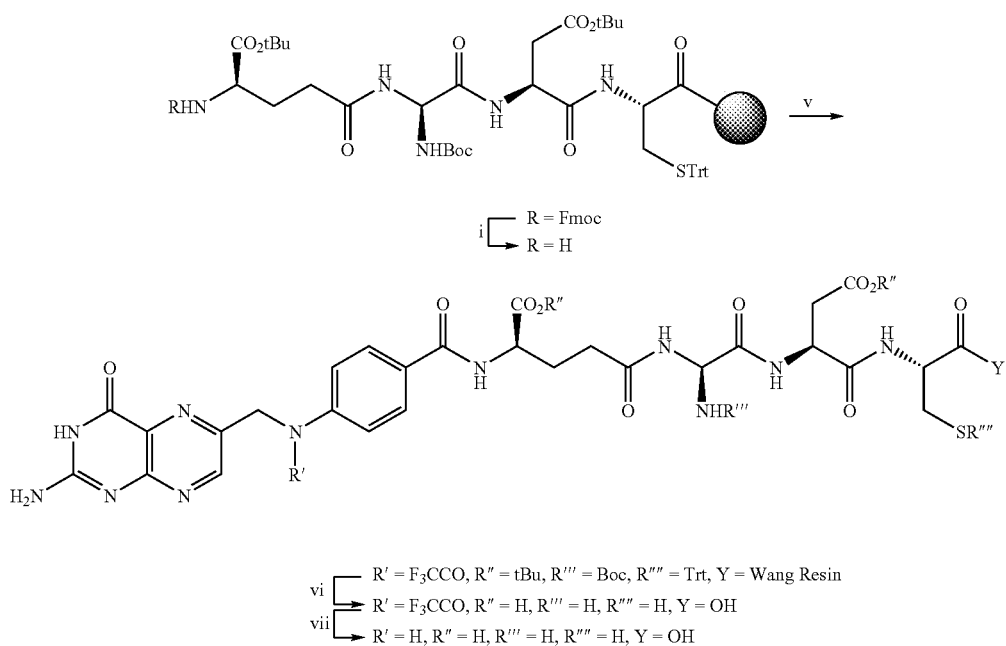

a Reagents and conditions: i) 20% Piperidine, DMF; ii) Fmoc-Asp(OtBu)-OH, PyBop, DIPEA, DMF; iii) Boc-Dap(Fmoc)-OH, PyBop, DIPEA, DMF; iv) Fmoc-D-Glu-OtBu, PyBop, DIPEA, DMF; v) $N^{10}$-TFA-Pte-OH, DIPEA, DMSO; vi) $F_3CCO_2H$, $HSCH_2CH_2SH$, $iPr_3SiH$; vii) $H_4NOH$, pH = 10.3.

TABLE 1

$^1$H-NMR data for EC20. EC20 was dissolved in $D_2O$ and a 500 MHz spectrum was collected. Chemical shifts (δ) are in ppm. The signal for HOD at δ = 4.80 ppm was used as the reference. pD = 4.78; s = singlet; d = doublet; m = multiplet.

| Residue | Protons observed | Chemical Shift (δ) | Signals | J values |
|---|---|---|---|---|
| Pte | H-7 | 8.76 | s | $^3$J12, 13=$^3$J15, 16=8.8 Hz |
|  | 2 x H-9 | 4.64 | s |  |
|  | H-12 a. H-16 | 7.68 | d |  |
|  | H-13 a. H-15 | 6.8 | d |  |
| D-Glu | H-2 | 4.41 | dd | $^3$J2, 3=$^3$9.1 Hz; $^3$J2, 3b=4.5 Hz |
|  | H-3a | 2.08 | m | $^2$J3a, 3b = 14.2 Hz |
|  | H-3B | 2.27 | m | $^3$J3a, 4 = $^3$J4b, 4 = 5.6 Hz |
|  | 2 x H-4 | 2.44 | dd |  |
| Dpr | H-2 | 4.1 | dd; X of ABX System | $^3$J2, 3A=6.6 Hz; $^3$J2, 3B=4.7 Hz |
|  | H-3A | 3.52 |  | $^2$JA, B=14.7 Hz |
|  | H-3B | 3.72 | dd; A of ABX System dd; B of ABX System |  |
| Asp | H-2 | 4.71 | dd; X of ABX System | $^3$J2, 3A=9.5 hz; $^3$J2, 3B=4.3 Hz |
|  | H-3A | 2.62 |  | $^2$JA, B=16.1 Hz |
|  | H-3B | 2.81 | dd; A of ABX System dd; B of ABX System |  |
| Cys | H-2 | 4.3 | dd; X of ABX System | $^3$J2, 3A=5.5 hz; $^3$J2, 3B=4.4 Hz |
|  | H-3A | 2.85 |  | $^2$JA, B=14.1 Hz |
|  | H-3B | 2.89 | dd; A of ABX System dd; B of ABX System |  |

Scheme 2[a]

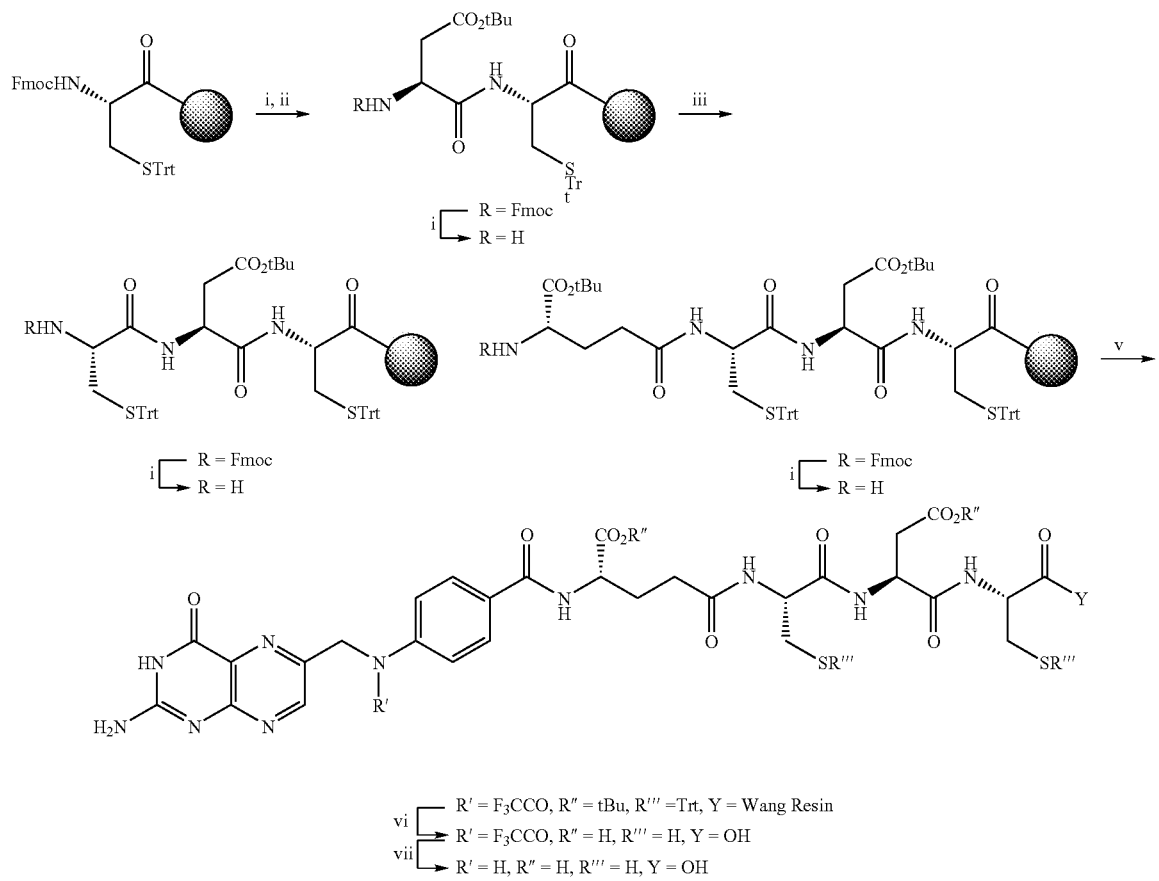

[a]Reagents and conditions: i) 20% Piperidine, DMF; ii) Fmoc-Asp(OtBu)-OH, PyBop, DIPEA, DMF; iii) Fmoc-Cys(Trt)-OH, PyBop, DIPEA, DMF; iv) Fmoc-D-Glu-OtBu, PyBop, DIPEA, DMF; v) N[10]-TFA-Pte-OH, DIPEA, DMSO; vi) TFAA, HSCH$_2$CH$_2$SH, iPr$_3$SiH; vii) H$_4$NOH, pH = 10.3.

EXAMPLE 3

Preparation of the Non-Radioactive Reagent Vial and of $^{99m}$Tc-EC20.

EC20 kits were used for preparation of the $^{99m}$Tc-EC20 radioactive drug substance. Each kit contained a sterile, non-pyrogenic lyophilized mixture of 0.1 mg EC20, 80 mg sodium α-$_D$-glucoheptonate, 80 mg tin (II) chloride dihydrate, and sufficient sodium hydroxide or hydrochloric acid to adjust the pH to 6.8±0.2 prior to lyophilization. The lyophilized powder was sealed in a 5 mL vial under an argon atmosphere. The kits were then stored frozen at −20° C. until use or expiration (current shelf life is >2 years). Importantly, the tin (II) chloride component is required to reduce the added $^{99m}$Tc-pertechnetate, while the sodium α-$_D$-glucoheptonate component is necessary to stabilize the newly reduced $^{99m}$Tc prior to its final chelation to the EC20 compound.

$^{99m}$Tc-EC20 was prepared as follows (i.e., chelation of $^{99m}$Tc to EC20). First, a boiling water bath containing a partially submerged lead vial shield was prepared. The top of an EC20 vial was swabbed with 70% ethanol to sanitize the surface and the vial was placed in a suitable shielding container. Using a shielded syringe with 27-gauge needle, 1 mL of sterile Sodium Pertechnetate $^{99m}$Tc Injection (15 to 20 mCi) in 0.9% sodium chloride was injected into the shielded vial. Before removal of the syringe from the vial, a volume of gas from the vial equal to the volume of pertechnetate added was withdrawn in order to normalize the pressure inside the vial. The vial was gently swirled for 30 seconds to ensure complete dissolution of the lyophilized powder. The vial was then placed into the lead shield that was standing in the boiling water bath. The solution was heated for ~18 minutes and then cooled to room temperature for a minimum of 15 min. This solution can be stored at room temperature (15–25° C.) protected from light, but it should be used within 6 hours of preparation.

The radiochemical stability of the radioactive drug substance was determined by HPLC after storing at room temperature protected from light for up to 24 hours. Samples of the $^{99m}$Tc-EC20 solution (20 μL) were analyzed using an HPLC system consisting of a Waters 600E Multisolvent Delivery System and 490 UV detector, a Bioscan EC-3200 radiodetector, Laura v1.5 radiochromatogram software, and a Waters Nova-Pak C18 (3.9×150 mm) column. Injected samples were eluted isocratically using an aqueous mobile phase containing 20% methanol and 0.1% trifluoroacetic acid at a flow rate of 1 mL/min. The HPLC analysis was monitored with both the UV detector (280 nm) and the gamma radiodetector. Notably, the radiochemical purity of $^{99m}$Tc-EC20 remained greater than 90% for at least 24 hours in all cases.

EXAMPLE 4

Determination of Radiochemical Purity of $^{99m}$Tc-EC20 by TLC.

The major radiochemical impurities in the preparation of $^{99m}$Tc-EC20 will be 1) $^{99m}$Tc pertechnetate, 2) $^{99m}$Tc-glucoheptonate (ligand exchange precursor), 3) non-specific binding $^{99m}$Tc ($^{99m}$Tc bound at a site other than the expected Dap-Asp-Cys chelating moiety of the EC20 molecule), and 4) hydrolyzed $^{99m}$Tc. Since $^{99m}$Tc-EC20 was being tested for possible clinical use, a three-TLC-based method was developed to determine the amounts of each impurity and to estimate the overall radiochemical purity of $^{99m}$Tc-EC20.

In the first system a cellulose plate was developed with deionized water. $^{99m}$Tc-EC20, $^{99m}$Tc-glucoheptonate, non-specific binding $^{99m}$Tc and $^{99m}$Tc pertechnetate move to the solvent front ($R_f$=1.0), while hydrolyzed $^{99m}$Tc remains at the origin ($R_f$=0.0). The cellulose plate was cut into two pieces at $R_f$=0.3 (1.5 cm from origin) and each piece was counted using a dose calibrator. The percent of hydrolyzed $^{99m}$Tc was calculated as follows: A=% Hydrolyzed; $^{99m}$Tc= (µCi in bottom piece/µCi in both pieces)×100.

In the second system, a cellulose plate was developed with acetone and 0.9% NaCl (7:3, v/v). $^{99m}$Tc-pertechnetate moves with $R_f$=0.9, while $^{99m}$Tc-EC20, $^{99m}$Tc-glucoheptonate, non-specific binding $^{99m}$Tc and hydrolyzed $^{99m}$Tc remain at the origin ($R_f$=0.0). The cellulose/acetone-saline plate was cut into two pieces at $R_f$=0.6 (3.0 cm from the origin) and each piece was counted using a dose calibrator. The percent of $^{99m}$Tc-pertechnetate was calculated as follows: B=% $^{99m}$Tc-pertechnetate=(µCi in top piece/µCi in both pieces)=100.

Finally, in the third system a DEAE ion exchange plate was developed with 0.3 M Na$_2$SO$_4$. $^{99m}$Tc-glucoheptonate moves to the solvent front ($R_f$=1.0), nonspecific binding $^{99m}$Tc moves with $R_f$=0.6, and $^{99m}$Tc~EC20, hydrolyzed $^{99m}$Tc and $^{99m}$Tc-pertechnetate remain near the origin ($^{99m}$Tc-EC20. $R_f$=0.1; hydrolyzed $^{99m}$Tc: $R_f$=0.0; $^{99m}$Tc pertechnetate: $R_f$=0.3). The cellulose/Na$_2$SO$_4$ plate was cut into two pieces at 2.5 cm from the origin and each piece was counted using a dose calibrator. The percent of $^{99m}$Tc-glucoheptonate and non-specific binding $^{99m}$Tc were calculated as follows: C=%($^{99m}$Tc-Glucoheptonate+non-specific binding $^{99m}$Tc)=(µCi in top piece/µCi in both pieces)=100. The overall radiochemical purity of $^{99m}$Tc-EC20 was then calculated as follows: Radiochemical purity=100−(A+B+C).

Figure 2:
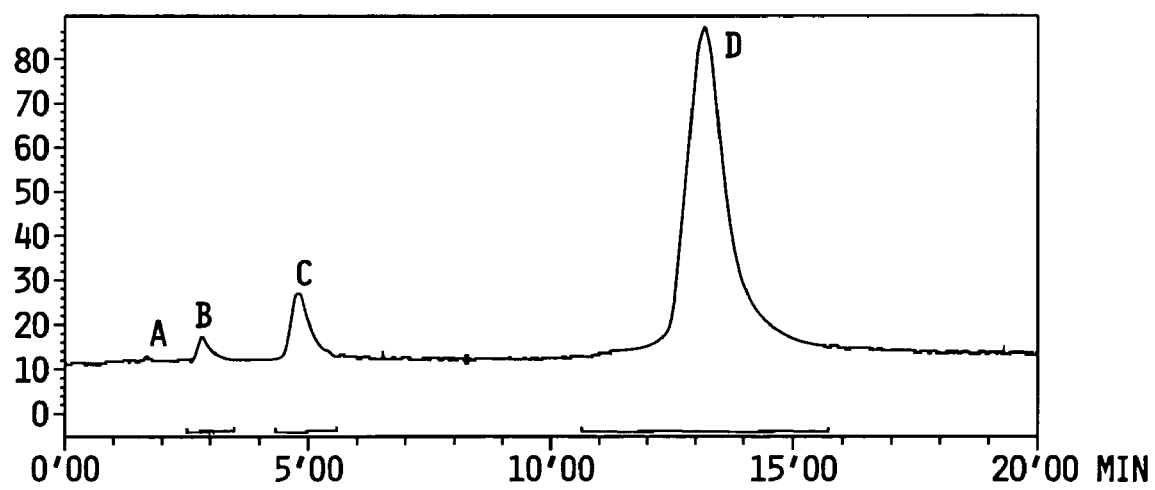
FIG. 2. HPLC radiochromatogram of $^{99m}$Tc-EC20. Samples of $^{99m}$Tc-EC20 were eluted isocratically on a Waters Nova-Pak C18 (3.9×150 mm) column using an aqueous mobile phase containing 20% methanol and 0.2% trifluoroacetic acid at a flow rate of 1 mL/min. The HPLC analysis was monitored with both the UV detector (280 nm) and a Bioscan FC-3200 radiodetector. Peak A, free $^{99m}$Tc; Peak B, a folate-containing chelate of unknown structure; Peaks C and D, diastereomers possessing either a syn or anti configuration of the technetium-oxygen bond in the Dap-Asp-Cys chelating ring of EC20.

As shown in FIG. 2, HPLC analysis of the $^{99m}$Tc-EC20 formulation shows four radiochemical components, designated as Peaks A through D. Peak A was confirmed to be free $^{99m}$Tc and this by-product is reproducibly present at <2%. Peak B, which was different from that of $^{99m}$Tc-glucoheptonate (data not shown) eluted with a retention time of 2.8 min. This component represented about 3% of the mixture and was thought to result from $^{99m}$Tc chelating at some other site on the EC20 molecule besides the expected Dap-Asp-Cys moiety. Peaks C and D (retention times of 4.8 minutes and 13.2 minutes, respectively), account for the majority of the formulated radiochemical activity.

EXAMPLE 5

Synthesis of Re-EC20.

Fifty-two mg (0.010 mmol) of EC20 and [ReO$_2$(en)$_2$]Cl (52 mg, 0.14 mmol) were dissolved in 6 mL and 1 mL argon-purged phosphate buffer (0.05 M, pH 5.8), respectively. The two solutions were combined and heated under an argon atmosphere in a boiling water bath for 2 hours. The reaction mixture was frozen and lyophilized overnight. The crude product was purified by HPLC (Xterra RPI8 column, 19×150 mm, 10 mM NH$_4$OAc/CH$_3$CN, flow rate 10 mL/mm; gradient 1% to 8%). The fractions were collected, lyophilized and stored at −20° C. until use.

Figure 3:
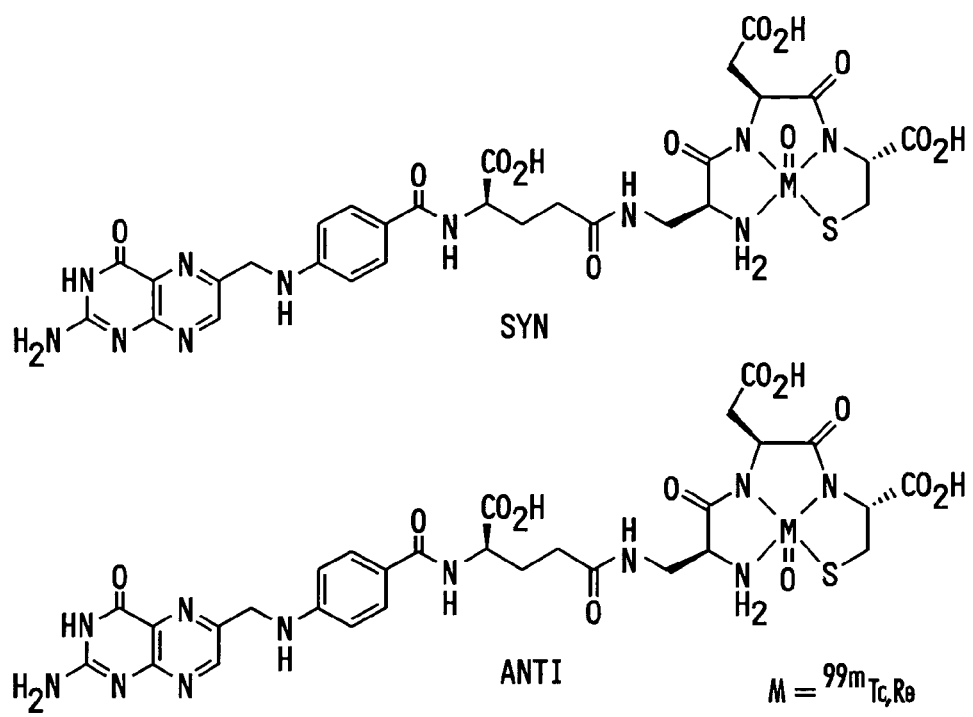
FIG. 3. Structures of Re-EC20 and $^{99m}$Tc-EC20 isomers (syn or anti position of metal-oxo bond).

Because no mass spectral facilities were available for analysis of radioactive materials, the non-radioactive rhenium analog, Re-EC20, was analyzed. Both rhenium and technetium are Group VIIA metals that have significant similarity in physical and chemical properties. They also form similar complexes with organic ligands. This analogous chemical behavior has been frequently used in structure elucidation of new classes of technetium radiopharmaceuticals based on non-radioactive rhenium analogues. Interestingly, HPLC analysis of Re-EC20 also showed two major peaks eluting at 5 and 14.2 minutes, respectively, similar to Peaks C and D for $^{99m}$Tc-EC20 (chromatogram not shown). Mass spectral analysis confirmed that these two components were isomers corresponding to the Re-EC20 complex (m/z=945). In fact, these species were likely diastereomers possessing either a syn or anti configuration of the technetium-oxygen bond in the Dap-Asp-Cys chelating ring, as depicted in FIG. 3. Because i) the two peaks in the Re-EC20 chromatogram represent isomeric complexes, and ii) reports of similar isomerism in technetium complexes exist, it is likely that components C and D in the $^{99m}$Tc-EC20 radiochromatogram are also isomers.

EXAMPLE 6

Cell Culture.

Cells were grown continuously as a monolayer using folate-free RPMI medium (FFRPMI) containing 10% heat-inactivated fetal calf serum (HIFCS) at 37° C. in a 5% CO$_2$/95% air-humidified atmosphere with no antibiotics. The HIFCS contained its normal complement of endogenous folates which enabled the cells to sustain growth in this more physiologically-relevant medium. All cell experiments were performed using FFRPMI containing 10% HIFCS (FFRPMI/HIFCS) as the growth medium, except where indicated.

EXAMPLE 7

Relative Affinity Assay.

The relative affinity of various folate derivatives was determined according to the method described by Westerhoff et al. (Mol. Pharm., 48: 459–471 (1995)) with slight modification. Briefly, FR-positive KB cells were gently trypsinized in 0.25% trypsin/PBS at room temperature for 3 minutes and then diluted in FFRPMI/HIFCS. Following a 5 min 800×g spin and one PBS wash, the final cell pellet was suspended in FFRPMI 1640 (no serum). Cells were incubated for 15 min on ice with 100 nM of $^3$H-folic acid in the absence and presence of increasing concentrations of folate-containing test articles. Samples were centrifuged at 10,000×g for 5 min, cell pellets were suspended in buffer, were transferred to individual vials containing 5 mL of scintillation cocktail, and were then counted for radioactivity. Negative control tubes contained only the $^3$H-folic acid in FFRPMI (no competitor). Positive control tubes contained a final concentration of 1 mM folic acid, and CPMs measured in these samples (representing non-specific binding of label) were subtracted from all samples. Notably, relative affinities were defined as the inverse molar ratio of compound required to displace 50% of $^3$H-folic acid bound to KB FR, and the relative affinity of folic acid for the FR was set to 1.

The capacity of EC20 to directly compete with folic acid for binding to cell surface FRs was measured using this assay. Importantly, a relative affinity value of 1.0 implies that the test article ligand has an affinity for the FR equal to folic acid. Likewise, values lower than unity reflect weaker affinity, and values higher than unity reflect stronger affinity.

Figure 4:
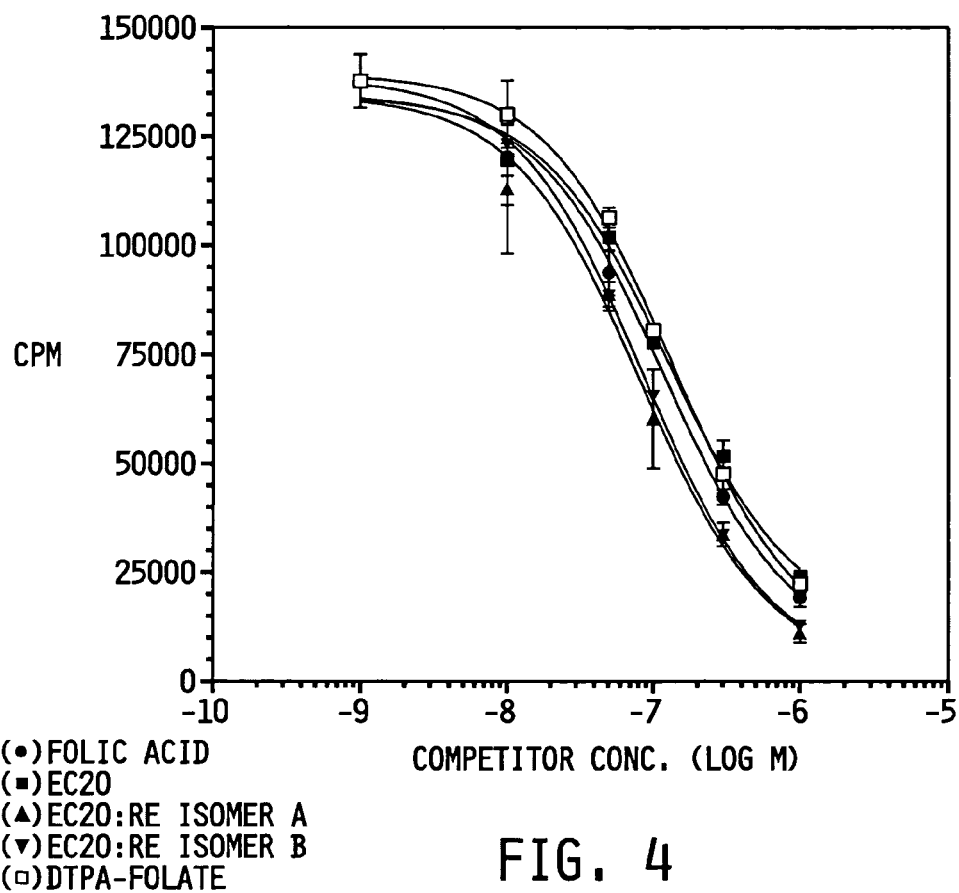
FIG. 4. Blocking of $^3$H-folic acid binding to KB cells with various folate-containing competitors. KB cells were incubated for 15 min on ice with 100 nM $^3$H-folic acid in the presence and absence of increasing competitor concentrations. (●) Folic acid; (■) EC20; (▲) EC20:Re isomer A; (▼) EC20:Re isomer B; (□) DTPA-Folate. Error bars represent 1 standard deviation (n=3).

Cultured KB cells were incubated with 100 nM $^3$H-folic acid in the presence of increasing concentrations of non-radioactive folic acid, EC20, Rhenium-EC20 (isomer A; Peak C), Rhenium-EC20(isomer B; peak 0), or a related folate-based radiopharmaceutical, DTPA-folate. Following a 15-minute incubation at 4° C., cells were rinsed free of unbound material and counted for residual cell-associated radioactivity. The quantity of bound radioactivity was plotted against the concentration of unlabeled ligand, and IC$_{50}$ values (concentration of ligand required to block 50% of $^3$H-folic acid binding) were estimated. As shown in FIG. 4 and Table 2 (below), EC20 was determined to have an affinity of 0.92 relative to that of folic acid for human FRs. Both isomers of Rhenium-EC20 displayed relative affinity values that were very similar to, if not better than, the parent EC20 molecule (1.42 and 1.37 for Re-EC20 isomer A and isomer B, respectively). DTPA-folate, an $^{111}$In-chelating folate radiopharmaceutical agent, displayed a relative affinity of 0.87 for the folate receptor. Thus, chemical modification of folate with various metal chelating motifs did not disturb the vitamin's intrinsic affinity for the FR.

Table 2. Relative Affinity Estimations. Relative affinities (RA) were defined as the inverse molar ratio of compound required to displace 50% of $^3$H-folic acid bound to FR-positive KB cells. The relative affinity of folic acid was set to 1. Each test article was evaluated in triplicate.

| Test Article | IC$_{50}$ (nM) | S.D. | RA | S.D. |
|---|---|---|---|---|
| Folic Acid | 118 | ±19 | 1.00 | |
| EC20 | 128 | ±25 | 0.92 | ±0.23 |
| EC20:Re isomer 1 | 83 | ±16 | 1.42 | ±0.36 |
| EC20:Re isomer 2 | 86 | ±3 | 1.37 | ±0.23 |
| DTPA-Folate | 136 | ±12 | 0.87 | ±0.16 |

EXAMPLE 8

Time-Dependent Cell Uptake.

KB cells were seeded in 12-well Falcon plates and allowed to form sub-confluent monolayers overnight. Following one rinse with 1 mL of fresh FFRPMI/HIFCS, each well received 1 mL of FFRPMI/HIFCS containing 10 nM $^{99m}$Tc-EC20. Cells were incubated for predetermined times at 37° C. and then rinsed four times with 1 mL of ice-cold PBS, pH 7.4. The cell monolayers were dissolved in 0.5 mL of PBS, pH 7.4 containing 1% sodium dodecyl sulfate for 15 min at room temperature and then counted for radioactivity using a Packard gamma counter. The protein in each sample was quantitated using a BioRad DC Protein Assay kit, and cellular protein values were converted to cell number using the conversion factor of 2.23×10$^{-7}$ mg protein per cell. Final tabulated values were expressed in terms of molecules of EC20 per cell.

Figure 5:
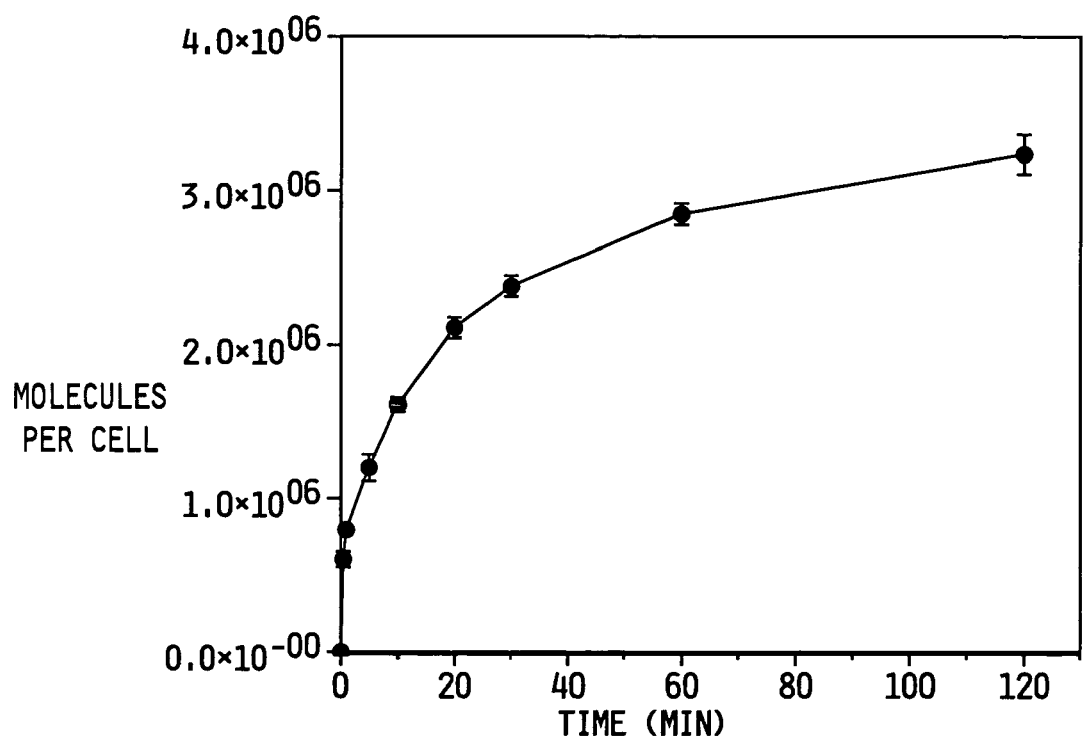
FIG. 5. Time-dependent association of $^{99m}$Tc-EC20. KB cells were incubated with 10 nM $^{99m}$Tc-EC20 for increasing periods of time at 37° C. Following multiple washes, cells were harvested and counted for associated radioactivity. Error bars represent 1 standard deviation (n=3).

The kinetics of $^{99m}$Tc-EC20 uptake into FR-positive KB cells was quantitatively measured using this protocol. As shown in FIG. 5, steady-state uptake was reached within two hours at 37° C., where approximately 3.2 million molecules of EC20 were cell-associated, whereas half-maximal cell association occurred 9 minutes after mixing 10 nM of this radiopharmaceutical with the cells. Interestingly, the half-maximal saturation point was reached in only 37 seconds when cells were incubated with a 10-fold higher concentration of $^{99m}$Tc-EC20 (100 nM; data not shown).

EXAMPLE 9

Concentration-Dependent Cell Uptake.

KB cells were seeded in 12-well Falcon plates and allowed to form sub-confluent monolayers overnight. Following one rinse with 1 mL of fresh FERPMI/HIFCS, each well received 1 mL of FFRPMI/HIFCS containing increasing concentrations of $^{99m}$Tc-EC20. Cells were incubated for 2 hours at 37° C. and then rinsed four times with 1 mL of ice-cold PBS, pH 7.4. The monolayers were dissolved in 0.5 mL of PBS, pH 7.4 containing 1% sodium dodecyl sulfate for 15 min at room temperature and then counted for radioactivity using a Packard gamma counter. Protein content was determined as described above, and final tabulated values were expressed in terms of molecules of EC20 per cell.

Figure 6:
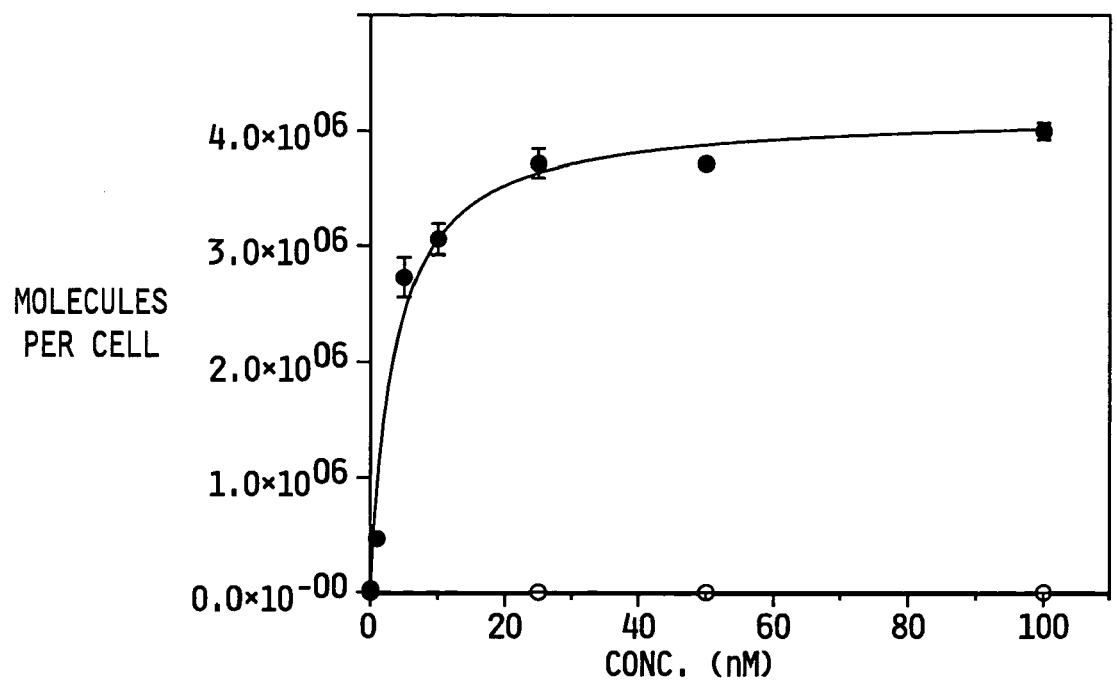
FIG. 6. Concentration-dependent association of $^{99m}$Tc-EC20. KB cells were incubated for 2 hr at 37° C. in the presence of increasing concentrations of $^{99m}$Tc-EC20. Following multiple washes, cells were harvested and counted for associated radioactivity. Error bars represent 1 standard deviation (n=3).

As shown in FIG. 6, the cell uptake of $^{99m}$Tc-EC20 was found to be dependent on the extracellular concentration. The particular KB cells used were determined to bind a maximum of four million molecules of the folate radiopharmaceutical per cell. Scatchard analysis of the data estimated the K$_D$ of binding to be 3.2 nM, a value comparable with the K$_D$ observed for the vitamin folate binding to these same cells.

Figure 7:
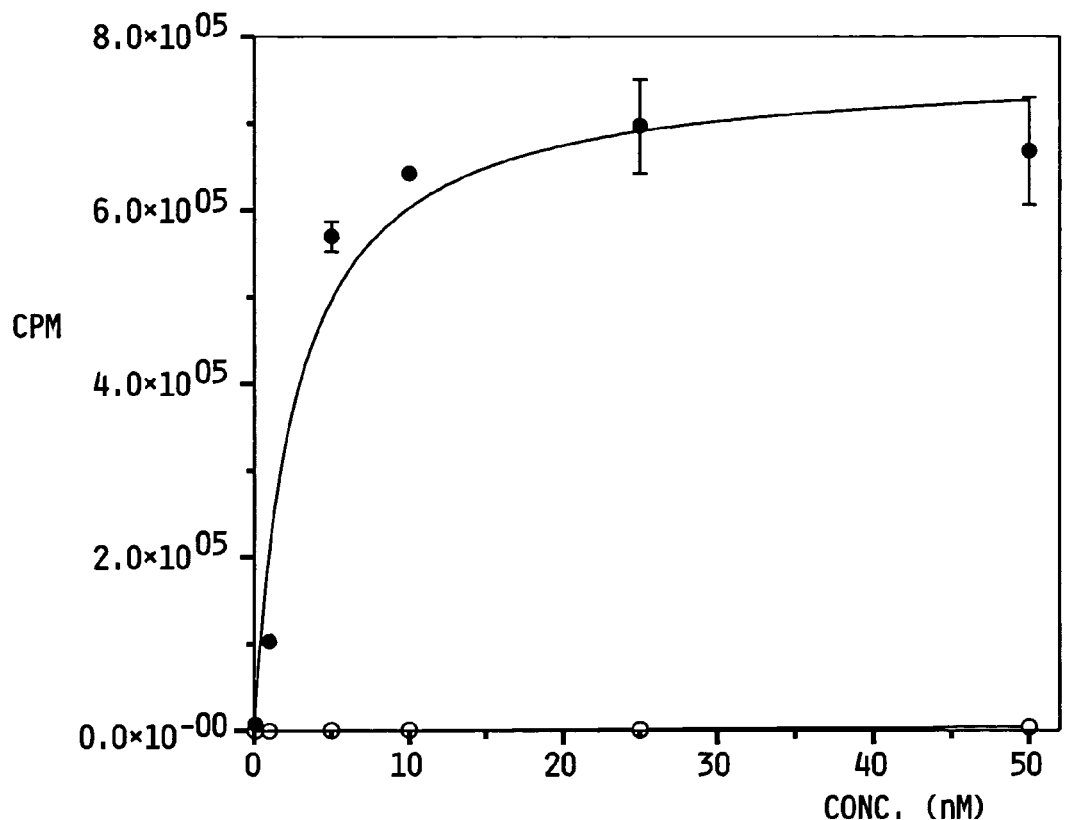
FIG. 7. Concentration-dependent association of $^{99m}$Tc-EC20 "peak B." KB cells were incubated for 2 hr at 37° C. in the presence of increasing concentrations of "Peak B" that was chromatographically isolated from the $^{99m}$Tc-EC20 formulation. Following multiple washes, cells were harvested and counted for associated radioactivity. Error bars represent 1 standard deviation (n=3). (●), Peak B; (○), Peak B plus 1 mM folic acid.

Although the full identity of the Peak B component was not established, UV absorption analysis indicated that it contained a folate moiety (i.e., the absorption spectrum contained folate's signature secondary absorption peak at 363 nm). This HPLC-purified radiolabeled material (Peak B material) was collected and then added to cultured KB cells. As shown in FIG. 7, the cell uptake of the $^{99m}$Tc-labeled Peak B component was also found to be dependent on the extracellular concentration. Scatchard analysis of the data estimated the K$_D$ of binding to be 1.1 nM. Interestingly, the cell association of Peak B was completely blocked in the presence of excess folic acid, indicating that this minor formulation by-product is also capable of targeting FR-positive cells for radiodiagnostic purposes.

EXAMPLE 10

Blood Clearance.

Animals used for this study were maintained on a folate-free diet (Harlan #TD-90261) for approximately three weeks prior to dose administration. Acclimation to this special diet is essential because regular rodent diets contain large amounts of folic acid (6 mg/kg chow) and promote high serum folate levels in mice. Furthermore, previous studies have shown that mice placed on a folate-free diet for 3 weeks had maintained a safe serum folate level of 25±7 nM, which is slightly higher than the 9–14 nM concentration measurable in human serum.

The $^{99m}$Tc-EC20 solution was prepared on the day of use and had initially contained 100 μg of EC20 per milliliter. The solution was further diluted with sterile saline to prepare working stock solutions. The radiochemical purity of the product was estimated to be ~94% by TLC. Each animal received a dose of 50 µg/kg EC20 (67 nmol/kg) in approximately 0.1 mL volume i.v. via the tail vein during brief diethyl ether anesthesia. At the designated times (see FIG. 8) post-injection, each animal was euthanized by $CO_2$ asphyxiation, and blood was immediately collected by cardiac puncture.

Figure 8:
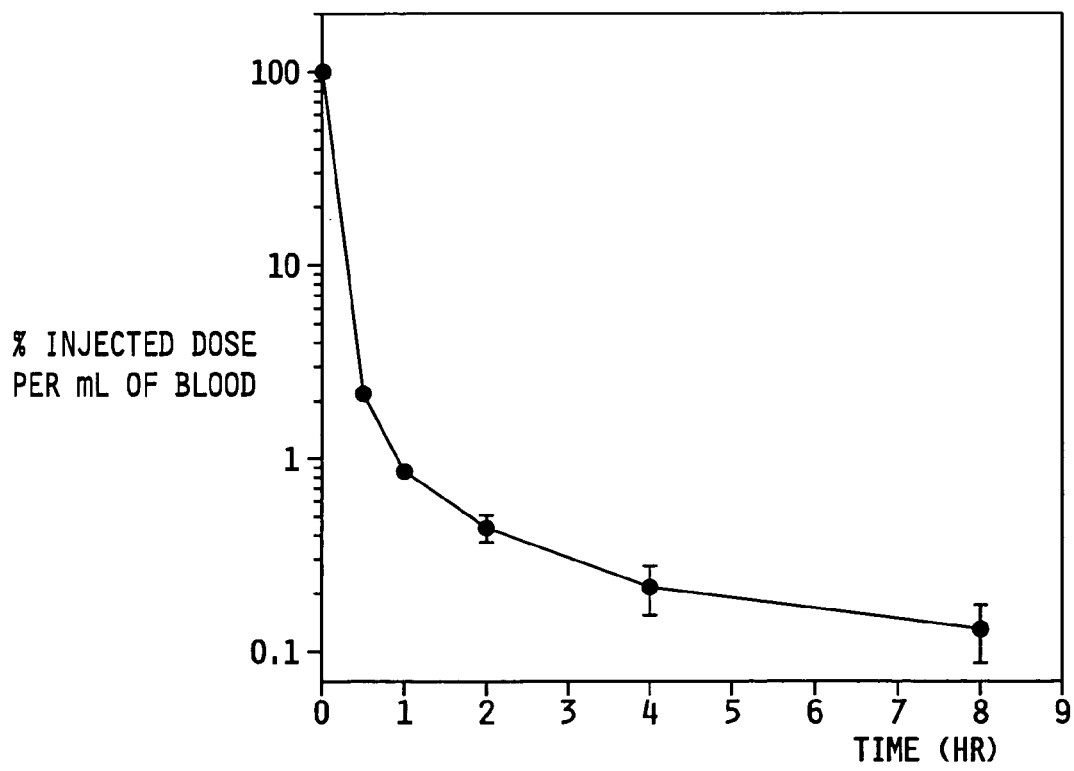
FIG. 8. Blood clearance of $^{99m}$Tc-EC20 in Balb/c mice. Each animal received an intravenous dose of 50 μg/kg EC20 (67 nmol/kg) in approximately 0.1 mL during brief diethyl ether anesthesia. At the designated times post-injection, each animal was euthanized by $CO_2$ asphyxiation, blood was collected and counted for associated radioactivity. Error bars represent 1 standard deviation (n=3 animals).

As shown in FIG. 8, $^{99m}$Tc-EC20 was rapidly removed from circulation in the Balb/c mouse. The plasma half life of this radiopharmaceutical was estimated to be ~4 minutes, and less than 0.2% of the injected $^{99m}$Tc-EC20 dose remained in circulation after four hours (assuming that blood represents 5.5% of the total body mass). This data indicates that folate conjugates are rapidly removed from circulation following intravenous administration, and that valuable tissue biodistribution data can be obtained after only a few hours post-injection without the concern for non-specific tissue uptake due to blood-borne radioactivity.

EXAMPLE 11

Tissue Distribution Studies.

The ability of $^{99m}$Tc-EC20 to target tumors in vivo was assessed using a FR-positive M109 model. These tumor cells are syngeneic for the Balb/c mouse, and they reproducibly form subcutaneous solid tumors within two weeks post inoculation. $^{99m}$Tc-EC14, which is structurally similar to $^{99m}$Tc-EC20 except it contains one additional $_D$-Glu residue (i.e., Pte-$_D$-Glu-$_D$-Glu-βDpr-Asp-Cys), $^{99m}$Tc-EC28(a non-pteroate containing control consisting of benzoyl-$_D$-Glu-$_D$-Glu-βDpr-Asp-Cys), and the previously reported $^{111}$In-DTPA-folate radiopharmaceutical were also evaluated in this bioassay. Importantly, the $^{99m}$Tc-EC28 control agent will not bind to cell surface FRs because it lacks an essential pteridine ring moiety.

Four to five week-old mice (Balb/c strain) were purchased from Harlan Sprague Dawley, Inc. (Indianapolis, Ind.) and were maintained on a folate-free diet for a total of three weeks prior to the experiment. Syngeneic, FR-positive M109 tumor cells (1×10$^6$ per animal) were inoculated in the subcutis of the right axilla two weeks prior to the experiment. All mice were females, and the tumor weights were 54.2±29.8 mg on the day of this experiment. A stock $^{99m}$Tc-EC20 solution containing 100 µg of agent per milliliter was prepared on the day of use, and its radiochemical purity was >96%. The two additional $^{99m}$Tc-chelating agents, $^{99m}$Tc-EC14 and $^{99m}$Tc-EC28 as well as $^{111}$In-DTPA-folate were also prepared to >90% radiochemical purity. All solutions were diluted with either saline alone or a saline solution containing 100 equivalents of folic acid (for competition) such that the final radiopharmaceutical concentration was 10 µmol/mL.

Animals received an approximate 40 µmol/kg i.v. dose of test article in 100 µL volume via a lateral tail vein during brief diethyl ether anesthesia. Four hours post-injection, animals were sacrificed by $CO_2$ asphyxiation, and dissected. Selected tissues were removed, weighed, and counted to determine $^{99m}$Tc distribution. CPM values were decay-corrected, and results were tabulated as % injected dose per gram of wet weight tissue.

As shown in Table 3 (below), the three "folate" containing radiopharmaceuticals, $^{99m}$Tc-EC14, $^{99m}$Tc-EC20 and $^{111}$In-DTPA-Folate, predominantly accumulated in the FR-positive tumor and kidneys, however the kidneys concentrated a higher percent injected dose per gram of tissue (% ID/g) than did the tumor. Interestingly, the net tumor accumulation of $^{111}$In-DTPA-Folate and $^{99m}$Tc-EC20 was nearly the same (19 and 17% ID/g, respectively), whereas the tumor uptake of $^{99m}$Tc-EC14 was somewhat less at ~10% ID/g. Nonetheless, all three agents displayed high tumor to blood ratios (>30 to 1).

TABLE 3

Biodistribution of Folate Radiopharmaceuticals in Balb/c Mice Bearing Subcutaneous M109 Tumors.

% Injected Dose per Gram Tissue (4 hr post intravenous injection)*

|  | $^{99m}$Tc-EC14 | $^{99m}$Tc-EC14 + Folic acid | $^{99m}$Tc-EC20 | $^{99m}$Tc-EC20 + Folic acid | $^{111}$In-DTPA-Folate | $^{111}$In-DTPA-Folate + Folic acid | $^{99m}$Tc-EC28 |
|---|---|---|---|---|---|---|---|
| Blood | 0.31 ± 0.14 | 0.19 ± 0.07 | 0.34 ± 0.03 | 0.09 ± 0.02 | 0.21 ± 0.10 | 0.09 ± 0.04 | 0.06 ± 0.04 |
| Heart | 2.39 ± 0.64 | 0.08 ± 0.01 | 1.57 ± 0.26 | 0.08 ± 0.01 | 2.57 ± 0.82 | 0.06 ± 0.02 | 0.03 ± 0.01 |
| Lung | 2.08 ± 0.40 | 0.15 ± 0.04 | 2.22 ± 0.63 | 0.31 ± 0.26 | 1.72 ± 0.61 | 0.09 ± 0.2 | 0.05 ± 0.01 |
| Liver | 3.44 ± 2.19 | 1.37 ± 0.98 | 3.56 ± 0.25 | 1.15 ± 0.22 | 5.21 ± 2.63 | 0.81 ± 0.03 | 0.50 ± 0.26 |
| Spleen | 2.68 ± 2.49 | 2.99 ± 1.43 | 0.95 ± 0.15 | 0.38 ± 0.33 | 3.30 ± 2.33 | 1.46 ± 0.73 | 0.60 ± 0.38 |
| Intestine | 1.70 ± 0.55 | 0.32 ± 0.11 | 2.56 ± 0.61 | 2.93 ± 1.49 | 1.87 ± 0.69 | 0.82 ± 0.14 | 0.47 ± 0.19 |
| Kidney | 98.0 ± 40.7 | 5.94 ± 0.52 | 138 ± 12.4 | 5.64 ± 2.13 | 191 ± 79.2 | 3.14 ± 1.96 | 0.62 ± 0.14 |
| Muscle | 0.99 ± 0.28 | 0.09 ± 0.11 | 0.67 ± 0.20 | 0.06 ± 0.02 | 1.19 ± 0.48 | 0.05 ± 0.04 | 0.02 ± 0.01 |
| Stomach | 1.47 ± 0.58 | 0.10 ± 0.03 | 1.45 ± 0.55 | 3.35 ± 5.19 | 1.62 ± 0.65 | 0.25 ± 0.20 | 0.21 ± 0.19 |
| Tumor | 9.83 ± 2.77 | 0.43 ± 0.52 | 17.2 ± 1.02 | 0.45 ± 0.18 | 19.3 ± 5.86 | 0.46 ± 0.42 | 0.11 ± 0.06 |
| Tumor/Blood | 34.1 ± 7.41 | 2.00 ± 2.00 | 51.0 ± 8.20 | 4.70 ± 1.30 | 102 ± 43.4 | 5.00 ± 4.60 | 2.00 ± 0.50 |

*Values shown represent the mean ± s.d. of data from 3 animals.

Folate-specific targeting was further demonstrated by two distinct methods. First, the accumulation of $^{99m}$Tc-EC14, $^{99m}$Tc-EC20 and $^{111}$In-DTPA-folate in the FR-positive tumor and kidneys was effectively blocked (>94%) when these agents were co-administered with a 100-fold excess of folic acid. Second, the $^{99m}$Tc-EC28 control agent failed to appreciably accumulate in the kidneys and tumor. Both observations show that an intact "folate-like" (or pteroate) moiety is required to afford targeted uptake and retention of these radiopharmaceutical agents into FR-positive tissues.

EXAMPLE 12

Gamma Scintigraphy.

M109 tumor cells (1×10$^6$ per animal) were inoculated in the subcutis of the right axilla of Balb/c mice two weeks prior to the experiment. Animals received an approximate 50

μmol/kg i.v. dose of test article in 100 μL volume via a lateral tail vein during brief diethyl ether anesthesia. Four hours post-injection, animals were sacrificed by $CO_2$ asphyxiation and then placed on top of an image acquisition surface. Whole body image acquisition was performed for 1 minute at a count rate of 50–75,000 counts per minute using a Technicare Omega 500 Sigma 410 Radioisotope Gamma Camera. All data were analyzed using a Medasys MS-DOS-based computer equipped with Medasys Pinnacle software.

Uptake of $^{99m}$Tc-EC20 by the FR-positive M109 tumors and kidneys was demonstrated using this gamma scintigraphy protocol. As shown in FIG. 9, a ventral image of a mouse injected with $^{99m}$Tc-EC20 as described above localizes the gamma radiation to the two kidneys (K) and the M109 tumor mass (T; shoulder region). No appreciable radiotracer was observed in other body tissues. A similar image profile has been reported for the $^{111}$In-DTPA-Folate radiopharmaceutical.

EXAMPLE 13

Urinary Excretion and Metabolism.

The urinary HPLC speciation profile of $^{99m}$Tc-EC20 was obtained using Balb/c mice. Mice (~20 g each) were injected with 1 mCi (6.7 nmol) of $^{99m}$Tc-EC20 via a lateral tail vein. Following a 1, 4, or 6 hour time period, groups of two mice were euthanized by $CO_2$ asphyxiation and urine was collected. After filtration through a GV13 Millex filter, the radiochemical speciation was assessed using an HPLC system equipped with a Nova-Pak C18 3.9×150 mm column and a radiochemical detector. The system was isocratically eluted with 20% methanol containing 0.1% TFA at a flow rate of 1 mL/minute.

It was previously determined that the primary elimination route for $^{111}$In-DTPA-Folate was via the urine. Similar to the HPLC profile shown in FIG. 2, both the $^{99m}$Tc-EC20 standard and the urine samples exhibited four radioactive peaks. As shown in Table 4 (below), the radiochemical purity of the standard (sum of peaks C and D presumably corresponding to the syn and anti $^{99m}$Tc-EC20) remained constant at ~93% over the 6 hr duration of this experiment. The amount of free $^{99m}$Tc in the standard (peak A) was ~2%. Importantly, peak B within this radiochemical profile is believed to be EC20 chelated with $^{99m}$Tc at an unconventional, less stable position, however the radioactivity measured in this fraction was not included in the overall radiochemical purity estimation for $^{99m}$Tc-EC20. This data collectively indicates that the formulation remained stable in saline solution throughout this 6 hr investigation.

After 1 and 4 hours post-injection into Balb/C mice, the radiochemical speciation profile of $^{99m}$Tc-EC20 in the mouse urine did not change. The radioactivity present in the urine at 6 hours post-injection, however, was too low to accurately assay by HPLC. The proportion of parent drug among radioactive species recovered in urine remained relatively constant at approximately 90% throughout the four hours during which it could be quantitated. This value is very similar to the 93% purity of the standard indicating that $^{99m}$Tc-EC20 is predominately excreted into the urine in an unmodified form.

TABLE 4

Excretion and Metabolism of $^{99m}$Tc-Ec20 from the Balb/c Mouse. Mice were injected with 1 mCi (6.7 nmol) of $^{99m}$Tc-EC20 via a lateral tail vein. At the indicated times, groups of two mice were euthanized and urine was collected. The radiochemical speciation was then determined by HPLC. The area percent sum of peaks C and D (syn and anti isomers) is used to calculate the overall purity of intact $^{99m}$TC-EC20.

| | | Area Percent | | | | |
|---|---|---|---|---|---|---|
| | | $^{99m}$Tc-EC20 Standard | | | Urine Samples (two mice/timepoint) | |
| Peak | RT (min) | 0 hr | 1 hr | 6 hr | 1 hr | 4 hr |
| A (pertechnetate) | 1.4 | 2 | 2.1 | 1.8 | 8.3  6.3 | 9.4  10.2 |
| B (unknown) | 3.4 | 4.5 | 4.5 | 4.8 | 2.5  2.6 | 5.4  0 |
| C (isomer 1) | 5.5 | 15.5 | 15.7 | 15.9 | 20.4  18.1 | 7.3  11.1 |
| D (isomer 2) | 18.5 | 78 | 77.7 | 77.5 | 68.8  73 | 77.9  78.7 |
| Sum C and D | | 93.5 | 93.4 | 93.4 | 89.2  91.1 | 85.2  89.8 |

EXAMPLE 14

Serum Protein Binding.

Fresh rat serum, and commercial male human serum (type AB donors, Sigma Chemical Co.) were used to evaluate in vitro binding of $^{99m}$Tc~EC20 to serum proteins. One minute after $^{99m}$Tc-EC20 was mixed with 1 mL of serum at room temperature, 0.3 mL of the serum solution was transferred to a clean Amicon Centrifree® ultrafiltration device (30,000 NMWL) in triplicate. Within one minute of loading the centrifuge with the serum solution, the device was spun at 1000×g for 20 minutes at 20° C. 50 μL samples of the original solution, and of the filtrate from each device, was transferred to a clean tube and counted in an automatic gamma counter. A control solution of $^{99m}$Tc~EC20 mixed with 1 mL of normal saline was ultrafiltered in an identical fashion. The percentage of free $^{99m}$Tc was calculated for each of the three samples.

While $^{99m}$Tc-EC20 exhibited only a minor level of non-specific binding to the ultra-filtration device (~5%), approximately 70% of it was found to predominantly associate with the >30 kDa serum protein fraction in solutions of rat or human serum (69% and 72%, respectively). Importantly, since $^{99m}$Tc-EC20 does effectively and preferentially accumulate within FR-positive tissues (see Table 2 and FIG. 8), its apparent affinity for serum proteins does not appear to affect this radiotracer's ability to target FRs in vivo.

EXAMPLE 15

Tissue Distribution Studies.

The protocols used in this example are similar to those described in Example 11. The ability of $^{99m}$Tc-EC20 to target tumors in vivo was further assessed using FR-positive M109 and FR-negative 4T1 tumor models. Six week-old female Balb/c mice (n=3/dose group) were purchased from Harlan Sprague Dawley, Inc. (Indianapolis, Ind.) and were maintained on a folate-free diet (Harlan TEKLAD) for a total of seven days prior to tumor cell inoculation.

Syngeneic, FR-positive M109 tumor cells (2×10$^6$ $P_o$ per animal) or FR-negative 4T1 cells (5×10$^5$ $P_o$ per animal) were inoculated subcutaneously in 100 μl of folate-free RPMI-1640 containing 1% syngeneic mouse serum. A stock $^{99m}$Tc- EC20 solution containing 100 µg of agent per milliliter was prepared on the day of use as described above.

Sixteen days after tumor cell inoculation, the animals were injected intravenously with 500 or 1800 nmoles/kg of EC20 for M109 tumor-bearing animals and 500 nmoles/kg of EC20 for 4T1 tumor-bearing animals (3 mice per dose group). All injections were in 100 µl volumes. Four hours post-injection, animals were sacrificed by $CO_2$ asphyxiation, and blood was collected by cardiac puncture and the animals were dissected. Selected tissues (heart, lungs, liver, spleen, kidney, intestines, stomach, muscle, and tumor) were removed, weighed, and counted in an automatic gamma counter to determine $^{99m}Tc$ distribution. Uptake of the radiopharmaceutical in terms of percentage injected dose of wet weight tissue (% ID/g) was calculated by reference to standards prepared from dilutions of the injected preparation.

Figure 11:
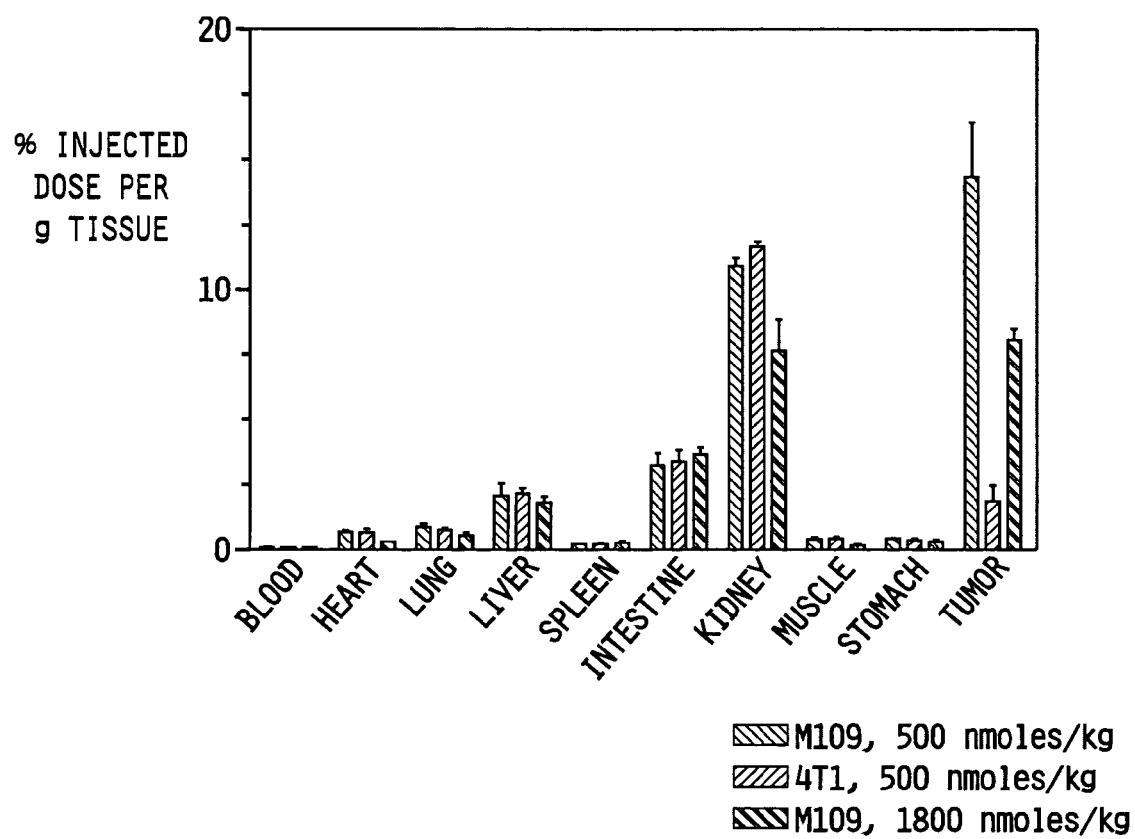
FIG. 11. Tissue distribution of $^{99m}$Tc-EC20 in Balb/c mice bearing FR-postive M109 tumors and FR-negative 4T1 tumors.
Figure 12:
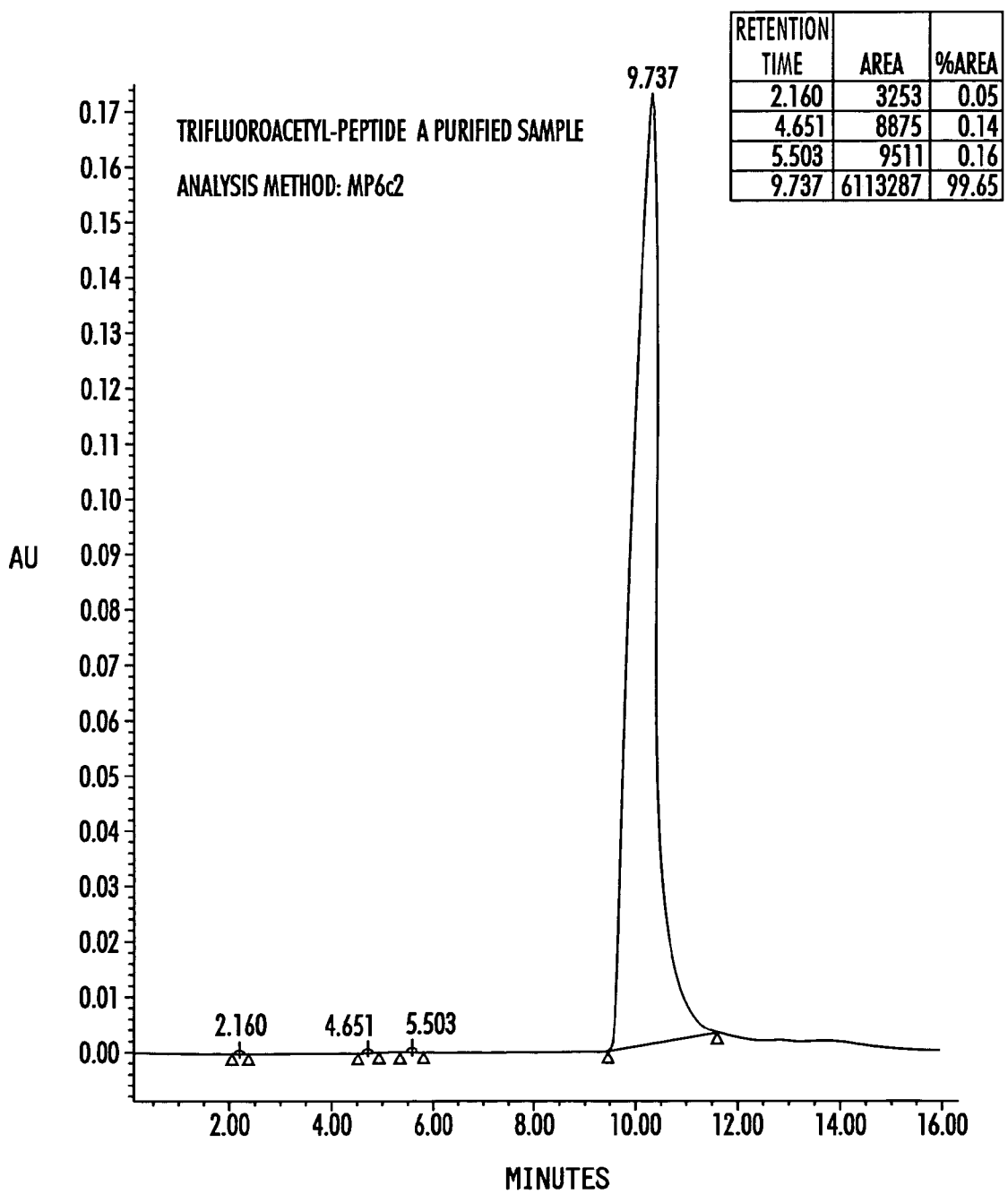
FIG. 12. HPLC analysis of EC11.
Figure 13:
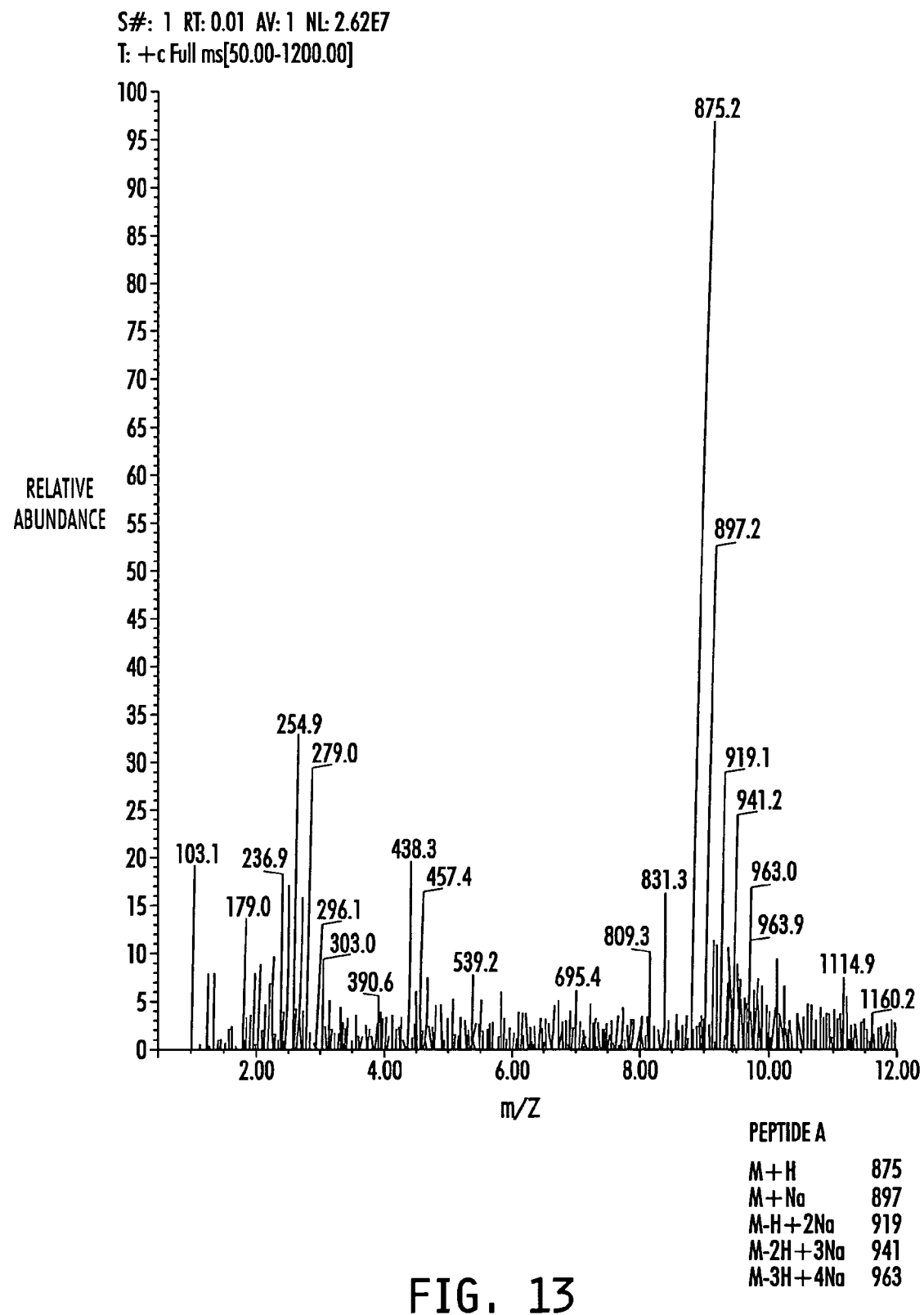
FIG. 13. Mass spectroscopy analysis of EC11.
Figure 14:
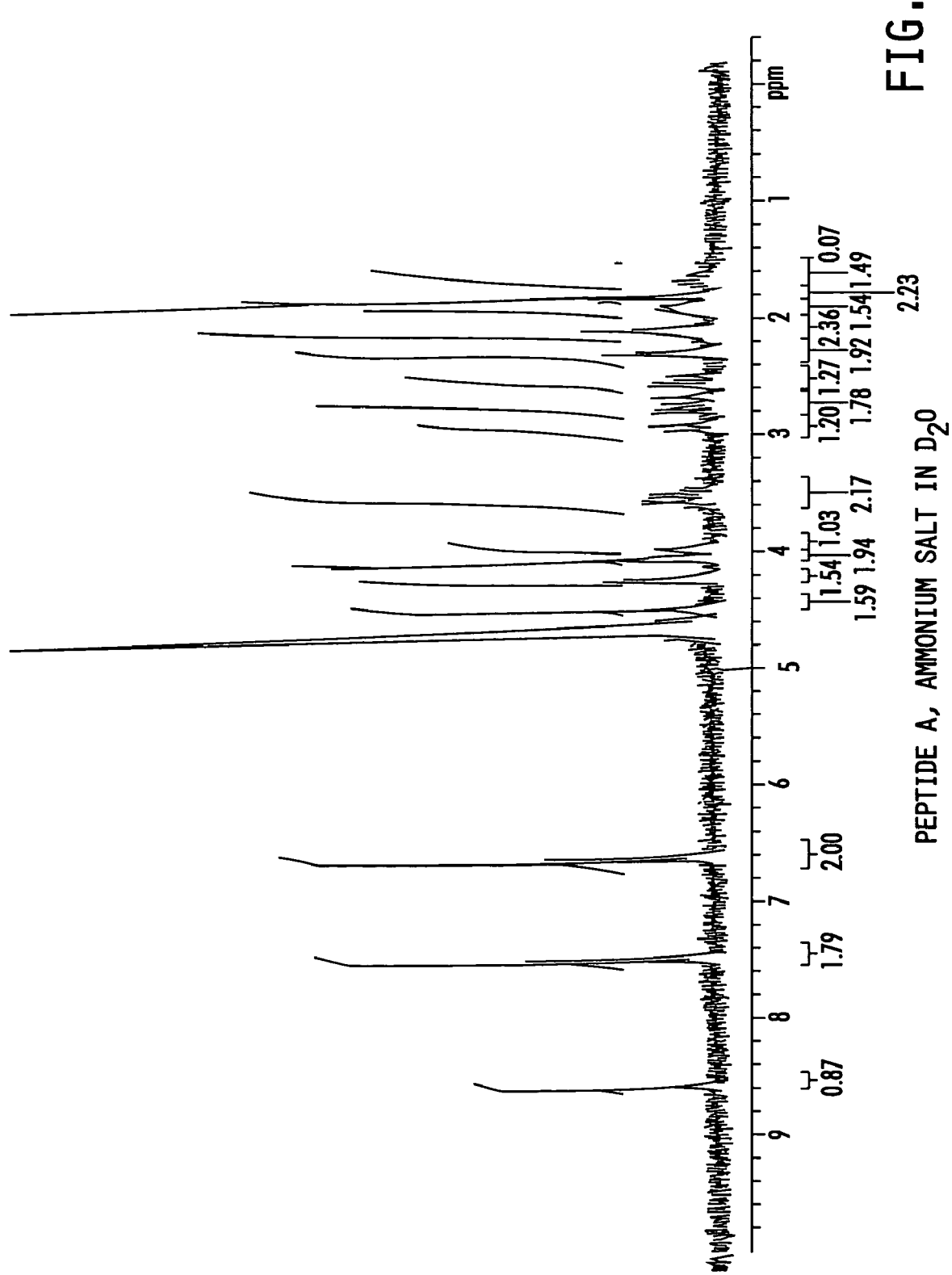
FIG. 14. NMR analysis of EC11.
Figure 15:
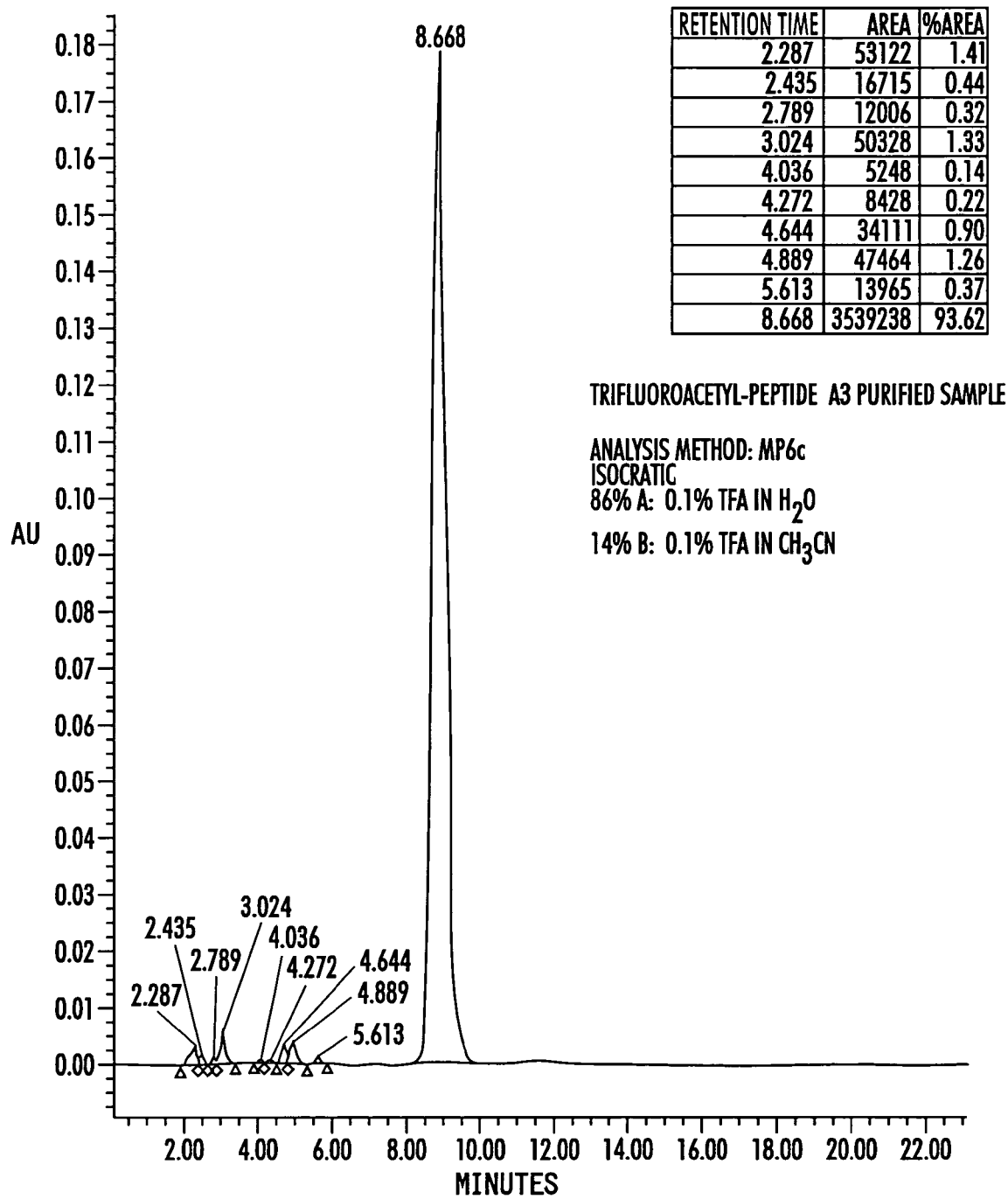
FIG. 15. HPLC analysis of EC13.
Figure 16:
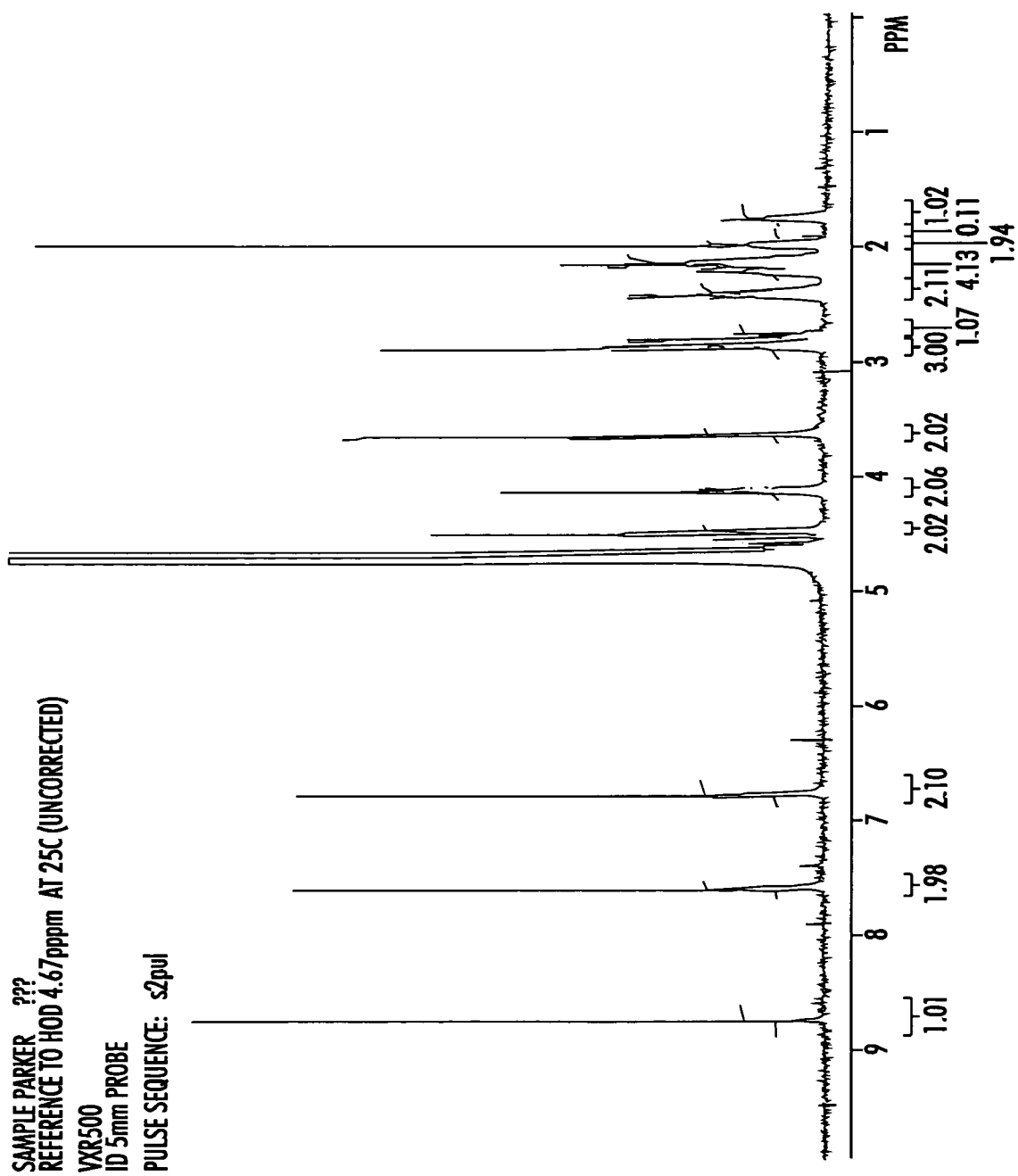
FIG. 16. NMR analysis of EC14.
Figure 17:
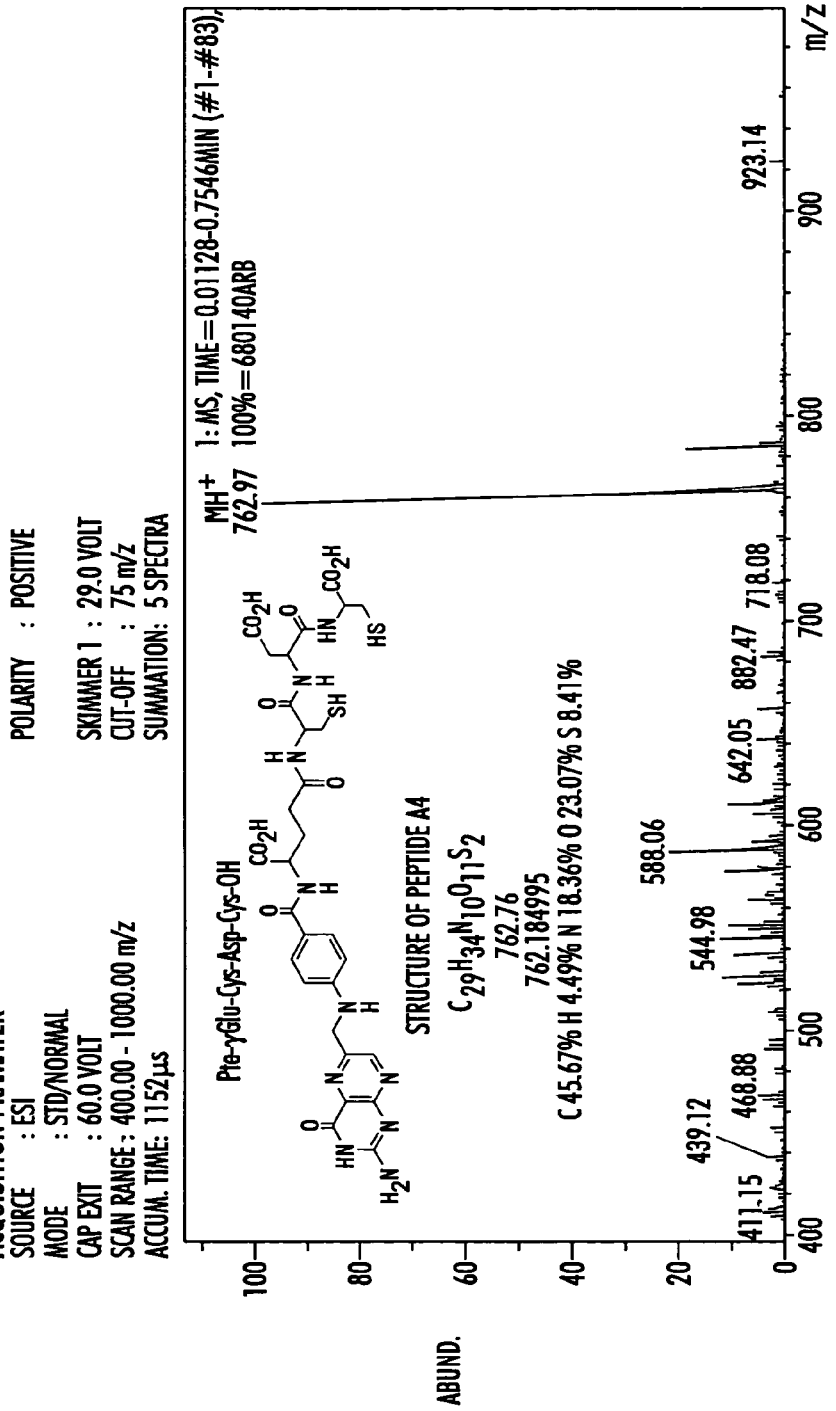
FIG. 17. Mass spectroscopy analysis of EC15.
Figure 19:
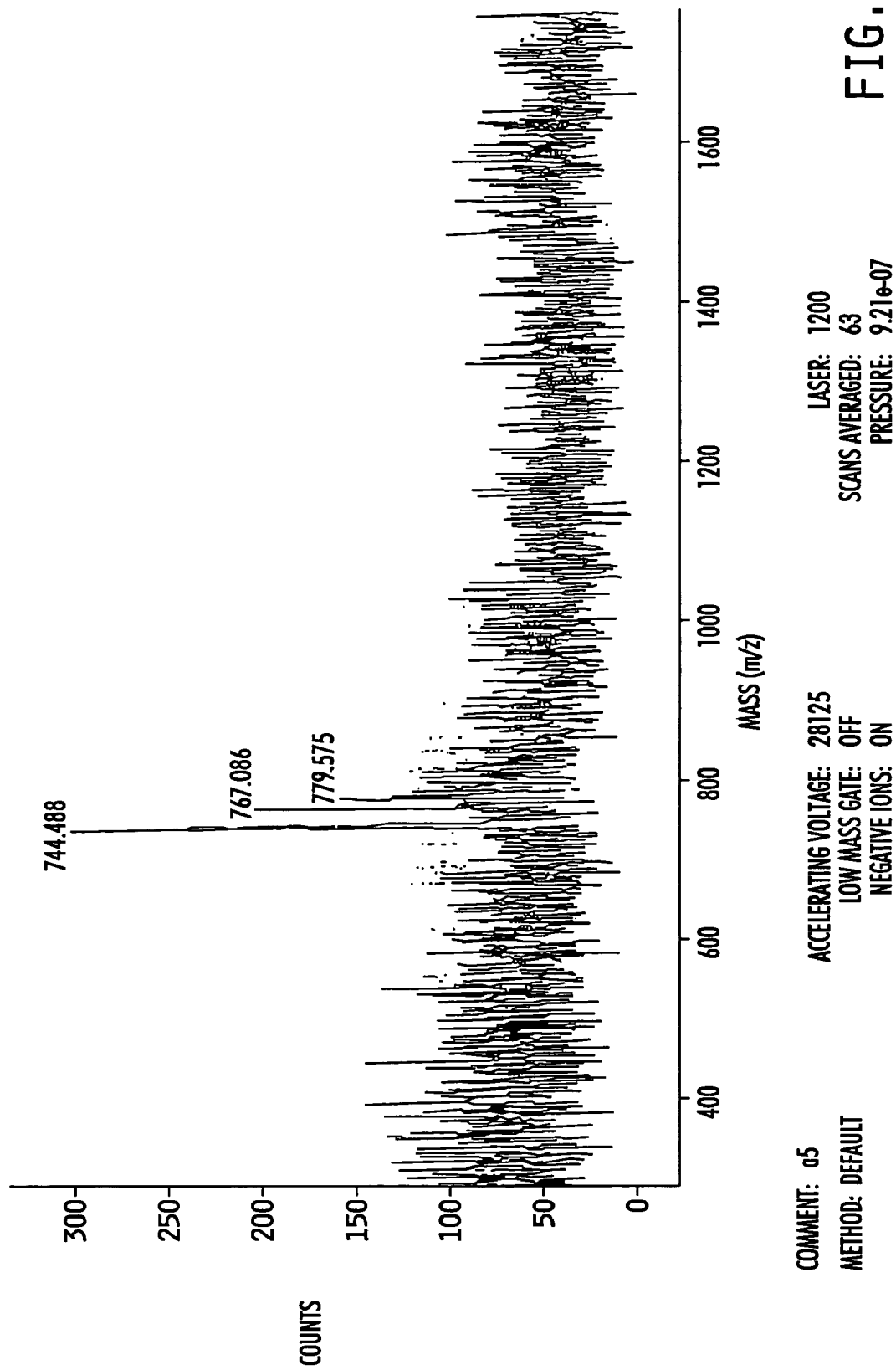
FIG. 19. Mass spectroscopy analysis of EC19.
Figure 20:
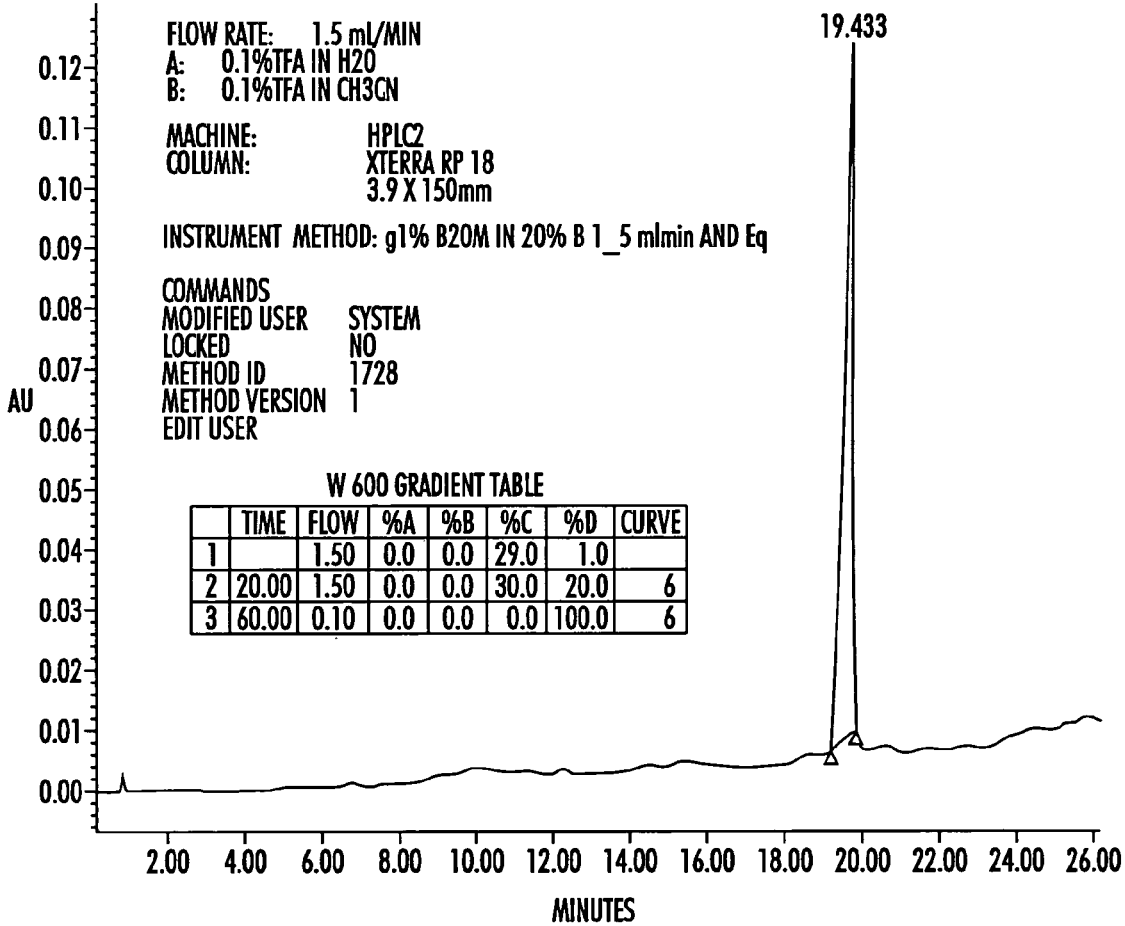
FIG. 20. HPLC analysis of EC31.
Figure 21:
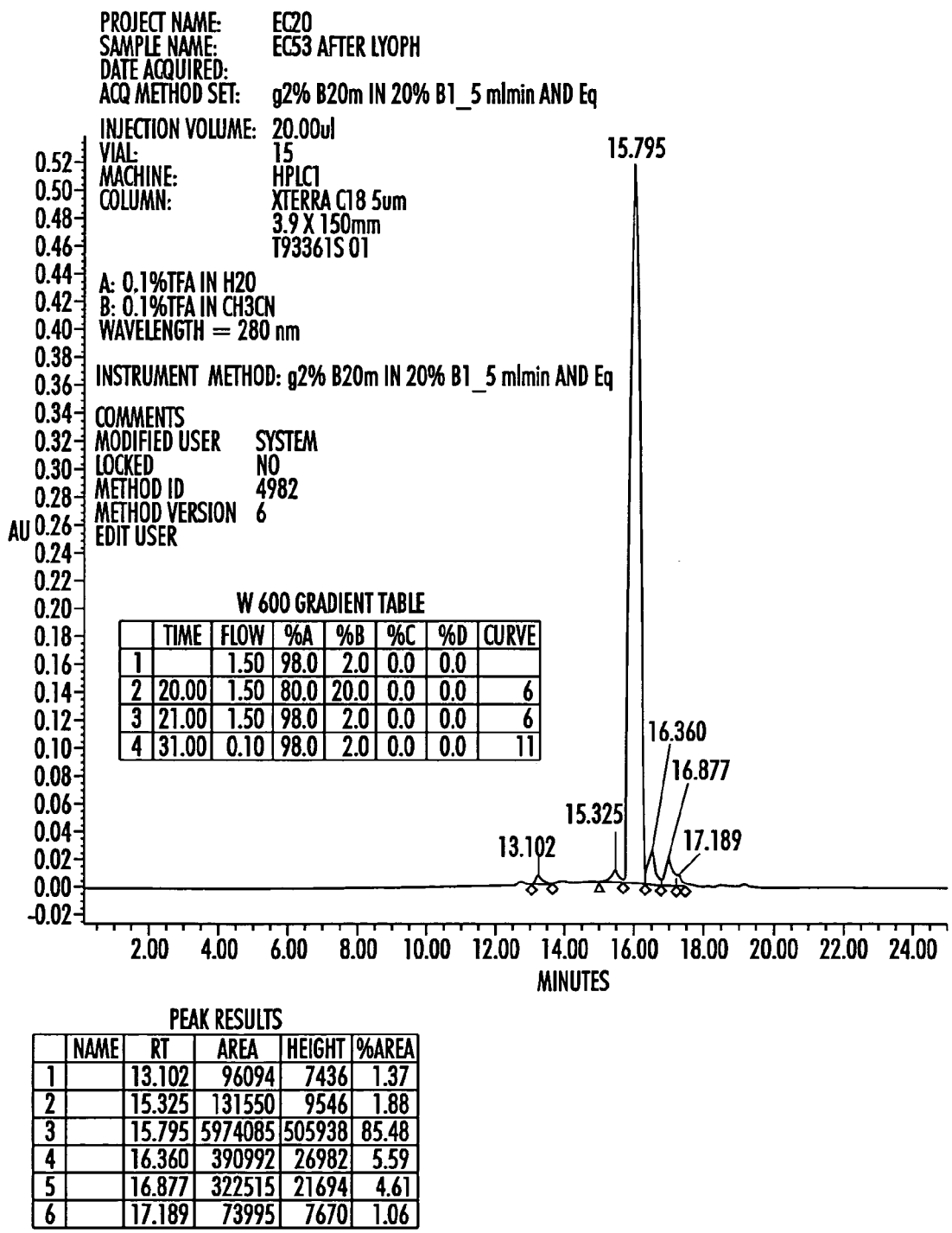
FIG. 21. HPLC analysis of EC53.

As shown in FIG. 11, folate receptor-specific targeting was demonstrated because $^{99m}Tc$-EC20 predominantly accumulated in the FR-positive M109 tumors and kidneys, and not in the FR-negative 4T1 tumors. Uptake in the FR-negative 4T1 tumors was 7.6-fold lower than in the FR-positive M109 tumors. Uptake of $^{99m}Tc$-EC20 in normal tissues, except kidney as expected, was low. These results show that $^{99m}Tc$-EC20 targeting is FR-specific.

EXAMPLE 16

Tissue Distribution Studies.

The protocols used in this example are similar to those described in Example 11. The ability of $^{99m}Tc$-EC11 (peptide-$A_1$), $^{99m}Tc$-EC13 (peptide-$A_3$), and $^{99m}Tc$-EC14 (peptide-$A_2$) to target tumors in vivo was assessed using the FR-positive KB tumor model. Four week-old male nude mice (n=4/group) were maintained on a folate-free diet for a total of ten days prior to tumor cell inoculation.

FR-positive KB tumor cells ($0.25 \times 10^6$ per animal) were inoculated subcutaneously in the intracapsular region. Fourteen days after tumor cell inoculation, the animals (n=4/group) were injected intravenously with $^{99m}Tc$-EC11, $^{99m}Tc$-EC13, or $^{99m}$-Tc-EC14 at the doses (about 12 µg/kg) of the conjugates shown in Table 5 below. Stocks of $^{99m}Tc$-EC11, $^{99m}Tc$-EC13, and $^{99m}Tc$-EC14 solutions were prepared on the day of use as described above. About a 20-fold excess of free folate (about 200 µg/kg) was co-administered to control animals (n=4/group). Four hours post-injection, animals were sacrificed by $CO_2$ asphyxiation, and blood was collected by cardiac puncture and the animals were dissected. Selected tissues were removed, weighed, and counted in an automatic gamma counter to determine $^{99m}Tc$ distribution. Uptake of the radiopharmaceutical in terms of percentage injected dose of wet weight tissue (% ID/g) was calculated by reference to standards prepared from dilutions of the injected preparation.

As shown in Table 5, folate receptor-specific targeting was demonstrated because $^{99m}Tc$-EC11, $^{99m}Tc$-EC13, and $^{99m}Tc$-EC14 predominantly accumulated in the FR-positive KB tumors and kidneys. The accumulation was blocked by co-administration of free folate. These results show that $^{99m}Tc$-EC11, $^{99m}Tc$-EC13, and $^{99m}Tc$-EC14 can target tumors in vivo in a FR-specific manner.

Similar results (see Table 6 below) were obtained with $^{99m}Tc$-EC53 (the all D-enantiomer of EC20) using similar protocols except that the dose of $^{99m}Tc$-EC53 was about 50 µg/kg and about a 100-fold excess of free folate or cold EC53 was used. As shown in Table 6, folate receptor-specific targeting was demonstrated because $^{99m}Tc$-EC53 predominantly accumulated in the FR-positive KB tumors and kidneys. The accumulation was blocked by co-administration of free folate. These results show that $^{99m}Tc$-EC53 can target tumors in vivo in a FR-specific manner.

TABLE 5

| | Percentage of Injected $^{99m}Tc$ Dose per Gram (Tissue Wet Mass) | | | |
| --- | --- | --- | --- | --- |
| | Peptide $A_1$-Folate (EC 11) | | Peptide $A_2$-Folate (EC14) | |
| Tumor mass (g): | 0.112 ± 0.027 | 0.125 ± 0.032 | 0.160 ± 0.037 | 0.171 ± 0.044 |
| Animal Mass (g): | 28.9 ± 1.3 | 27.1 ± 1.6 | 27.6 ± 0.6 | 27.3 ± 2.7 |
| Animal Quantity & Gender: | 4M | 4M | 4M | 4M |
| Folate-Conjugate Dose (µg/kg): | 11.9 ± 0.5 | 13.04 ± 1.12 | 12.6 ± 0.4 | 12.87 ± 1.53 |
| Folic Acid Dihydrate Dose† | | | | |
| (µg/kg): | 0 | 195.1 ± 17.9 | 0 | 192.6 ± 22.9 |
| (µmol/kg): | 0 | 0.41 ± 0.04 | 0 | 0.40 ± 0.05 |
| Blood: | 0.21 ± 0.01 | 0.25 ± 0.01 | 0.19 ± 0.02 | 0.12 ± 0.02 |
| Heart: | 2.5 ± 0.3 | 0.36 ± 0.03 | 3.0 ± 0.5 | 0.24 ± 0.01 |
| Lungs: | 1.2 ± 0.2 | 0.35 ± 0.03 | 1.6 ± 0.3 | 0.24 ± 0.02 |
| Liver & Gall Bladder: | 5.4 ± 1.4 | 1.6 ± 0.1 | 4.5 ± 1.0 | 0.66 ± 0.07 |
| Spleen: | 0.38 ± 0.03 | 0.23 ± 0.01 | 0.41 ± 0.06 | 0.15 ± 0.01 |
| Kidney (one): | 67.8 ± 6.9 | 55.5 ± 2.3 | 44.2 ± 6.4 | 20.6 ± 2.4 |
| Stomach, Intestines & Contents: | 1.4 ± 0.1 | 1.1 ± 0.3 | 1.4 ± 0.1 | 0.50 ± 0.10 |
| Muscle: | 1.8 ± 0.1 | 0.38 ± 0.06 | 2.4 ± 0.4 | 0.26 ± 0.02 |
| Tumor: | 2.95 ± 0.57 | 1.47 ± 0.24 | 5.57 ± 0.76 | 2.0 ± 0.5 |
| Tumor/Blood: | 13.7 ± 2.1 | 5.9 ± 0.9 | 29.3 ± 5.2 | 17.0 ± 4.5 |
| Tumor/Liver: | 0.57 ± 0.14 | 0.94 ± 0.09 | 1.3 ± 0.3 | 3.0 ± 0.6 |
| Tumor/Kidney: | 0.043 ± 0.005 | 0.027 ± 0.005 | 0.13 ± 0.03 | 0.10 ± 0.01 |
| Tumor/Muscle: | 1.6 ± 0.3 | 3.9 ± 0.08 | 2.4 ± 0.6 | 7.7 ± 1.7 |
| | Percentage of Injected $^{99m}Tc$ Dose per Gram (Tissue Wet Mass) | | | |
| | Peptide $A_3$-Folate (EC13) | | HYNIC-Folate | |
| Tumor mass (g): | 0.213 ± 0.067 | 0.0773 ± 0.041 | 0.179 ± 0.060 | 0.150 ± 0.068 |
| Animal Mass (g): | 30.0 ± 1.3 | 27.5 ± 1.4 | 27.5 ± 1.4 | 29.0 ± 2.0 |
| Animal Quantity & Gender: | 4M | 4M | 4M | 4M |

TABLE 5-continued

| | | | | |
|---|---|---|---|---|
| Folate-Conjugate Dose (µg/kg): | 11.7 ± 0.9 | 13.03 ± 1.05 | 1.58 ± 0.03 | 1.46 ± 0.08 |
| Folic Acid Dihydrate Dose† | | | | |
| (µg/kg): | 0 | 191.7 ± 15.5 | 0 | 169.6 ± 9.4 |
| (µmol/kg): | 0 | 0.40 ± 0.03 | 0 | 0.36 ± 0.02 |
| Blood: | 0.25 ± 0.03 | 0.16 ± 0.02 | 0.31 ± 0.06 | 0.25 ± 0.01 |
| Heart: | 1.6 ± 0.1 | 0.20 ± 0.03 | 3.4 ± 0.3 | 0.28 ± 0.02 |
| Lungs: | 1.1 ± 0.1 | 0.23 ± 0.02 | 1.2 ± 0.2 | 0.29 ± 0.03 |
| Liver & Gall Bladder: | 3.5 ± 0.7 | 0.65 ± 0.04 | 3.9 ± 0.9 | 0.62 ± 0.02 |
| Spleen: | 0.39 ± 0.06 | 0.15 ± 0.02 | 0.39 ± 0.12 | 0.17 ± 0.02 |
| Kidney (one): | 54.5 ± 2.4 | 29.1 ± 2.2 | 41.2 ± 8.4 | 38.4 ± 2.6 |
| Stomach, Intestines & Contents: | 2.5 ± 0.2 | 3.7 ± 0.7 | 1.5 ± 0.2 | 1.2 ± 1.0 |
| Muscle: | 1.7 ± 0.2 | 0.21 ± 0.03 | 2.2 ± 0.3 | 0.36 ± 0.06 |
| Tumor: | 5.46 ± 0.45 | 1.67 ± 0.24 | 4.64 ± 0.67 | 2.31 ± 0.27 |
| Tumor/Blood: | 22.5 ± 1.4 | 10.2 ± 1.5 | 15.1 ± 2.1 | 9.1 ± 1.0 |
| Tumor/Liver: | 1.6 ± 0.2 | 2.6 ± 0.3 | 1.3 ± 0.3 | 3.7 ± 0.5 |
| Tumor/Kidney: | 0.10 ± 0.01 | 0.058 ± 0.010 | 0.11 ± 0.01 | 0.069 ± 0.003 |
| Tumor/Muscle: | 3.3 ± 0.3 | 8.2 ± 2.0 | 2.1 ± 0.4 | 6.5 ± 1.3 |

Values shown represent the mean ± standard deviation. Blood was assumed to account for 5.5% of total body mass. Tumor/Background Tissue ratios based on corresponding % Injected Dose per Gram data
†Folic Acid dose co-injected with the $^{99m}$Tc-Folate-Conjugate dose.
n = 3

TABLE 6

| | $^{99m}$Tc-EC53 | | $^{99m}$Tc-EC53 plus Folic Acid | | $^{99m}$Tc-EC53 plus EC53 | |
|---|---|---|---|---|---|---|
| | Average | STD | Average | STD | Average | STD |
| Test Article Dose (ug/kg) | 50.0 | | 50.0 | | 50.0 | |
| (nmol/kg) | 67.0 | | 67.0 | | 67.0 | |
| Co-dosed competitor (nmol/kg) | | | 6700.0 | | 6700.0 | |
| Tumor mass (g) | 0.2 | 0.17 | 0.20 | 0.14 | 0.19 | 0.15 |
| Animals | 3F | | 3F | | 3F | |
| blood | 0.38 | 0.03 | 0.244 | 0.028 | 0.24 | 0.06 |
| heart | 1.09 | 0.28 | 0.15 | 0.03 | 0.19 | 0.03 |
| lung | 0.89 | 0.30 | 0.23 | 0.04 | 0.26 | 0.07 |
| liver | 3.86 | 0.96 | 4.49 | 1.15 | 3.77 | 0.48 |
| intestine | 3.53 | 0.86 | 4.33 | 3.67 | 3.96 | 1.86 |
| kidney | 77.99 | 6.19 | 10.12 | 6.91 | 7.97 | 1.52 |
| muscle | 0.76 | 0.31 | 0.11 | 0.04 | 0.12 | 0.06 |
| spleen | 0.67 | 0.22 | 0.27 | 0.06 | 0.41 | 0.11 |
| stomach | 1.04 | 0.36 | 0.30 | 0.15 | 0.18 | 0.01 |
| Tumor | 11.77 | 4.26 | 0.53 | 0.11 | 1.88 | 1.56 |
| Tumor/Blood | 31.4 | 13.7 | 2.2 | 0.6 | 4.5 | 4.8 |
| Tumor/Liver | 3.4 | 2.2 | 0.1 | 0.0 | 0.3 | 0.4 |
| Tumor/Muscle | 17.1 | 7.0 | 5.2 | 1.4 | 8.5 | 8.0 |
| Tumor/Kidney | 0.2 | 0.07 | 0.07 | 0.05 | 0.14 | 0.16 |

Discussion

The invention provides a conjugate of a vitamin and a radionuclide chelator for clinical development as an imaging agent. Exemplary of such an imaging agent is the newly designed, synthesized, and radiochemically characterized folate-based radionuclide chelator, $^{99m}$Tc-EC20.

$^{99m}$Tc-EC20, a small molecular weight peptide derivative of folate that contains a $_D$-γ-Glu peptide linkage (see FIG. 1), was synthesized using an efficient solid-phase synthetic procedure. In its natural form, folate (or pteroyl-glutamate) has a single glutamyl residue present in an L configuration. However, a $_D$-Glu enantiomer residue was incorporated into the EC20 molecule. Importantly, similar to EC20, substitution of the $_L$-Glu residue in folic acid with a $_D$-Glu residue does not alter the ability of folic acid to bind to the high affinity FR.

EC20 was found to efficiently chelate $^{99m}$Tc when in the presence of α-$_D$-glucoheptonate and tin (II) chloride. When analyzed by radiochemical HPLC, >95% of the resulting $^{99m}$Tc-EC20 formulation consisted of a mixture of syn and anti stereoisomers, each equally capable of binding to FR with high affinity (see FIG. 3). Approximately 3% of the $^{99m}$Tc in the formulation was chelated to EC20 at some other site on the EC20 molecule than the expected Dap-Asp-Cys moiety. Although this component was not isolated in sufficient quantity for optimal characterization, it was shown to bind to FR with high affinity (see FIG. 6). Finally, the remaining 2% of the radioactivity in the $^{99m}$Tc-EC20 formulation was attributed to free $^{99m}$Tc.

$^{99m}$Tc-EC20 demonstrated both time- and concentration-dependent association with FR-positive cells. $^{99m}$Tc-EC20 was rapidly cleared from the blood ($t_{1/2}$~4 min), which is important for diagnostic imaging agents, and $^{99m}$Tc-EC20 preferentially accumulated in large amounts within FR-positive tumors.

The performance of $^{99m}$Tc-EC20 was directly compared to that of a similar FR targeting agent, $^{111}$In-DTPA-Folate, using two different methods. First, both folate-based radiopharmaceuticals were found to equally compete with folic acid for binding to KB FRs (see FIG. 3 and Table 1). Second, the biodistribution of each agent in tumor-bearing mice was nearly identical (see Table 2). High tumor uptake and tumor-to-blood ratios were measured for $^{99m}$Tc-EC20. Taken together these results suggest that like $^{111}$In-DTPA-folate, $^{99m}$Tc-EC20 will effectively localize in FR-positive tumors when clinically administered to patients.

Several folate-based $^{99m}$Tc conjugates have previously been described. Limited biodistribution data is available on a $^{99m}$Tc-12-amino-3,3,9,9-tetramethyl-5-oxa-4,8 diaza-2,10-dodecanedinoe dioxime (OXA) folate conjugate, however moderate levels (~7% ID/g) of tracer uptake in a KB tumor was reported. Studies involving the biodistribution of a $^{99m}$Tc-ethylenedicysteine–folate conjugate in mammary tumor-bearing rats were also reported. The rats in that study were fed a folate-rich diet. Thus, low tumor uptake and low tumor-to-blood ratios were obtained. Lastly, a $^{99m}$Tc-6-hydrazinonicotinamido-hydrazido (HYNIC) folate derivative (HYNIC-folate) was shown to accumulate in large amounts within 24JK-FBP tumors. Interestingly, $^{99m}$Tc-EC20 accumulated within M109 tumors to nearly identical levels as that of HYNIC-folate in 241K-FBP tumors (~17%

ID/g) (Table 2). These two agents also displayed roughly 50:1 tumor-to-blood ratios at 4 hours post intravenous injection.

In summary, a new peptide derivative of folate was created to efficiently chelate $^{99m}$Tc. This new compound, $^{99m}$Tc-EC20, avidly binds to FR-positive tumor cells in vitro and in vivo. EC20, was found to bind cultured folate receptor (FR)-positive tumor cells in both a time- and concentration-dependent manner with very high affinity ($K_D$~3 nM). Using an in vitro relative affinity assay, EC20 was also found to effectively compete with $^3$H-folic acid for cell binding when presented either alone or as a formulated metal chelate. Following intravenous injection into Balb/c mice, $^{99m}$Tc-EC20 was rapidly removed from circulation (plasma $t_{1/2}$~4 min) and excreted into the urine in a non-metabolized form. Data from gamma scintigraphic and quantitative biodistribution studies performed in M109 tumor-bearing Balb/c mice confirmed that $^{99m}$Tc-EC20 predominantly accumulates in FR-positive tumor and kidney tissues. These results show that $^{99m}$Tc-EC20 is an effective, non-invasive radiodiagnostic imaging agent for the detection of FR-positive tumors. Other EC20-related imaging agents were also shown to be effective, including EC11, EC13, EC14, and EC53.

Each year ~26,000 women in the United States are diagnosed with ovarian cancer, and less than 50% of those women survive more than five years. One reason for the low survival rate is the difficulty in diagnosing this form of cancer. Because of the fear of rupturing an unidentified abdominal mass and the potential for spreading cancer throughout the abdominal cavity, fine needle biopsy is not often performed. Rather, the diagnosis and staging of suspicious ovarian masses is typically done through surgical laparotomy, which is an invasive and expensive procedure. Since $^{99m}$Tc-EC20 binds tightly to FR present in large amounts on ovarian cancers (among others), this radiopharmaceutical provides an inexpensive, non-invasive but reliable method for the early diagnosis of malignant ovarian cancer. Importantly, $^{99m}$Tc-EC20 may also help guide the clinical decision process by making possible more definitive and earlier diagnosis of recurrent or residual disease.

What is claimed is:

1. A compound of the formula

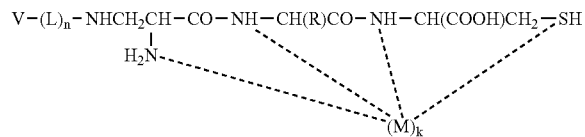

wherein V is a vitamin or V is a receptor-binding analog or derivative of the vitamin, wherein V is a substrate for receptor-mediated transmembrane transport in vivo;

L is a divalent linker;
R is a side chain of an amino acid;
M is a cation of a radionuclide;
n is 1 or 0; and
k is 1 or 0.

2. The compound of claim 1 wherein V is a vitamin selected from the group consisting of folate, riboflavin, thiamine, vitamin $B_{12}$, and biotin, or a vitamin receptor binding derivative or analog thereof.

3. The compound of claim 1 wherein the radionuclide is selected from the group consisting of isotopes of gallium, indium, copper, technetium, and rhenium.

4. The compound of claim 3 wherein the radionuclide is an isotope of technetium.

5. The compound of claim 1 wherein V is folate, or a folate receptor binding analog or derivative thereof.

6. A composition for diagnostic imaging comprising a compound of the formula

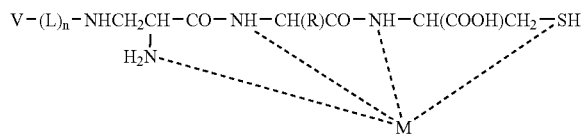

wherein V is a vitamin or V is a receptor-binding analog or derivative of the vitamin, wherein V is a substrate for receptor-mediated transmembrane transport in vivo;

L is a divalent linker;
R is a side chain of an amino acid;
M is a cation of a radionuclide;
n is 1 or 0; and
a pharmaceutically acceptable carrier therefor.

7. The composition of claim 6 wherein V in the compound is a vitamin selected from the group consisting of folate, riboflavin, thiamine, vitamin $B_{12}$, and biotin, or a vitamin receptor binding derivative or analog thereof.

8. The composition of claim 6 wherein the radionuclide in the compound is selected from the group consisting of isotopes of gallium, indium, copper, technetium, and rhenium.

9. The composition of claim 8 wherein the radionuclide in the compound is an isotope of technetium.

10. The composition of claim 6 adapted for parenteral administration.

11. The compound of claim 6 wherein V is folate, or a folate receptor binding analog or derivative thereof.

12. A method of imaging a population of cells in an animal wherein said cells are characterized by a vitamin receptor on the surface of said cells, the method comprising the steps of administering to the animal an effective amount of a composition comprising a compound of the formula

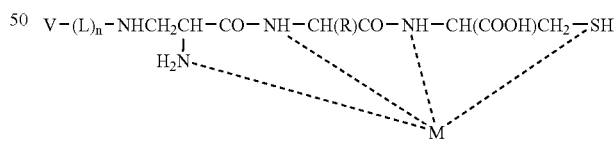

wherein V is the vitamin or V is a vitamin receptor binding derivative or analog of the vitamin, specific for said cell surface vitamin receptor;

L is a divalent linker;
R is a side chain of an amino acid;
M is a cation of a radionuclide;
n is 1 or 0; and
a pharmaceutically acceptable carrier therefor; and
monitoring the biodistribution of said compound in the animal.

13. The method of claim 12 wherein V in the compound is a vitamin selected from the group consisting of folate, riboflavin, thiamine, vitamin $B_{12}$, and biotin, or a vitamin receptor binding derivative or analog thereof.

14. The method of claim 12 wherein the radionuclide in the compound is selected from the group consisting of isotopes of gallium, indium, copper, technetium, and rhenium.

15. The method of claim 14 wherein the radionuclide in the compound is an isotope of technetium.

16. The method of claim 12 wherein the composition is administered parenterally to the animal.

17. The method of claim 12 wherein V is folate, or a folate receptor binding analog or derivative thereof.

18. A compound of the formula $$V-(L)_n-NHCH-CO-NH-CH(R)CO-NH-CH(COOH)CH_2-SH$$
$$\phantom{V-(L)_n-NH}|$$
$$\phantom{V-(L)_n-NH}H_2C$$
$$\phantom{V-(L)_n-NH}/$$
$$\phantom{V-(L)_n-}SH\cdots\cdots\cdots\cdots\cdots\cdots(M)_k$$

wherein V is a vitamin or V is a receptor-binding analog or derivative of the vitamin, wherein V is a substrate for receptor-mediated transmembrane transport in vivo;

L is a divalent linker;

R is a side chain of an amino acid;

M is a cation of a radionuclide;

n is 1 or 0; and k is 1 or 0.

19. A composition for diagnostic imaging comprising a compound of the formula $$V-(L)_n-NHCH-CO-NH-CH(R)CO-NH-CH(COOH)CH_2-SH$$
$$\phantom{V-(L)_n-NH}|$$
$$\phantom{V-(L)_n-NH}H_2C$$
$$\phantom{V-(L)_n-NH}/$$
$$\phantom{V-(L)_n-}SH\cdots\cdots\cdots\cdots\cdots\cdots M$$

wherein V is a vitamin or V is a receptor-binding analog or derivative of the vitamin, wherein V is a substrate for receptor-mediated transmembrane transport in vivo;

L is a divalent linker;

R is a side chain of an amino acid;

M is a cation of a radionuclide;

n is 1 or 0; and a pharmaceutically acceptable carrier therefor.

20. A method of imaging a population of cells in an animal wherein said cells are characterized by a vitamin receptor on the surface of said cells, the method comprising the steps of administering to the animal an effective amount of a composition comprising a compound of the formula $$V-(L)_n-NHCH-CO-NH-CH(R)CO-NH-CH(COOH)CH_2-SH$$
$$\phantom{V-(L)_n-NH}|$$
$$\phantom{V-(L)_n-NH}H_2C$$
$$\phantom{V-(L)_n-NH}/$$
$$\phantom{V-(L)_n-}SH\cdots\cdots\cdots\cdots\cdots\cdots M$$

wherein V is the vitamin or V is a receptor-binding analog or derivative of the vitamin, specific for said cell surface vitamin receptor;

L is a divalent linker;

R is a side chain of an amino acid;

M is a cation of a radionuclide;

n is 1 or 0; and a pharmaceutically acceptable carrier therefor; and monitoring the biodistribution of said compound in the animal.

21. The compound of claim 18 wherein V is a vitamin selected from the group consisting of folate, riboflavin, thiamine, vitamin $B_{12}$, and biotin, or a vitamin receptor binding derivative or analog thereof.

22. The compound of claim 18 wherein the radionuclide is selected from the group consisting of isotopes of gallium, indium, copper, technetium, and rhenium.

23. The compound of claim 22 wherein the radionuclide is an isotope of technetium.

24. The compound of claim 18 wherein V is folate, or a folate receptor binding analog or derivative thereof.

25. The composition of claim 19 wherein V is a vitamin selected from the group consisting of folate, riboflavin, thiamine, vitamin $B_{12}$, and biotin, or a vitamin receptor binding derivative or analog thereof.

26. The composition of claim 19 wherein the radionuclide is selected from the group consisting of isotopes of gallium, indium, copper, technetium, and rhenium.

27. The composition of claim 26 wherein the radionuclide is an isotope of technetium.

28. The composition of claim 19 wherein V is folate, or a folate receptor binding analog or derivative thereof.

29. The composition of claim 19 adapted for parenteral administration.

30. The method of claim 20 wherein V is a vitamin selected from the group consisting of folate, riboflavin, thiamine, vitamin $B_{12}$, and biotin, or a vitamin receptor binding derivative or analog thereof.

31. The method of claim 20 wherein the radionuclide is selected from the group consisting of isotopes of gallium, indium, copper, technetium, and rhenium.

32. The method of claim 31 wherein the radionuclide is an isotope of technetium.

33. The method of claim 20 wherein V is folate, or a folate receptor binding analog or derivative thereof.

34. The method of claim 20 wherein the composition is administered parenterally to the animal.

* * * * *

UNITED STATES PATENT AND TRADEMARK OFFICE
CERTIFICATE OF CORRECTION

| | | |
|---|---|---|
| PATENT NO. | : 7,128,893 B2 | Page 1 of 1 |
| APPLICATION NO. | : 10/430519 | |
| DATED | : October 31, 2006 | |
| INVENTOR(S) | : Leamon et al. | |

It is certified that error appears in the above-identified patent and that said Letters Patent is hereby corrected as shown below:

In the drawings, Sheet 7, Fig. 10B, the formula labeled EC20 (Pte-D-ãGlu-L-âDpr-L-Asp-L-Cys) should be replaced with the formula shown below:

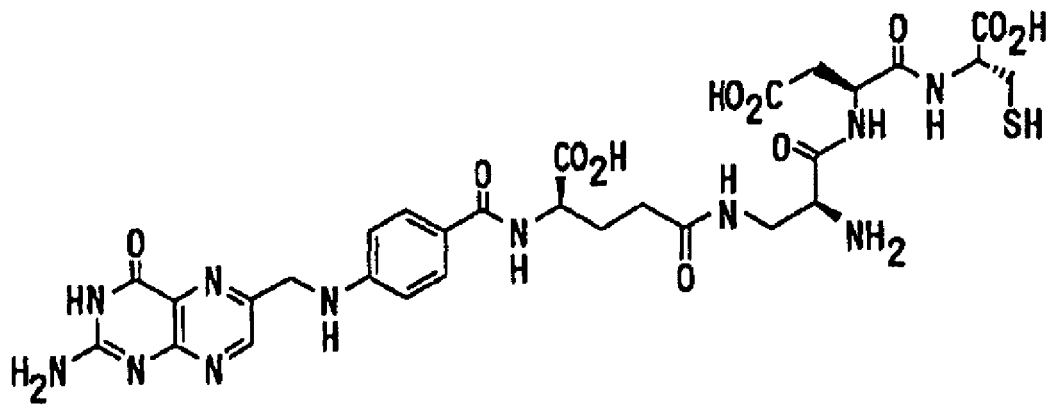

Signed and Sealed this

Twenty-sixth Day of January, 2010

David J. Kappos
*Director of the United States Patent and Trademark Office*